US009133239B2

(12) United States Patent
Cao et al.

(10) Patent No.: US 9,133,239 B2
(45) Date of Patent: Sep. 15, 2015

(54) COMPOSITIONS AND METHODS FOR INHIBITING MATRIX METALLOPROTEINASE (MMP)-MEDIATED CELL MIGRATION

(75) Inventors: Jian Cao, S. Setauket, NY (US); Antoine Dufour, Vancouver (CA)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 88 days.

(21) Appl. No.: 13/642,078

(22) PCT Filed: Apr. 19, 2011

(86) PCT No.: PCT/US2011/033057
§ 371 (c)(1),
(2), (4) Date: Jan. 2, 2013

(87) PCT Pub. No.: WO2011/133555
PCT Pub. Date: Oct. 27, 2011

(65) Prior Publication Data
US 2013/0123192 A1 May 16, 2013

Related U.S. Application Data

(60) Provisional application No. 61/325,962, filed on Apr. 20, 2010.

(51) Int. Cl.
| | | |
|---|---|---|
| *A61K 38/08* | (2006.01) | |
| *A61K 38/04* | (2006.01) | |
| *C07K 7/00* | (2006.01) | |
| *C07K 7/06* | (2006.01) | |
| *C12N 9/64* | (2006.01) | |
| *A61K 38/00* | (2006.01) | |

(52) U.S. Cl.
CPC ............... *C07K 7/06* (2013.01); *C12N 9/6491* (2013.01); *A61K 38/00* (2013.01)

(58) Field of Classification Search
CPC ............... C07K 16/30; C07K 14/8146; C07K 2319/00; C07K 2319/70; A61K 38/00; A61K 38/08; A61K 38/1709; A61K 38/4886; A61K 49/0056; A61K 49/14
See application file for complete search history.

(56) References Cited

U.S. PATENT DOCUMENTS

| | | | | |
|---|---|---|---|---|
| 4,244,946 | A | 1/1981 | Rivier et al. | 514/9.9 |
| 5,057,313 | A | 10/1991 | Shih et al. | 424/999.999 |
| 5,475,092 | A | 12/1995 | Chari et al. | 530/391.7 |
| 5,585,499 | A | 12/1996 | Chari et al. | 548/202 |
| 5,837,493 | A * | 11/1998 | Hillman et al. | 435/69.1 |
| 5,846,545 | A | 12/1998 | Chari et al. | 424/195.11 |
| 5,851,789 | A | 12/1998 | Simon et al. | 435/32 |
| 6,022,948 | A * | 2/2000 | Goldberg | 530/326 |
| 6,238,878 | B1 | 5/2001 | Jakobsen et al. | 435/13 |
| 6,333,410 | B1 | 12/2001 | Chari et al. | 540/456 |
| 6,340,701 | B1 | 1/2002 | Chari et al. | 549/200 |
| 6,372,738 | B2 | 4/2002 | Chari et al. | 514/232.5 |
| 6,632,979 | B2 | 10/2003 | Erickson et al. | 800/18 |
| 6,905,839 | B2 | 6/2005 | Furuta | 435/29 |
| 7,202,346 | B2 | 4/2007 | Payne et al. | 530/388.1 |
| 7,662,387 | B2 | 2/2010 | Law et al. | 424/178.1 |
| 7,666,425 | B1 | 2/2010 | Bander | 424/181.1 |
| 2004/0120954 | A1 | 6/2004 | Seiki et al. | 435/6 |
| 2008/0221017 | A1 | 9/2008 | Msika et al. | 514/183 |
| 2009/0311245 | A1 | 12/2009 | Devy et al. | 530/387.3 |

OTHER PUBLICATIONS

Lehti et al (Journal of Biological Chemistry, 2002, 277:8440-8448).*
Itoh et al (The EMBO Journal, 2001, 20:4782-4793).*
Afzal, S. et al. (1998) "MT1-MMP and MMP-2 mRNA expression in human ovarian tumors: Possible implications for the role of desmoplastic fibroblasts," *Human Pathology* 29(2), 155-165.
Aina, O. H. et al. (2002) "Therapeutic cancer targeting peptides," *Peptide Science* 66(3), 184-199.
Albrecht-Buehler, G. (1977) "The phagokinetic tracks of 3T3 cells," *Cell* 11(2), 395-404.
Arap, W. et al. (2002) "Targeting the prostate for destruction through a vascular address," *Proceedings of the National Academy of Sciences* 99(3), 1527-1531.
Atherton, E. et al. (1985) "Peptide synthesis. Part 7. Solid-phase synthesis of conotoxin G1," *Journal of the Chemical Society, Perkin Transactions 1*, 2065-2073.
Atkinson, S. J. et al. (2004) "Cellular cholesterol regulates MT1 MMP dependent activation of MMP 2 via MEK-1 in HT1080 fibrosarcoma cells," *FEBS Letters* 566(1-3), 65-70.
Bachelder, R. E. et al. (2005) "Glycogen synthase kinase-3 is an endogenous inhibitor of Snail transcription: implications for the epithelial—mesenchymal transition," *Journal of Cell Biology* 168(1), 29-33.
Balbo, A. et al. (2005) "Studying multiprotein complexes by multisignal sedimentation velocity analytical ultracentrifugation," *Proceedings of the National Academy of Sciences of the United States of America* 102(1), 81-86.
Bartolomé, R. A. et al. (2004) "Stromal Cell-Derived Factor-1α Promotes Melanoma Cell Invasion across Basement Membranes Involving Stimulation of Membrane-Type 1 Matrix Metalloproteinase and Rho GTPase Activities," *Cancer Research* 64(7), 2534-2543.
Bates, R. C. et al. (2003) "Tumor Necrosis Factor-α Stimulates the Epithelial-to-Mesenchymal Transition of Human Colonic Organoids," *Molecular Biology of the Cell* 14(5), 1790-1800.

(Continued)

*Primary Examiner* — Sean Aeder
*Assistant Examiner* — Julie Wu
(74) *Attorney, Agent, or Firm* — Medlen + Carroll, LLP

(57) ABSTRACT

The invention provides peptides, portions and derivatives thereof, that are useful for reducing cell migration, and for reducing symptoms of pathological diseases that are associated with undesirable cell migration, and in particular MMP-induced cell migration. This invention also provides peptides that are useful for detecting (e.g., imaging) cancers.

11 Claims, 50 Drawing Sheets

(56) References Cited

OTHER PUBLICATIONS

Beavis, M. J. et al. (1997) "Human peritoneal fibroblast proliferation in 3-dimensional culture: Modulation by cytokines, growth factors and peritoneal dialysis effluent," *Kidney International* 51(1), 205-215.

Bennett, K. L. et al. (1995) "CD44 isoforms containing exon V3 are responsible for the presentation of heparin-binding growth factor," *Journal of Cell Biology* 128(4), 687-698.

Bergers, G. et al. (1999) "Effects of Angiogenesis Inhibitors on Multistage Carcinogenesis in Mice," *Science* 284(5415), 808-812.

Birkedal-Hansen, H. et al. (1993) "Matrix Metalloproteinases: A Review," *Critical Reviews in Oral Biology & Medicine* 4(2), 197-250.

Björklund, M. et al. (2004) "Peptide Inhibition of Catalytic and Noncatalytic Activities of Matrix Metalloproteinase-9 Blocks Tumor Cell Migration and Invasion," *Journal of Biological Chemistry* 279(28), 29589-29597.

Bode, W. et al. (1999) "Structural properties of matrix metalloproteinases," *Cellular and Molecular Life Sciences CMLS* 55(4), 639-652.

Borghouts, C. et al. (2005) "Current strategies for the development of peptide-based anti-cancer therapeutics," *Journal of Peptide Science* 11(11), 713-726.

Boyer, B. et al. (2000) "Induction and regulation of epithelial—mesenchymal transitions," *Biochemical Pharmacology* 60(8), 1091-1099.

Brabletz, T. et al. (2001) "Variable β-catenin expression in colorectal cancers indicates tumor progression driven by the tumor environment," *Proceedings of the National Academy of Sciences* 98(18), 10356-10361.

Brinckerhoff, C. E. et al. (2002) "Matrix metalloproteinases: a tail of a frog that became a prince," *Nature Reviews Molecular Cell Biology* 3(3), 207-214.

Brooks, P. C. et al. (1998) "Disruption of Angiogenesis by PEX, a Noncatalytic Metalloproteinase Fragment with Integrin Binding Activity," *Cell* 92(3), 391-400.

Brown, P. (1997) "Matrix metalloproteinase inhibitors," *Angiogenesis* 1(2), 142-154.

Cao, J. et al. (2005) "Membrane type 1-matrix metalloproteinase promotes human prostate cancer invasion and metastasis," *Thrombosis and Haemostasis* 93(4), 770-778.

Cao, J. et al. (2004) "Distinct Roles for the Catalytic and Hemopexin Domains of Membrane Type 1-Matrix Metalloproteinase in Substrate Degradation and Cell Migration," *Journal of Biological Chemistry* 279(14), 14129-14139.

Cao, J. et al. (1995) "The C-terminal Region of Membrane Type Matrix Metalloproteinase Is a Functional Transmembrane Domain Required for Pro-gelatinase A Activation," *Journal of Biological Chemistry* 270(2), 801-805.

Cha, H. et al. (2002) "Structural Basis of the Adaptive Molecular Recognition by MMP9," *Journal of Molecular Biology* 320(5), 1065-1079.

Chang, D. K. et al. (2009) "A novel peptide enhances therapeutic efficacy of liposomal anti-cancer drugs in mice models of human lung cancer," *PLoS One* 4(1), e4171.

Cheng, S. et al. (2003) "Gelatinase A (MMP-2) Is Necessary and Sufficient for Renal Tubular Cell Epithelial-Mesenchymal Transformation," *American Journal of Pathology* 162(6), 1937-1949.

Cheong, K. H. et al. (1999) "VIP17/MAL, a lipid raft-associated protein, is involved in apical transport in MDCK cells," *Proceedings of the National Academy of Sciences* 96(11), 6241-6248.

Chesire, D. R. et al. (2002) "In vitro evidence for complex modes of nuclear beta-catenin signaling during prostate growth and tumorigenesis," *Oncogene* 21(17), 2679-2694.

Chun, T.-H. et al. (2004) "MT1-MMP—dependent neovessel formation within the confines of the three-dimensional extracellular matrix," *Journal of Cell Biology* 167(4), 757-767.

Coll, J. L. et al. (1995) "Targeted disruption of vinculin genes in F9 and embryonic stem cells changes cell morphology, adhesion, and locomotion," *Proceedings of the National Academy of Sciences* 92(20), 9161-9165.

Coussens, L. M. et al. (2002) "Matrix Metalloproteinase Inhibitors and Cancer—Trials and Tribulations," *Science* 295(5564), 2387-2392.

Crinò, L. (2002) "HER-2 inhibitors: clinical results," *I supplementi di Tumori : official journal of Società italiana di cancerologia . . . [et al.]* 1(6), S3-4.

David, G. S. et al. (1974) "Protein iodination with solid state lactoperoxidase," *Biochemistry* 13(5), 1014-1021.

Deryugina, E. I. et al. (2000) "Functional activation of integrin αvβ3 in tumor cells expressing membrane-type 1 matrix metalloproteinase," *International Journal of Cancer* 86(1), 15-23.

Deryugina, E. I. et al. (2002) "Up-Regulation of Vascular Endothelial Growth Factor by Membrane-type 1 Matrix Metalloproteinase Stimulates Human Glioma Xenograft Growth and Angiogenesis," *Cancer Research* 62(2), 580-588.

Dong, Z. et al. (1997) "A dominant negative mutant of jun blocking 12—O—tetradecanoylphorbol—13—acetate-induced invasion in mouse keratinocytes," *Molecular Carcinogenesis* 19(3), 204-212.

Dufour, A. et al. (2008) "Role of the hemopexin domain of matrix metalloproteinases in cell migration," *Journal of Cellular Physiology* 217(3), 643-651.

Duong, T. D. et al. (2004) "MMP-2 plays an essential role in producing epithelial-mesenchymal transformations in the avian embryo," *Developmental Dynamics* 229(1), 42-53.

Egeblad, M. et al. (2002) "New functions for the matrix metalloproteinases in cancer progression," *Nature Reviews Cancer* 2(3), 161-174.

Ellerby, H. M. et al. (1999) "Anti-cancer activity of targeted pro-apoptotic peptides," *Nature Medicine* 5(9), 1032-1038.

Enmon, R. M. et al. (2002) "Aggregation kinetics of well and poorly differentiated human prostate cancer cells," *Biotechnology and Bioengineering* 80(5), 580-588.

Ezhilarasan, R. et al. (2009) "The hemopexin domain of MMP-9 inhibits angiogenesis and retards the growth of intracranial glioblastoma xenograft in nude mice," *International Journal of Cancer* 124(2), 306-315.

Faisal, S. M. et al. (2009) "Leptosome-entrapped leptospiral antigens conferred significant higher levels of protection than those entrapped with PC-liposomes in a hamster model," *Vaccine* 27(47), 6537-6545.

Fields, G. B. et al. (1990) "Solid phase peptide synthesis utilizing 9-fluorenylmethoxycarbonyl amino acids," *International Journal of Peptide & Protein Research* 35(3), 161-214.

Fingleton, B. M. et al. (1999) "Matrilysin in early stage intestinal tumorigenesis," *APMIS* 107(1-6), 102-110.

Gálvez, B. G. et al. (2002) "ECM regulates MT1-MMP localization with β1 or αvβ3 integrins at distinct cell compartments modulating its internalization and activity on human endothelial cells," *Journal of Cell Biology* 159(3), 509-521.

Geiger, B. (1991) "The cytoplasmic domain of adherens-type junctions," *Cell Motility and the Cytoskeleton* 20(1), 1-6.

Gingras, D. et al. (2001) "Activation of the extracellular signal-regulated protein kinase (ERK) cascade by membrane-type-1 matrix metalloproteinase (MT1-MMP)," *FEBS Letters* 507(2), 231-236.

Gotzmann, J. (2004) "Molecular aspects of epithelial cell plasticity: implications for local tumor invasion and metastasis," *Mutation Research* 566(1), 9-20.

Grunert, S. et al. (2003) "Diverse cellular and molecular mechanisms contribute to epithelial plasticity and metastasis," *Nature Reviews Molecular Cell Biology* 4(8), 657-665.

Guhlke, S. et al. (1998) "188Re- and 99mTc-MAG3 as prosthetic groups for labeling amines and peptides: Approaches with pre- and postconjugate labeling," *Nuclear Medicine and Biology* 25(7), 621-631.

Hanahan, D. et al. (2000) "The Hallmarks of Cancer," *Cell* 100(1), 57-70.

Hazan, R. B. et al. (1997) "Vinculin is Associated with the E-cadherin Adhesion Complex," *Journal of Biological Chemistry* 272(51), 32448-32453.

(56) References Cited

OTHER PUBLICATIONS

Henderson, B. R. et al. (2002) "The ins and outs of APC and [beta]-catenin nuclear transport," *EMBO Reports* 3(9), 834-839.
Hess, A. R. et al. (2003) "Phosphoinositide 3-Kinase Regulates Membrane Type 1-Matrix Metalloproteinase (MMP) and MMP-2 Activity during Melanoma Cell Vasculogenic Mimicry," *Cancer Research* 63(16), 4757-4762.
Hidalgo, M. et al. (2001) "Development of Matrix Metalloproteinase Inhibitors in Cancer Therapy," *Journal of the National Cancer Institute* 93(3), 178-193.
Hiraoka, N. et al. (1998) "Matrix Metalloproteinases Regulate Neovascularization by Acting as Pericellular Fibrinolysins," *Cell* 95(3), 365-377.
Hlubek, F. et al. (2004) "β-Catenin activates a coordinated expression of the proinvasive factors laminin-5 γ2 chain and MT1-MMP in colorectal carcinomas," *International Journal of Cancer* 108(2), 321-326.
Hotary, K. et al. (2000) "Regulation of Cell Invasion and Morphogenesis in a Three-Dimensional Type I Collagen Matrix by Membrane-Type Matrix Metalloproteinases 1, 2, and 3," *Journal of Cell Biology* 149(6), 1309-1323.
Hotary, K. B. et al. (2003) "Membrane Type I Matrix Metalloproteinase Usurps Tumor Growth Control Imposed by the Three-Dimensional Extracellular Matrix," *Cell* 114(1), 33-45.
Huber, M. A. et al. (2004) "NF-κB is essential for epithelial-mesenchymal transition and metastasis in a model of breast cancer progression," *Journal of Clinical Investigation* 114(4), 569-581.
Hunter, W. M. et al. (1962) "Preparation of iodine-131 labelled human growth hormone of high specific activity," *Nature* 194, 495-496.
Huwyler, J. et al. (2008) "Tumor targeting using liposomal antineoplastic drugs," *International Journal of Nanomedicine* 3(1), 21-29.
Ikenouchi, J. et al. (2003) "Regulation of tight junctions during the epithelium-mesenchyme transition: direct repression of the gene expression of claudins/occludin by Snail," *Journal of Cell Science* 116(10), 1959-1967.
Ito, K. et al. (1999) "Calcium influx triggers the sequential proteolysis of extracellular and cytoplasmic domains of E-cadherin, leading to loss of beta-catenin from cell-cell contacts," *Oncogene* 18(50), 7080-7090.
Itoh, Y. et al. (2001) "Homophilic complex formation of MT1-MMP facilitates proMMP-2 activation on the cell surface and promotes tumor cell invasion," *EMBO Journal* 20(17), 4782-4793.
Iwano, M. et al. (2002) "Evidence that fibroblasts derive from epithelium during tissue fibrosis," *Journal of Clinical Investigation* 110(3), 341-350.
Jalkanen, S. et al. (1992) "Lymphocyte CD44 binds the COOH-terminal heparin-binding domain of fibronectin," *Journal of Cell Biology* 116(3), 817-825.
Janda, E. et al. (2002) "Ras and TGFβ cooperatively regulate epithelial cell plasticity and metastasis: dissection of Ras signaling pathways," *Journal of Cell Biology* 156(2), 299-314.
Jiang, A. et al. (2001) "Regulation of membrane-type matrix metalloproteinase 1 activity by dynamin-mediated endocytosis," *Proceedings of the National Academy of Sciences* 98(24), 13693-13698.
Kajita, M. et al. (2001) "Membrane-Type 1 Matrix Metalloproteinase Cleaves Cd44 and Promotes Cell Migration," *Journal of Cell Biology* 153(5), 893-904.
Kamber, B. et al. (1980) "The Synthesis of Cystine Peptides by Iodine Oxidation of S-Trityl-cysteine and S-Acetamidomethyl-cysteine Peptides," *Helvetica Chimica Acta* 63(4), 899-915.
Kang, Y. et al. (2004) "Epithelial-Mesenchymal Transitions: Twist in Development and Metastasis," *Cell* 118(3), 277-279.
Kawano, K. et al. (2001) "Integrin α3β1 Engagement Disrupts Intercellular Adhesion," *Experimental Cell Research* 262(2), 180-196.
Koshikawa, N. et al. (2000) "Role of Cell Surface Metalloprotease MT1-MMP in Epithelial Cell Migration over Laminin-5," *Journal of Cell Biology* 148(3), 615-624.
Krause, W. et al. (1996) "Ytterbium- and dysprosium-EOB-DTPA. A new prototype of liver-specific contrast agents for computed tomography," *Investigative Radiology* 31(8), 502-511.
Lever, R. et al. (2002) "Novel drug development opportunities for heparin," *Nature Reviews Drug Discovery* 1(2), 140-148.
Li, J. et al. (1995) "Structure of full-length porcine synovial collagenase reveals a C-terminal domain containing a calcium-linked, four-bladed β-propeller," *Structure* 3(6), 541-549.
Lochter, A. et al. (1997) "Matrix Metalloproteinase Stromelysin-1 Triggers a Cascade of Molecular Alterations That Leads to Stable Epithelial-to-Mesenchymal Conversion and a Premalignant Phenotype in Mammary Epithelial Cells," *Journal of Cell Biology* 139(7), 1861-1872.
Loennechen, T. et al. (2003) "Colchicine induces membrane-associated activation of matrix metalloproteinase-2 in osteosarcoma cells in an S100A4-independent manner," *Biochemical Pharmacology* 66(12), 2341-2353.
Loughlin, W. A. et al. (2004) "Beta-Strand Mimetics," *Chemical Reviews* 104(12), 6085-6118.
Marambaud, P. et al. (2002) "A presenilin-1/gamma-secretase cleavage releases the E-cadherin intracellular domain and regulates disassembly of adherens junctions," *EMBO Journal* 21(8), 1948-1956.
Matrisian, L. M. et al. (2003) "Extracellular Proteolysis and Cancer: Meeting Summary and Future Directions," *Cancer Research* 63(19), 6105-6109.
Mattrey, R. F. (1990) "In vivo estimation of perfluorooctylbromide concentration in tissues," *Investigative Radiology* 25(8), 915-921.
Meienhofer, J. (1973) *Hormonal Proteins and Peptides* 2, 46.
Merrifield, R. B. (1969) "Solid-phase peptide synthesis," *Advances in enzymology and related subjects* 32, 221-296.
Mitchell, S. et al. (2000) "Phenotypic and genotypic characterization of commonly used human prostatic cell lines," *BJU International* 85(7), 932-944.
Miura, Y. et al. (2002) "Analysis of the Interaction of Platelet Collagen Receptor Glycoprotein Vi (GPVI) with Collagen: A Dimeric Form of GPVI, but Not the Monomeric Form, Shows Affinity to Fibrous Collagen," *Journal of Biological Chemistry* 277(48), 46197-46204.
Moon, R. T. et al. (2002) "The Promise and Perils of Wnt Signaling Through β-Catenin," *Science* 296(5573), 1644-1646.
Morali, O. G. et al. (2001) "IGF-II induces rapid beta-catenin relocation to the nucleus during epithelium to mesenchyme transition," *Oncogene* 20(36), 4942-4950.
Mori, H. H et al. (2002) "CD44 directs membrane-type 1 matrix metalloproteinase to lamellipodia by associating its ts hemopexin-like domain," *EMBO Journal* 21(15), 3949-3959.
Morin, P. J. (1999) "β-catenin signaling and cancer," *BioEssays* 21(12), 1021-1030.
Mu, D. et al. (2002) "The integrin αvβ8 mediates epithelial homeostasis through MT1-MMP—dependent activation of TGF-β1," *Journal of Cell Biology* 157(3), 493-507.
Munshi, H. G. et al. (2004) "Differential Regulation of Membrane Type 1-Matrix Metalloproteinase Activity by ERK 1/2- and p38 MAPK-modulated Tissue Inhibitor of Metalloproteinases 2 Expression Controls Transforming Growth Factor-β1-induced Pericellular Collagenolysis," *Journal of Biological Chemistry* 279(37), 39042-39050.
Nagakawa, O. et al. (2000) "Expression of membrane-type 1 matrix metalloproteinase (MT1-MMP) on prostate cancer cell lines," *Cancer Letters* 155(2), 173-179.
Nakada, M. et al. (1999) "Expression and Tissue Localization of Membrane-Type 1, 2, and 3 Matrix Metalloproteinases in Human Astrocytic Tumors," *American Journal of Pathology* 154(2), 417-428.
Niv, M. Y. et al. (2004) "Sequence-based Design of Kinase Inhibitors Applicable for Therapeutics and Target Identification," *Journal of Biological Chemistry* 279(2), 1242-1255.
Nygren, H. (1982) "Conjugation of horseradish peroxidase to Fab fragments with different homobifunctional and heterobifunctional cross-linking reagents. A comparative study," *Journal of Histochemistry and Cytochemistry* 30(5), 407-412.
Oft, M. et al. (1998) "TGFβ signaling is necessary for carcinoma cell invasiveness and metastasis," *Current Biology* 8(23), 1243-1252.

(56) References Cited

OTHER PUBLICATIONS

Oft, M. et al. (1996) "TGF-beta 1 and Ha-Ras collaborate in modulating the phenotypic plasticity and invasiveness of epithelial tumor cells," *Genes & Development* 10(19), 2462-2477.

Ohuchi, E. et al. (1997) "Membrane Type 1 Matrix Metalloproteinase Digests Interstitial Collagens and Other Extracellular Matrix Macromolecules," *Journal of Biological Chemistry* 272(4), 2446-2451.

Otto, J. J. (1990) "Vinculin," *Cell Motility and the Cytoskeleton* 16(1), 1-6.

Overall, C. M. et al. (2002) "Strategies for MMP inhibition in cancer: innovations for the post-trial era," *Nature Reviews Cancer* 2(9), 657-672.

Pain, D. et al. (1981) "Preparation of protein A-peroxidase monoconjugate using a heterobifunctional reagent, and its use in enzyme immunoassays," *Journal of Immunological Methods* 40(2), 219-230.

Pall, T. et al. (2004) "Recombinant CD44-HABD is a novel and potent direct angiogenesis inhibitor enforcing endothelial cell-specific growth inhibition independently of hyaluronic acid binding," *Oncogene* 23(47), 7874-7881.

Park, B.-J. et al. (2000) "Mitogenic Conversion of Transforming Growth Factor-β1 Effect by Oncogenic Ha-Ras-induced Activation of the Mitogen-activated Protein Kinase Signaling Pathway in Human Prostate Cancer," *Cancer Research* 60(11), 3031-3038.

Pavlaki, M. et al. (2002) "A Conserved Sequence within the Propeptide Domain of Membrane Type 1 Matrix Metalloproteinase Is Critical for Function as an Intramolecular Chaperone," *Journal of Biological Chemistry* 277(4), 2740-2749.

Pavlaki, M. et al. (2003) "Matrix metalloproteinase inhibitors (MMPIs): the beginning of phase I or the termination of phase III clinical trials," *Cancer and Metastasis Reviews* 22(2-3), 177-203.

Persad, S. et al. (2001) "Tumor Suppressor Pten Inhibits Nuclear Accumulation of β-Catenin and T Cell/Lymphoid Enhancer Factor 1—Mediated Transcriptional Activation," *Journal of Cell Biology* 153(6), 1161-1174.

Petersen, O. W. et al. (2003) "Epithelial to Mesenchymal Transition in Human Breast Cancer Can Provide a Nonmalignant Stroma," *American Journal of Pathology* 162(2), 391-402.

Philip, S. et al. (2003) "Osteopontin Induces Nuclear Factor κB-mediated Promatrix Metalloproteinase-2 Activation through IκBα/IKK Signaling Pathways, and Curcumin (Diferulolylmethane) Down-regulates These Pathways," *Journal of Biological Chemistry* 278(16), 14487-14497.

Pitot, H. C. (1978) "The Language of Oncology," in *Fundamentals of Oncology* (Dekker, M., Ed.), pp. 15-28, New York.

Plaué, S. (1990) "Synthesis of cyclic peptides on solid support. Application to analogs of hemagglutinin of influenza virus," *International Journal of Peptide & Protein Research* 35(6), 510-517.

Polakis, P. (2000) "Wnt signaling and cancer," *Genes & Development* 14(15), 1837-1851.

Rauh, D. et al. (2004) "Understanding Protein—Ligand Interactions: The Price of Protein Flexibility," *Journal of Molecular Biology* 335(5), 1325-1341.

Raz, A. et al. (1982) "Altered Organization of Cell-Substrate Contacts and Membrane-associated Cytoskeleton in Tumor Cell Variants Exhibiting Different Metastatic Capabilities," *Cancer Research* 42(12), 5183-5190.

Roeb, E. et al. (2002) "The Matrix Metalloproteinase 9 (MMP-9) Hemopexin Domain Is a Novel Gelatin Binding Domain and Acts as an Antagonist," *Journal of Biological Chemistry* 277(52), 50326-50332.

Rozanov, D. V. et al. (2004) "Aberrant, persistent inclusion into lipid rafts limits the tumorigenic function of membrane type-1 matrix metalloproteinase in malignant cells," *Experimental Cell Research* 293(1), 81-95.

Sabeh, F. et al. (2004) "Tumor cell traffic through the extracellular matrix is controlled by the membrane-anchored collagenase MT1-MMP," *Journal of Cell Biology* 167(4), 769-781.

Sato, H. et al. (1994) "A matrix metalloproteinase expressed on the surface of invasive tumour cells," *Nature* 370(6484), 61-65.

Savagner, P. (2001) "Leaving the neighborhood: molecular mechanisms involved during epithelial-mesenchymal transition," *BioEssays* 23(10), 912-923.

Schäfer, R. et al. (2003) "Impaired VE-Cadherin/β-Catenin Expression Mediates Endothelial Cell Degeneration in Dilated Cardiomyopathy," *Circulation* 108(13), 1585-1591.

Seiki, M. et al. (2003) "Role of pericellular proteolysis by membrane-type 1 matrix metalloproteinase in cancer invasion and angiogenesis," *Cancer and Metastasis Reviews* 22(2-3), 129-143.

Sharma, M. et al. (2002) "Phosphatidylinositol 3-Kinase/Akt Stimulates Androgen Pathway through GSK3β Inhibition and Nuclear β-Catenin Accumulation," *Journal of Biological Chemistry* 277(34), 30935-30941.

Sieg, D. J. et al. (1999) "Required role of focal adhesion kinase (FAK) for integrin-stimulated cell migration," *Journal of Cell Science* 112(16), 2677-2691.

Sirlin, C. B. et al. (1999) "Effect of acquisition rate on liver and portal vein enhancement with microbubble contrast," *Ultrasound in Medicine & Biology* 25(3), 331-338.

Song, S. et al. (2008) "Peptide ligand-mediated liposome distribution and targeting to EGFR expressing tumor in vivo," *International Journal of Pharmaceutics* 363(1-2), 155-161.

Sounni, N. E. et al. (2003) "Membrane type-1 matrix metalloproteinase and TIMP-2 in tumor angiogenesis," *Matrix Biology* 22(1), 55-61.

Sternlicht, M. D. et al. (2001) "How Matrix Metalloproteinases Regulate Cell Behavior," *Annual Review of Cell and Developmental Biology* 17(1), 463-516.

Strizzi, L. et al. (2004) "Epithelial mesenchymal transition is a characteristic of hyperplasias and tumors in mammary gland from MMTV-Cripto-1 transgenic mice," *Journal of Cellular Physiology* 201(2), 266-276.

Suenaga, N. et al. (2004) "CD44 binding through the hemopexin-like domain is critical for its shedding by membrane-type 1 matrix metalloproteinase," *Oncogene* 24(5), 859-868.

Takahashi, M. et al. (2002) "Identification of membrane-type matrix metalloproteinase-1 as a target of the β-catenin/Tcf4 complex in human colorectal cancers," *Oncogene* 21(38), 5861-5867.

Takahra, T. et al. (2004) "Induction of myofibroblast MMP-9 transcription in three-dimensional collagen I gel cultures: regulation by NF-κB, AP-1 and Sp1," *International Journal of Biochemistry & Cell Biology* 36(2), 353-363.

Takino, T. (2004) "Membrane type 1 matrix metalloproteinase regulates collagen-dependent mitogen-activated protein/extracellular signal-related kinase activation and cell migration," *Cancer Research* 64(3), 1044-1049.

Tam, E. M. et al. (2002) "Collagen Binding Properties of the Membrane Type-1 Matrix Metalloproteinase (MT1-MMP) Hemopexin C Domain: The Ectodomain of the 44-kDa Autocatalytic Product of MT1-MMP Inhibits Cell Invasion by Disrupting Native Type I Collagen Cleavage," *Journal of Biological Chemistry* 277(41), 39005-39014.

Tam, J. P. et al. (1991) "Disulfide bond formation in peptides by dimethyl sulfoxide. Scope and applications," *Journal of the American Chemical Society* 113(17), 6657-6662.

Tan, C. et al. (2001) "Inhibition of integrin linked kinase (ILK) suppresses β-catenin-Lef/Tcf-dependent transcription and expression of the E-cadherin repressor, snail, in APC-/-human colon carcinoma cells," *Oncogene* 20(1), 133-140.

Temma, T. et al. (2009) "Development of a Radiolabeled Probe for Detecting Membrane Type-1 Matrix Metalloproteinase on Malignant Tumors," *Biological and Pharmaceutical Bulletin* 32(7), 1272-1277.

Thiery, J. P. (2002) "Epithelial-mesenchymal transitions in tumour progression," *Nature Reviews Cancer* 2(6), 442-454.

Thiery, J. P. (2003) "Epithelial-mesenchymal transitions in development and pathologies," *Current Opinion in Cell Biology* 15(6), 740-746.

Tien, D. (2005) "In vitro and in vivo characterization of a potential universal placebo designed for use in vaginal microbicide clinical trials," *AIDS Research and Human Retroviruses* 21(10), 845-853.

Toogood, P. L. (2002) "Inhibition of Protein—Protein Association by Small Molecules: Approaches and Progress," *Journal of Medicinal Chemistry* 45(8), 1543-1558.

(56) References Cited

OTHER PUBLICATIONS

Toole, B. P. (2004) "Hyaluronan: from extracellular glue to pericellular cue," *Nature Reviews Cancer 4*(7), 528-539.

Tsatas, D. (2002) "EGF receptor modifies cellular responses to hyaluronan in glioblastoma cell lines," *Journal of Clinical Neuroscience 9*(3), 282-288.

Turk, B. E. et al. (2004) "The structural basis for substrate and inhibitor selectivity of the anthrax lethal factor," *Nature Structural & Molecular Biology 11*(1), 60-66.

Udayakumar, T. S. et al. (2003) "Membrane Type-1 -Matrix Metalloproteinase Expressed by Prostate Carcinoma Cells Cleaves Human Laminin-5 β3 Chain and Induces Cell Migration," *Cancer Research 63*(9), 2292-2299.

Ueda, J. et al. (2003) "Sequence-specific silencing of MT1-MMP expression suppresses tumor cell migration and invasion: importance mportance of MT1-MMP as a therapeutic target for invasive tumors," *Oncogene 22*(54), 8716-8722.

Uekita, T. et al. (2001) "Cytoplasmic tail—dependent internalization of membrane-type 1 matrix metalloproteinase is important for its invasion-promoting activity," *Journal of Cell Biology 155*(7), 1345-1356.

Van Der Voort, R. et al. (1999) "Heparan Sulfate-modified CD44 Promotes Hepatocyte Growth Factor/Scatter Factor-induced Signal Transduction through the Receptor Tyrosine Kinase c-Met," *Journal of Biological Chemistry 274*(10), 6499-6506.

Vera, D. R. et al. (2002) "A Molecular CT Blood Pool Contrast Agent," *Academic Radiology 9*(7), 784-792.

Visser, G. W. M. et al. (1993) "Labeling of Monoclonal Antibodies with Rhenium-186 Using the MAG3 Chelate for Radioimmunotherapy of Cancer: A Technical Protocol," *Journal of Nuclear Medicine 34*(11), 1953-1963.

Vivinus-Nebot, M. et al. (2004) "Mature Human Thymocytes Migrate on Laminin-5 with Activation of Metalloproteinase-14 and Cleavage of CD44," *Journal of Immunology 172*(3), 1397-1406.

Voinea, M. (2002) "Designing of 'intelligent' liposomes for efficient delivery of drugs," *Journal of Cellular and Molecular Medicine 6*(4), 465-474.

Wang, P. et al. (2004) "The Hemopexin Domain of Membrane-type Matrix Metalloproteinase-1 (MT1-MMP) Is Not Required for Its Activation of proMMP2 on Cell Surface but Is Essential for MT1-MMP-mediated Invasion in Three-dimensional Type I Collagen," *Journal of Biological Chemistry 279*(49), 51148-51155.

Watkins, G. A. et al. (2009) "Development of an optimized activatable MMP-14 targeted SPECT imaging probe," *Bioorganic & Medicinal Chemistry 17*(2), 653-659.

Wolf, K. et al. (2003) "Compensation mechanism in tumor cell migration: mesenchymal—amoeboid transition after blocking of pericellular proteolysis," *Journal of Cell Biology 160*(2), 267-277.

Wozniak, M. A. et al. (2004) "Focal adhesion regulation of cell behavior," *Biochimica et Biophysica Acta (BBA)—Molecular Cell Research 1692*(2-3), 103-119.

Yang, J. et al. (2004) "Twist, a Master Regulator of Morphogenesis, Plays an Essential Role in Tumor Metastasis," *Cell 117*(7), 927-939.

Zhou, B. P. et al. (2004) "Dual regulation of Snail by GSK-3[beta]-mediated phosphorylation in control of epithelial-mesenchymal transition," *Nature Cell Biology 6*(10), 931-940.

Zimmer, S. et al. (1993) "Synthesis and backbone cyclization studies of hexapeptides using the reagents TBTU, HBTU, DPPA, and PPA," in *Peptides 1992 (Proceedings of the 22nd European Peptide Symposium)* (Schneider, C. H., et al., Eds.), pp. 393-394, ESCOM Science Publishers, Leiden, The Netherlands.

Zucker, S. (2003) "Membrane type-matrix metalloproteinases (MT-MMP)," *Current Topics in Developmental Biology 54*, 1-74.

Zucker, S. et al. (2000) "Critical appraisal of the use of matrix metalloproteinase inhibitors in cancer treatment," *Oncogene 19*(56), 6642-6650.

Zucker, S. et al. (2002) "Role of matrix metalloproteinases and plasminogen activators in cancer and metastasis. Therapeutic strategies," in *Anticancer Drug Development* (Baguley, B. C., et al., Eds.), pp. 91-122, Academic Press, San Diego, CA.

Zucker, S. et al. (2003) "Membrane Type Matrix Metalloproteinase," *Cell Surface Proteases 54*, 2-53.

Zucker, S. et al. (1998) "Tissue Inhibitor of Metalloproteinase-2 (TIMP-2) Binds to the Catalytic Domain of the Cell Surface Receptor, Membrane Type 1-Matrix Metalloproteinase 1 (MT1-MMP)," *Journal of Biological Chemistry 273*(2), 1216-1222.

Zucker, S. et al. (2001) "Tumorigenic Potential of Extracellular Matrix Metalloproteinase Inducer," *American Journal of Pathology 158*(6), 1921-1928.

\* cited by examiner

UPREGULATED MT1-MMP EXPRESSION IN HUMAN BREAST CANCER TISSUES

STRAND FOUR OF BLADE I AND IV ARE REQUIRED FOR FUNCTIONAL MT1-MMP

REQUIREMENT OF THE FOURTH STRAND OF BLADE I AND IV OF THE PEX DOMAIN OF MT1-MMP IN CELL MIGRATION

REQUIREMENT OF THE IVS4 OF MT1-MMP FOR CELL SURFACE LOCALIZATION

Similar results were also seen in IS4 mutations

STRUCTURE-BASED PEPTIDE DESIGN: TARGETING THE HEMOPEXIN
DOMAIN OF MT1-MMP

INHIBITION OF MIGRATION OF CANCER CELLS EXPRESSING ENDOGENOUS MT1-MMP BY IS4 PEPTIDES

INHIBITION OF MT1-MMP-INDUCED CANCER CELL MIGRATION/INVASION BY IS4 PEPTIDE

MATRIX METALLOPROTEINASE (MMP) FAMILY MEMBERS

Biological Function of MMPs

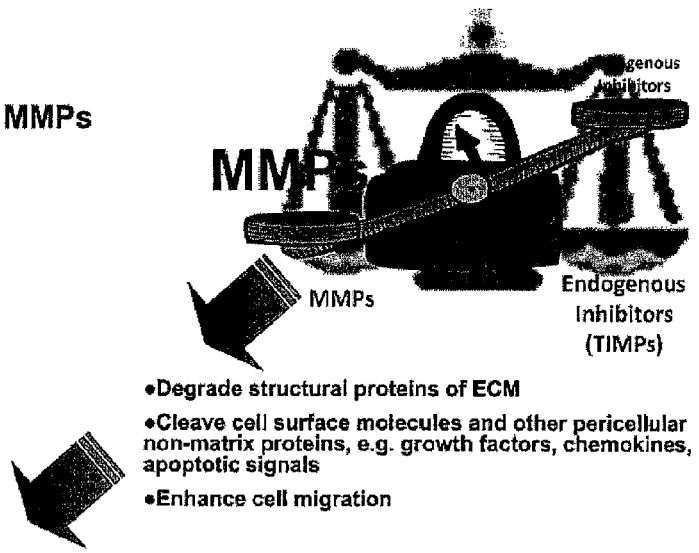

- Degrade structural proteins of ECM
- Cleave cell surface molecules and other pericellular non-matrix proteins, e.g. growth factors, chemokines, apoptotic signals
- Enhance cell migration

Physiologic processes: development, growth and involution

Pathologic processes: wound repair, Inflammatory diseases, tumor growth and metastasis

FIGURE 12

Endocytosis of cell surface MT1-MMP

ENHANCED CELL MIGRATION IN TRANSFECTED CELLS BY BLOCKING MT1-MMP ENDOCYTOSIS

MT1-MMP induces LNCaP Cell Scattering In 3d Type 1 Collagen Gels

Enhanced shedding of cell-cell adherin molecular E-cadherin by MT1-MMP in LNCaP cells Loss of E-cadherin expression in MT1-GFP prostate tumors MT1-MMP induces prostate cancer cell phenotypic changes Nonessential role of the cytoplasmic domain of MT1-MMP in cell migration Functional MT1-MMP is associated with phenotypic changes Requirement of MT1-MMP IS4 and IVS4 for hetero-dimer and homo-dimer formation Hypothetical model of MT1-MMP-induced EMT Structure based peptide design of a competitive inhibitor for MT1-MMP-enhanced cell migration Dose dependent inhibition of MT1-MMP-enhanced cell migration Specific inhibition of MT1-MMP-enhanced migration by IS4 peptides Evaluation of stable LNCaP cells expressing MT1-GFP chimeric cDNA: LNCaP cells transfected with MT1-GFP cDNA or GFP were selected with G418 and stable clones were isolated. The lysates of stable transfected and transiently transfected LNCaP cells were examined by Western blotting using anti-MT1-MMP antibodies.

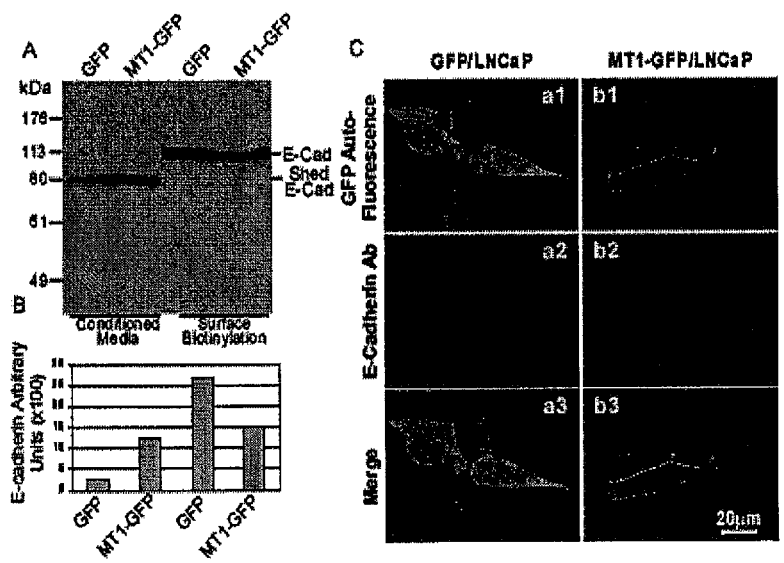

Shedding of cell surface E-cadherin by cells expressing MT1-GFP chimera: A) Examination of E-cadherin in the conditioned medium and cell surface. The conditioned medium was harvested from LNCaP cells expressing GFP or MT1-GFP and precipitated with TCA. The cell surface proteins were biotinylated and precipitated with Streptavdin beads. The conditioned medium and biotinylated cell surface proteins were immunoblotted with anti-Ecadherin antibody (extracellular domain). B) Densitometric analysis of E-cadherin in conditioned media and cell surface. C) LNCaP cells expressing GFP or MT1-GFP were labeled with anti-E-cadherin antibody and examined by confocal fluorescent microscopy. GFP and MT1-GFP expression in cells was identified based on green fluorescence (Green) and E-cadherin was seen as a Red. Co-localization was determined by merging both images.

FIGURE 29

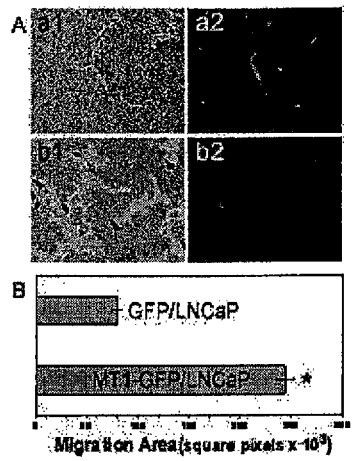

MT1-MMP enhances LNCaP cell migration: LNCaP cells expressing GFP and MT1-GFP chimeric cDNA were plated onto colloidal gold particle-coated coverslips for 18h. The cells were examined under both phase contrast (a1, b1)and fluorescent microscopy (a2, b2) in the same field. Cell migration was determined based on clearance of colloidal gold particle tracks. Stably transfected LNCaP cells were indicated as GFP-positive cells (A). The cell migratory ability was determined by analyzing cell migratory tracks using NIH imaging software. 10 fields of each group were analyzed. Expression of MT1-MMP in LNCaP cells significantly enhanced cell migration as compared to GFP-expressing LNCaP cells (*, P 0.01) (B).

FIGURE 30

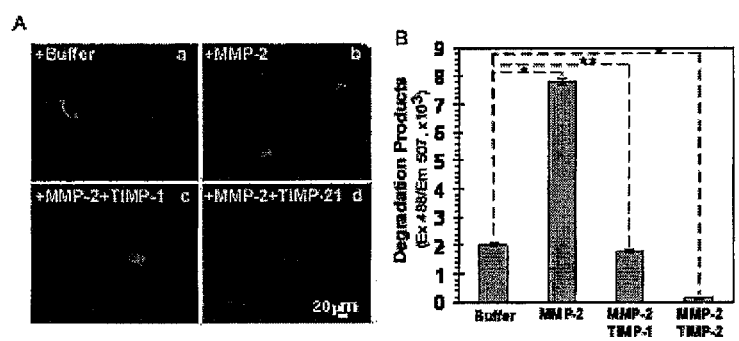

Digestion of FITC-labeled Matrigel by MT1-MMP expressing LNCaP cells: A) The MT1-GFP/LNCaP cells were plated onto FITC-Matrigel coverslips in the presence of recombinant MMP-2, MMP-2 and TIMP-1, or MMP-2 and TIMP-2. After 18 h incubation, the cells were examined under fluorescent microscopy. B) The degradation products of FITC-labeled Matrigel in the conditioned medium were collected and measured by FLEXStation using excitation wavelength at 488 nm and emission wavelength at 507 nm. The degradation products in MT1-MMP expressing cells were significantly increased in the presence of proMMP-2 and decreased in the presence of both proMMP-2 and TIMP-2 as compared to that of MT1-GFP expressing cells (*, P 0.001, ** P 0.05)

FIGURE 31

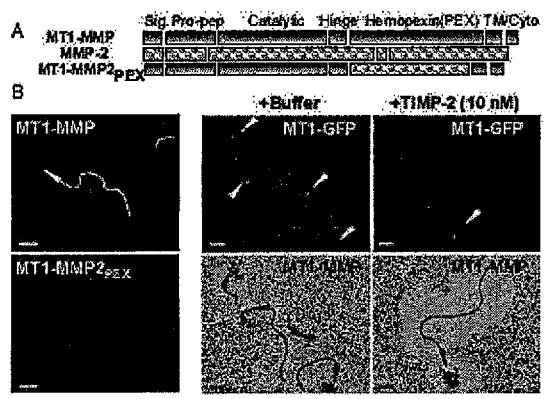

MT1-MMP-mediated cell migration is dependent on the PEX domain of MT1-MMP, but not enzymatic activity: A) Schematic diagram of wild-type and mutant MT1-MMPs. The PEX domain of MT1-MMP was replaced by that of MMP-2 to generated MT1-MMP2$_{PEX}$ chimaera. B) COS-1 cells transfected with MT1-MMP and MT1-MMP2$_{PEX}$ were plated onto FITC-labeled gelatin in serum-free medium for 18 h. Cell migration and substrate degradation were determined under fluorescent microscopy. C) No effect on MT1-MMP-mediated cell migration by inhibition of MT1-MMP enzymatic activity with TIMP-2. COS-1 cells expressing MT1-GFP chimeric cDNA were plated onto colloidal gold-coated FITC-labeled fibronectin coverslips in the absence and presence of recombinant TIMP-2 for 18 h in serum-free medium. The transfected cells were identified based on GFP expression as indicated by arrowheads. Arrows represent cell migration paths in both 6B and 6C. Bar: 20 μm.

FIGURE 32

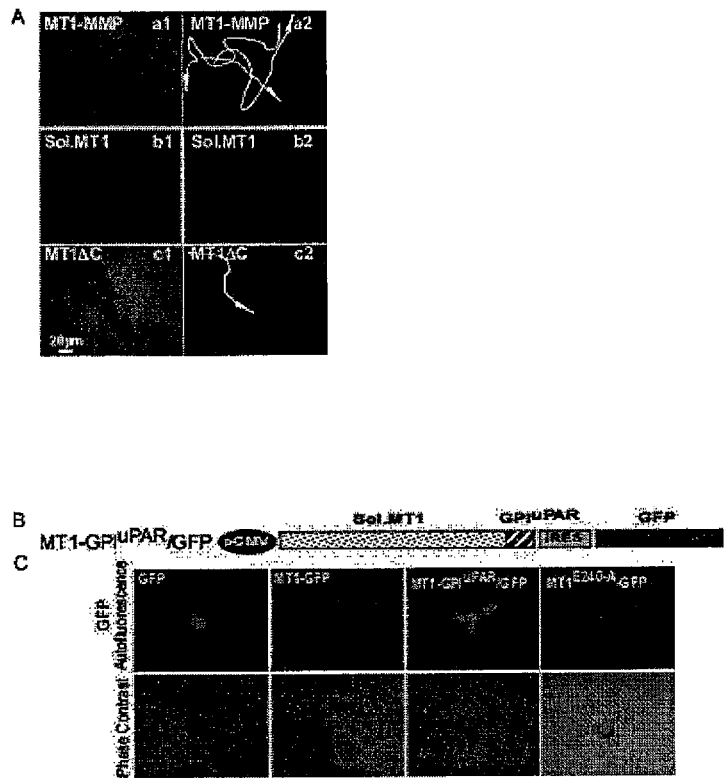

The cytoplasmic domain of MT1-MMP is not required for MT1-MMP-induced cell migration and scattering: A) Human breast cancer MDA-MB-231 cells transfected with wild-type and mutants of MT1-MMP as indicated were plated onto FITC-labeled fibronectin (a1 to c1) for 18 h followed by immunostaining with anti-MT1-MMP antibody (a2 to c2). MT1-MMP localization and cell migration were examined under fluorescent microscopy. Arrows indicate cell migration paths. B) Schematic diagram of MT1-GPI$^{uPAR}$/GFP construct: Mutant MT1-MMP lacking the transmembrane and cytoplasmic domains was amplified by a PCR and inserted into pIRES2/GFP vector (Clontech). C) Human prostate cancer LNCaP cells stably expressing GFP, MT1-GFP, MT1-GPI$^{uPAR}$/GFP, and MT1$^{E240-A}$-GFP cDNAs were cultured in type I collagen gels for 3 days followed by microscopic examination.

FIGURE 33

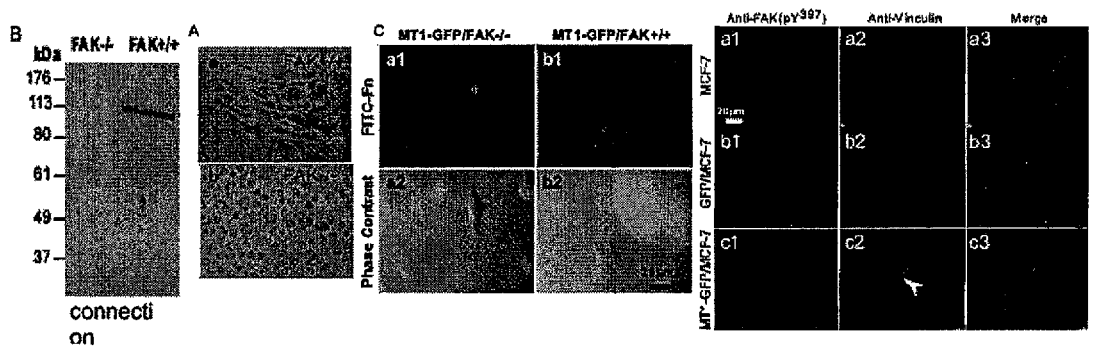

Expression of MT1-MMP in MCF-7 cells decreases the localization of vinculin in focal adhesion. A, B) FAK-/- cells were characterized by microscopic examination of cell morphology and by Western blotting using anti-FAK antibody. C) Change of FAK-/- fibroblast cell morphology and enhancement of cell migration by expressing MT1-GFP in cells. FAK-/- and FAK+/+ fibroblasts transfected with MT1-GFP were plated onto FITC-Fn for 18 h at 37°C. Cell migration was determined based on the loss of FITC-Fn. D) MCF-7 cells or MCF-7 cells stably expressing GFP or MT1-GFP were plated over human fibronectin (20 μg/ml)-coated coverslips for two days in the presence of 10% FCS followed by fixation and permeabilization. The cells were then incubated with anti-FAK (pY397) and anti-Vinculin antibodies followed by secondary antibodies. The localization of vinculin (green) and pFAK (red) was visualized under fluorescent microscopy. The arrowhead indicates relocation of MT1-GFP chimera (green) to cell-cell junction area (also see Fig. 3}b1).

FIGURE 35

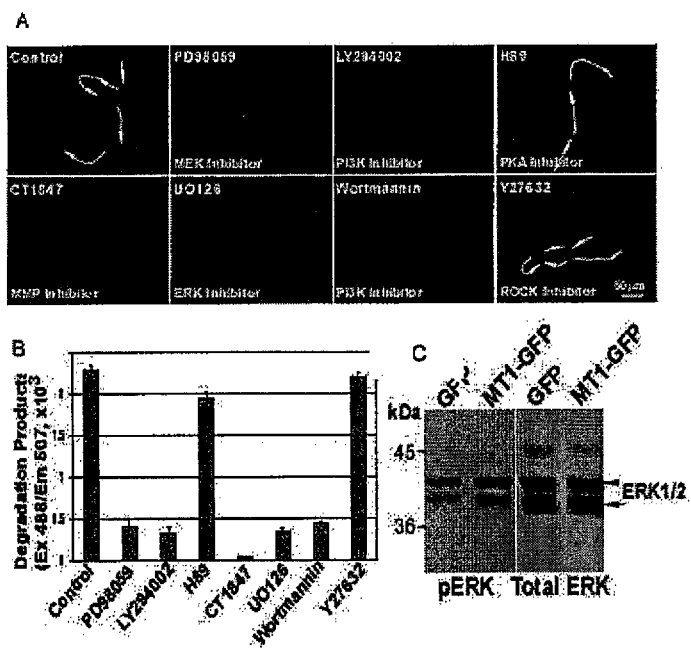

Exploration of the signaling pathways in MT1-MMP mediated prostate cell migration: Stable LNCaP cells expressing MT1-GFP chimera were plated on FITC-labeled fibronectin-coated coverslips with 10% FCS media for 60 min. The serum containing media were then replaced by serum-free media in the presence of various inhibitors (20μm PD98059; 20 μm UO126; 20 μm LY294002; 0.1μm Wortmannin; 0.1μm H89; 10 μmY27632, and 0.1μm CT1847) for 18 h at 37°C followed by microscopic examination. Determination of cell migration was based on the tracks of loss of FITC-fibronectin (A). The conditioned medium was collected and FITC-fibronectin degradation products were measured by Benchtop Scanning Fluorometer (FlexStation) to quantitate the inhibitory effect on MT1-MMP-mediated cell migration by inhibitors (B). 10 mg cell lysates were analyzed by Western blotting using anti-phosphorylated ERK1/2 (pERK1/2) antibodies. pERK1/2 was detected by ECL kit. The membrane was stripped and reprobed with total ERK1/2 antibodies (C).

FIGURE 36

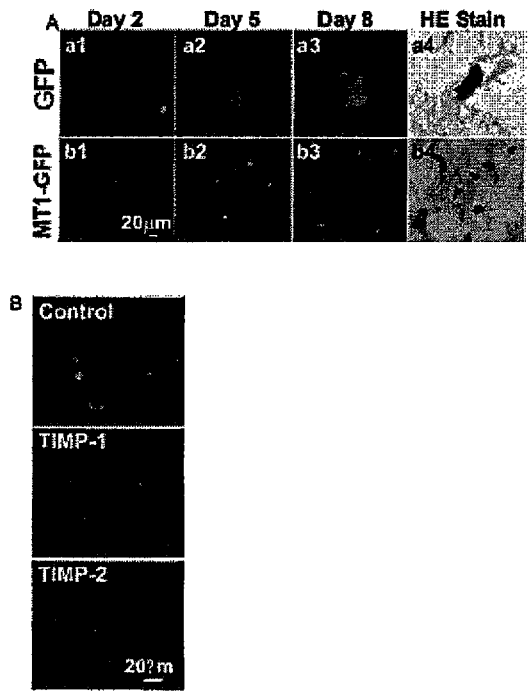

MT1-MMP induced LNCaP cell phenotypic change in type I collagen gels: A) LNCaP cells expressing GFP or MT1-GFP (4x10⁴/ml) were mixed with type I collagen gels (2.5mg/ml). The cells were examined daily under fluorescent microscopy. At day 8, the gels were fixed and frozen sections were obtained for HE staining. B) LNCaP cells expressing MT1-GFP chimera were cultured in 3D type 1 collagen gels in the absence or presence of recombinant TIMP-1 or TIMP-2 for 8 days. Cell phenotypic change was examined under fluorescent microscopy.

FIGURE 37

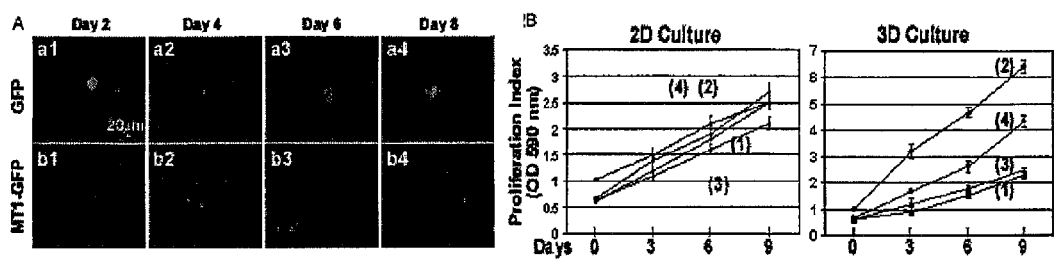

MT1-MMP promotes LNCaP and MCF-7 cell scattering and proliferation in a 3D culture model: LNCaP and MCF-7 cells (4x10⁴/ml) stably transfected with GFP or MT1-GFP were mixed with type I collagen gels (3D) or seeded on type I collagen-coated plates (2D). MCF-7 cell scattering was examined daily (A) and cell proliferation was determined by a MTT assay (B). (1) GFP/MCF-7; (2) MT1-GFP/MCF-7; (3) GFP/LNCaP; and (4) MT1-GFP/LNCaP.

FIGURE 38

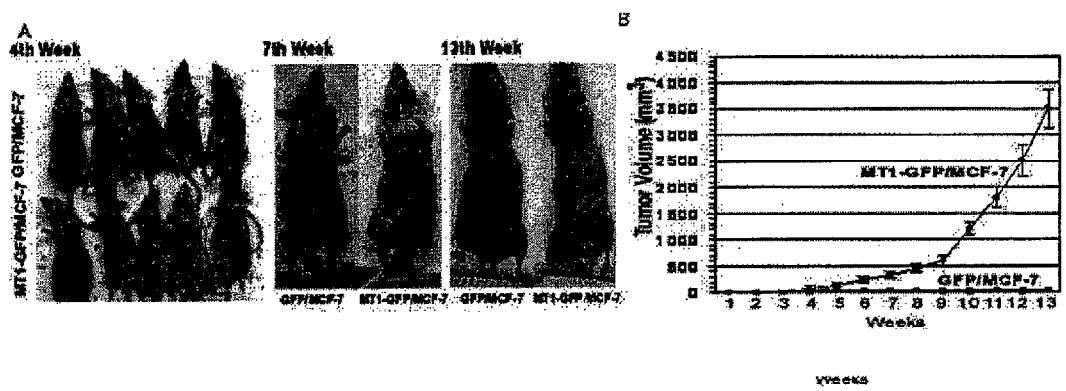

MT1-MMP promotes tumorigenicity of breast carcinoma MCF7 cells: $5 \times 10^6$ MCF-7 cells stably transfected with GFP control and MT1-GFP cDNAs were orthotopically injected in the mammary fat pad of 4-5-week-old immunodeficient female mice (A). Arrowheads represent visible tumor mass. Tumor size was measured once a week. Both GFP and MT1-GFP expressing MCF-7 tumors became visible after the 3rd week. GFP expressing tumors entered a growth arrest phase, whereas MT1-GFP expressing tumors grew rapidly (B).

FIGURE 39

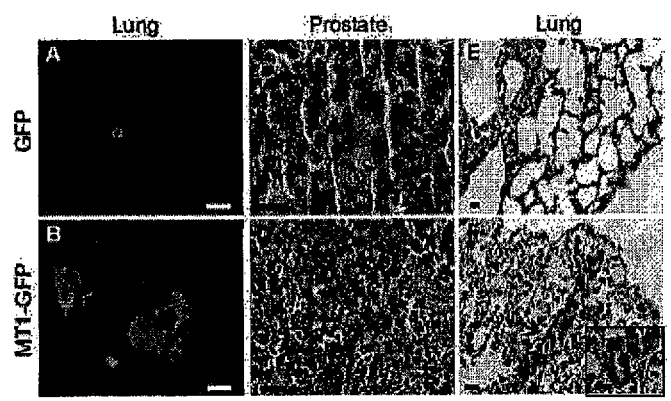

MT1-MMP enhanced prostate cancer invasion and metastias: GFP/LNCaP and MT1-GFP/LNCaP cells were orthotopically injected into the mouse dorsal prostate. 12 weeks later, the mice were sacrificed. The metastatic cells in the lungs were examined based on GFP autofluorescence (A & B) or HE staining for primary tumors in prostate (C & D), and lungs (E & F). Arrow represents metastatic cells. (Bar: 20 μm)

FIGURE 40

MT1-MMP forms a complex with CD44H: COS-1 cells transfected with various cDNAs as indicated were lysed and immunoprecipitated (IP) with corresponding antibodies followed by Western blotting using antibodies as indicated (WB).

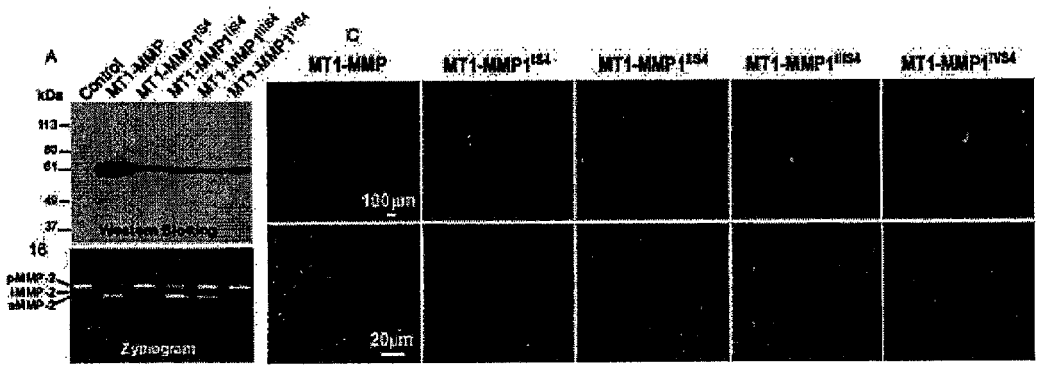

Strand four of blades I and IV are required for MT1-MMP-mediated proMMP-2 activation and cell migration, but not substrate degradation: A) The outer strand four of each blade of MT1-MMP PEX domain was replaced by the corresponding region of MMP-1 to generate MT1-MMP1 chimeras. Western blotting of COS-1 cells transfected with various cDNAs as indicated was performed using anti-MT1-MMP catalytic domain antibody. B) The conditioned medium of COS-1 cells transfected with various cDNAs as indicated was examined by gelatin zymography. "p": latent (pro), "i": intermediated, and "a": activated forms. C) Cell migration and substrate degradation were examined by plating transfected COS-1 cells onto FITC-gelatin coverslips and microscopic examination was performed under low power (40x) and high power (200x).

FIGURE 4Z

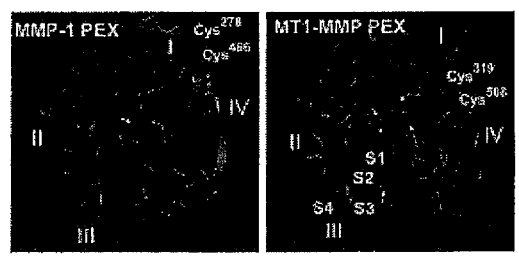

Similarity of the PEX domain structures of MMP-1 and MT1-MMP: The chain of the PEX domain of MMPs is organized in four β-sheets (bladed propeller) labeled I to IV. Each blade is made up of four antiparallel β-stands connected in a W-like strand topology (e.g. blade III of MT1-MMP PEX domain numbered S1-red, S2-green, S3-yellow and S4-pink from innermost S1 to outermost S4). MMP1 PDB entry: 1FBL. MT1-MMP: computational model.

FIGURE 43

| Native MT1-MMP PEX Sequence | IS4 346 NQVMDGYPMPIGQF... | IIS4 392 KASLEPGYPKHIKKL... | IIIS4 450 RRLRAVDSEYPKNIKY... | IVS4 488 NQKLKVEPGYPKSALRDWMG | Substrate Degradation | ProMMP-2 Activation | Cell Migration |
|---|---|---|---|---|---|---|---|
| Mutant Tested | | | | | | | |
| MT1-MMP1 Blade I | MMP-1 (IS1+IS2+IS3+IS4) | | | | + | − | − |
| MT1-MMP1 Blade II | | MMP-1 (IIS1+IIS2+IIS3+IIS4) | | | + | + | + |
| MT1-MMP1 Blade III | | | MMP-1 (IIIS1+IIIS2+IIIS3+IIIS4) | | + | + | + |
| MT1-MMP1 Blade IV | | | | MMP-1 (IVS1+IVS2+IVS3+IVS4) | + | − | − |
| MT1-MMP1 IS4 | SFYPKVELMFISVF | | | | + | − | − |
| MT1-MMP1 IIS4 | | GQDVLYGYPKDIHRS | | | + | + | + |
| MT1-MMP1 IIIS4 | | | EYKQSMDTGYPKMIAR | | + | + | + |
| MT1-MMP1 IVS4 | | | | QFDFKTKRILZLQKANGWFN | + | − | − |
| Mutant Proposed | | | | | | | |
| MT1-MMP1 IS4L1 | SFYPKV | | | | | | |
| MT1-MMP1 IS4β | ELMF | | | | | | |
| MT1-MMP1 IS4L2 | ISVF | | | | | | |
| MT1-MMP1 IVS4L1 | | | | QFDFKTK | | | |
| MT1-MMP1 IVS4β | | | | RILTLQK | | | |
| MT1-MMP1 IVS4L2 | | | | ANSWFN | | | |
| Alternative Mutants Proposed | | | | | | | |
| MT1-MMP1 IS4L1β | YPKVEL | | | | | | |
| MT1-MMP1 IS4βL2 | MFISVF | | | | | | |
| MT1-MMP1 IVS4L1β | | | | TKRILT | | | |
| MT1-MMP1 IVS4βL2 | | | | LQKANS | | | |

The amino acid sequences of the fourth strand of blades I to IV are listed in the top line. Red colored residues represent loops flanking the β-strand of the fourth strand and black colored residues represent β-strand within the fourth strand. The regions within the MT1-MMP PEX domain are replaced by the corresponding residues of MMP-1 (minimum homology noted). The results from tested mutants are listed as "−" for negative and "+" for positive. Proposed new substituted mutations with MMP-1 in IS4 and IVS4 loops (pink color) and β-strands (blue color).

FIGURE 44

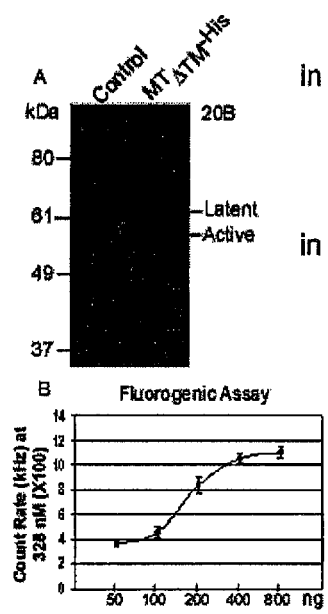

Purification of recombinant soluble MT1-MMP: A) MTΔTM-His chimeric cDNA lacking the transmembrane and cytoplasmic domains of MT1-MMP was generated by a PCR approach and the fusion protein was purified from the conditioned medium of transfected COS-1 cells using a histidine binding resin (Novagen). The protein bound to beads was analyzed by Western blotting using the anti-MT1-MMP antibody. Both latent and active soluble form of MT1-MMP were detected by Western blot. Approximate 2.25 mg/liter of the recombinant MTΔTM-His were obtained from the conditioned mediums based on BCA Protein Assay kit (Pierce). B) Purified soluble MT1-MMP was incubated with a fluorogenic substrate (Mac-Pro-Leu-GLy-Leu-Dpa-Ala-Arg-NH2) (Bachem) for 60 min at 37°C followed by a laser detection of cleaved fluorescent particles using Olympus MF20 (Single-Molecule Fluorescence Detection System) at 328 nm waive length for excitation. MTΔTM/His cleaves fluorogenic substrate in a dose dependent manner.

FIGURE 45

Strategy for development of non catalytic peptide inhibitors for MT1-MMP. A working chart for designing and characterizing inhibitory peptides targeting the PEX domain of MT1-MMP.

Homo sapiens MT1-MMP, matrix metallopeptidase 14 (membrane-inserted) (MMP14), (NCBI Reference Sequence: NM_004995.2

(a) amino acid sequence

MSPAPRPPRCLLLPLLTLGTALASLGSAQSSSFSPEAWLQQYGY
LPPGDLRTHTQRSPQSLSAAIAAMQKFYGLQVTGKADADTMKAMRRPRCGVPDKFGAE
IKANVRRKRYAIQGLKWQHNEITFCIQNYTPKVGEYATYEAIRKAFRVWESATPLRFR
EVPYAYIREGHEKQADIMIFFAEGFHGDSTPFDGEGGFLAHAYFPGPNIGGDTHFDSA
EPWTVRNEDLNGNDIFLVAVHELGHALGLEHSSDPSAIMAPFYQWMDTENFVLPDDDR
RGIQQLYGGESGFPTKMPPQPRTTSRPSVPDKPKNPTYGPNICDGNFDTVAMLRGEMF
VFKERWFWRVRNNQVMDGYPMPIGQFWRGLPASINTAYERKDGKFVFFKGDKHWVFDE
ASLEPGYPKHIKELGRGLPTDKIDAALFWMPNGKTYFFRGNKYYRFNEELRAVDSEYP
KNIKVWEGIPESPRGSFMGSDEVFTYFYKGNKYWKFNNQKLKVEPGYPKSALRDWMGC
PSGGRPDEGTEEETEVIIEVDEEGGGAVSAAAVVLPVLLLLLVLAVGLAVFFFRRHG
TPRRLLYCQRSLLDKV (b) nucleotide sequence

```
   1 cagaccccag ttcgccgact aagcagaaga aagatcaaaa accggaaaag aggagaagag
  61 caaacaggca ctttgaggaa caatcccctt taactccaag ccgacagcgg tctaggaatt
 121 caagttcagt gcctaccgaa gacaaaggcg ccccgaggga gtggcggtgc gacccaggg
 181 cgtgggcccg gccgcggagc ccacactgcc cggctgaccc ggtggtctcg gaccatgtct
 241 cccgcccaa gaccccccg ttgtctcctg ctcccctgc tcacgctcgg caccgcgctc
 301 gcctccctcg gctcggccca aagcagcagc ttcagcccg aagcctggct acagcaatat
 361 ggctacctgc ctccggggga cctacgtacc cacacacagc gtcacccca gtcactctca
 421 gcggccatcg ctgccatgca gaagttttac ggcttgcaag taacaggcaa agctgatgca
 481 gacaccatga aggccatgag gcgcccccga tgtggtgttc cagacaagtt tggggctgag
 541 atcaaggcca atgttcgaag gaagcgctac gccatccagg gtctcaaatg gcaacataat
 601 gaaatcactt tctgcatcca gaattacacc cccaaggtgg gcgagtatgc cacatacgag
 661 gccattcgca aggcgttccg cgtgtgggag agtgccacac cactgcgctt ccgcgaggtg
 721 ccctatgcct acatccgtga gggccatgag aagcaggccg acatcatgat cttctttgcc
 781 gagggcttcc atggcgacag cacgcccttc gatggtgagg gcggcttcct ggcccatgcc
 841 tacttcccag gccccaacat tggaggagac acccactttg actctgccga gccttggact
 901 gtcaggaatg aggatctgaa tggaaatgac atcttcctgg tgctgtgca cgagctgggc
 961 catgccctgg ggctcgagca ttccagtgac cctcggcca tcatgcacc cttttaccag
1021 tggatggaca cggagaattt tgtgctgccc gatgatgacc gccggggcat ccagcaactt
1081 tatgggggtg agtcagggtt cccaccaag atgcccctc aacccaggac tacctccgg
1141 ccttctgttc ctgataaacc caaaaacccc acctatgggc caacatctg tgacgggaac
1201 tttgacaccg tggccatgct ccgaggggag atgtttgtct tcaaggagcg ctggttctgg
1261 cgggtgagga taaccaagt gatggatgga taccaatgc ccattggcca gttctggcgg
1321 ggcctgcctg cgtccatcaa cactgcctac gagaggaagg atggcaaatt cgtcttcttc
1381 aaaggagaca agcattgggt gtttgatgag gcgtccctgg aacctggcta ccccaagcac
1441 attaaggagc tgggccgagg gctgcctacc gacaagattg atgctgctct cttctggatg
1501 cccaatggaa agacctactt cttccgtgga aacaagtact accgtttcaa cgaagagctc
1561 aggcagtgg atagcgagta ccccaagaac atcaaagtct gggaagggat ccctgagtct
1621 cccagagggt cattcatggg cagcgatgaa gtcttcactt acttctacaa ggggaacaaa
1681 tactggaaat tcaacaacca gaagctgaag gtagaaccgg gctaccccaa gtcagccctg
1741 agggactgga tgggctgccc atcggggaggc cggccggatg aggggactga ggaggagacg
```

```
1801 gaggtgatca tcattgaggt ggacgaggag ggcggcgggg cggtgagcgc ggctgccgtg
1861 gtgctgcccg tgctgctgct gctcctggtg ctggcggtgg gccttgcagt cttcttcttc
1921 agacgccatg ggacccccag gcgactgctc tactgccagc gttccctgct ggacaaggtc
1981 tgacgccac cgccggcccg cccactccta ccacaaggac tttgcctctg aaggccagtg
2041 gcagcaggtg gtggtgggtg ggctgctccc atcgtcccga gcccctccc cgcagcctcc
2101 ttgcttctct ctgtccctg gtggcctcc ttcaccctga ccgctccct ccctcctgcc
2161 ccggcattgc atcttccta gataggtccc ctgagggctg agtgggaggg cggccctttc
2221 cagcctctgc ccctcagggg aaccctgtag ctttgtgtct gtccagcccc atctgaatgt
2281 gttggggggct ctgcacttga aggcaggacc ctcagacctc gctggtaaag gtcaaatggg
2341 gtcatctgct cctttccat cccctgacat accttaacct ctgaactctg acctcaggag
2401 gctctgggca ctccagccct gaaagcccca ggtgtaccca attggcagcc tctcactact
2461 ctttctggct aaaaggaatc taatcttgtt gagggtagag accctgagac agtgtgaggg
2521 ggtggggact gccaagccac cctaagacct tgggaggaaa actcagagag ggtcttcgtt
2581 gctcagtcag tcaagttcct cggagatctg cctctgcctc acctacccca gggaacttcc
2641 aaggaaggag cctgagccac tggggactaa gtgggcagaa gaaacccttg gcagccctgt
2701 gcctctcgaa tgttagcctt ggatgggct ttcacagtta gaagagctga accagggt
2761 gcagctgtca ggtagggtgg ggccggtggg agaggcccgg gtcagagccc tgggggtgag
2821 cctgaaggcc acagagaaag aaccttgccc aaactcaggc agctggggct gaggcccaaa
2881 ggcagaacag ccagaggggg caggagggga ccaaaaagga aaatgaggac gtgcagcagc
2941 attggaaggc tggggcgggg caggccaggc caagccaagc aggggccac agggtgggct
3001 gtggagctct caggaagggc cctgaggaag gcacacttgc tcctgttggt ccctgtcctt
3061 gctgcccagg cagcgtggag gggaagggta gggcagccag agaaaggagc agagaaggca
3121 cacaaacgag gaatgagggg cttacgaga ggccacaggg cctggctggc cacgctgtcc
3181 cggcctgctc accatctcag tgaggggcag gagctggggc tcgcttaggc tgggtccacg
3241 cttccctggt gccagcaccc ctcaagcctg tctcaccagt ggcctgccct ctcgctcccc
3301 cacccagccc accattgaa gtctccttgg gccaccaaag gtggtggcca tggtaccggg
3361 gacttgggag agtgagaccc agtggaggga gcaagaggag agggatgtcg ggggggtggg
3421 gcacggggta ggggaaatgg ggtgaacggt gctggcagtt cggctagatt tctgtcttgt
3481 ttgtttttttt gttttgttta atgtatattt ttattataat tattatatat gaattccaaa
3541 aaaaaaaaaa aaaaaaa
```

FIG 47 (CONT)

SEQUENCE LISTING

```
<160> NUMBER OF SEQ ID NOS: 38

<210> SEQ ID NO 1
<211> LENGTH: 8
<212> TYPE: PRT
<213> ORGANISM: Homo sapiens

<400> SEQUENCE: 1

Val Met Asp Gly Tyr Pro Met Pro
1               5

<210> SEQ ID NO 2
<211> LENGTH: 8
<212> TYPE: PRT
<213> ORGANISM: Homo sapiens

<400> SEQUENCE: 2

Phe Asp Glu Ala Ser Leu Glu Pro
1               5

<210> SEQ ID NO 3
<211> LENGTH: 8
<212> TYPE: PRT
<213> ORGANISM: Homo sapiens

<400> SEQUENCE: 3

Gly Tyr Pro Lys Ser Ala Leu Arg
1               5

<210> SEQ ID NO 4
<211> LENGTH: 5
<212> TYPE: PRT
<213> ORGANISM: Homo sapiens

<400> SEQUENCE: 4

Gly Tyr Pro Met Pro
1               5

<210> SEQ ID NO 5
<211> LENGTH: 8
<212> TYPE: PRT
<213> ORGANISM: Homo sapiens

<400> SEQUENCE: 5

Tyr Pro Glu Val Glu Leu Asn Phe
1               5
```

```
<210> SEQ ID NO 6
<211> LENGTH: 7
<212> TYPE: PRT
<213> ORGANISM: Homo sapiens

<400> SEQUENCE: 6

Lys Pro Met Gly Pro Leu Leu
1               5

<210> SEQ ID NO 7
<211> LENGTH: 8
<212> TYPE: PRT
<213> ORGANISM: Homo sapiens

<400> SEQUENCE: 7

Lys Leu Glu Pro Glu Leu His Leu
1               5

<210> SEQ ID NO 8
<211> LENGTH: 8
<212> TYPE: PRT
<213> ORGANISM: Homo sapiens

<400> SEQUENCE: 8

Leu Gln Arg Val Glu Met Asn Phe
1               5

<210> SEQ ID NO 9
<211> LENGTH: 8
<212> TYPE: PRT
<213> ORGANISM: Homo sapiens

<400> SEQUENCE: 9

Ser Arg Pro Gln Gly Pro Phe Leu
1               5

<210> SEQ ID NO 10
<211> LENGTH: 8
<212> TYPE: PRT
<213> ORGANISM: Homo sapiens

<400> SEQUENCE: 10

Asn Pro Glu Pro Glu Phe His Leu
1               5

<210> SEQ ID NO 11
<211> LENGTH: 8
<212> TYPE: PRT
<213> ORGANISM: Homo sapiens

<400> SEQUENCE: 11

Leu Gln Pro Gly Tyr Pro Ala Leu
1               5

<210> SEQ ID NO 12
<211> LENGTH: 8
<212> TYPE: PRT
<213> ORGANISM: Homo sapiens

<400> SEQUENCE: 12

Arg Pro Lys Thr Ser Val Asn Leu
1               5

<210> SEQ ID NO 13
```

```
<211> LENGTH: 8
<212> TYPE: PRT
<213> ORGANISM: Homo sapiens

<400> SEQUENCE: 13

Gln Val Asp Ala Glu Leu Phe Leu
1               5

<210> SEQ ID NO 14
<211> LENGTH: 8
<212> TYPE: PRT
<213> ORGANISM: Homo sapiens

<400> SEQUENCE: 14

Val Leu Asp Asn Tyr Pro Met Pro
1               5

<210> SEQ ID NO 15
<211> LENGTH: 8
<212> TYPE: PRT
<213> ORGANISM: Homo sapiens

<400> SEQUENCE: 15

Val Met Asp Gly Tyr Pro Met Gln
1               5

<210> SEQ ID NO 16
<211> LENGTH: 8
<212> TYPE: PRT
<213> ORGANISM: Homo sapiens

<400> SEQUENCE: 16

Leu Val Ser Leu Gln Pro Ala Gln
1               5

<210> SEQ ID NO 17
<211> LENGTH: 8
<212> TYPE: PRT
<213> ORGANISM: Homo sapiens

<400> SEQUENCE: 17

Leu Val Ser Pro Arg Pro Ala Arg
1               5

<210> SEQ ID NO 18
<211> LENGTH: 5
<212> TYPE: PRT
<213> ORGANISM: Homo sapiens

<400> SEQUENCE: 18

Gly Pro Leu Phe Arg
1               5

<210> SEQ ID NO 19

<400> SEQUENCE: 19

000

<210> SEQ ID NO 20
<211> LENGTH: 6
<212> TYPE: PRT
<213> ORGANISM: Homo sapiens

<400> SEQUENCE: 20
```

Leu Gln Lys Ala Asn Ser
1               5

<210> SEQ ID NO 21
<211> LENGTH: 5
<212> TYPE: PRT
<213> ORGANISM: Homo sapiens

<400> SEQUENCE: 21

Leu Lys Ser Val Lys
1               5

<210> SEQ ID NO 22
<211> LENGTH: 6
<212> TYPE: PRT
<213> ORGANISM: Homo sapiens

<400> SEQUENCE: 22

Thr Leu Lys Ser Asn Ser
1               5

<210> SEQ ID NO 23
<211> LENGTH: 6
<212> TYPE: PRT
<213> ORGANISM: Homo sapiens

<400> SEQUENCE: 23

Val Ala Arg Gly Asn Lys
1               5

<210> SEQ ID NO 24
<211> LENGTH: 8
<212> TYPE: PRT
<213> ORGANISM: Homo sapiens

<400> SEQUENCE: 24

Asn Gln Val Asp Gln Val Gly Tyr
1               5

<210> SEQ ID NO 25
<211> LENGTH: 6
<212> TYPE: PRT
<213> ORGANISM: Homo sapiens

<400> SEQUENCE: 25

Ile Leu Lys Ser Asn Ser
1               5

<210> SEQ ID NO 26
<211> LENGTH: 8
<212> TYPE: PRT
<213> ORGANISM: Homo sapiens

<400> SEQUENCE: 26

Gly Phe Pro Arg Leu Val Gly Pro
1               5

<210> SEQ ID NO 27
<211> LENGTH: 6
<212> TYPE: PRT
<213> ORGANISM: Homo sapiens

<400> SEQUENCE: 27

Thr Leu Lys Ser Asn Ser
1               5

<210> SEQ ID NO 28
<211> LENGTH: 6
<212> TYPE: PRT
<213> ORGANISM: Homo sapiens

<400> SEQUENCE: 28

Val Met Pro Ala Asn Ser
1               5

<210> SEQ ID NO 29
<211> LENGTH: 8
<212> TYPE: PRT
<213> ORGANISM: Homo sapiens

<400> SEQUENCE: 29

Gly Tyr Pro Lys Ser Ile Leu Arg
1               5

<210> SEQ ID NO 30
<211> LENGTH: 8
<212> TYPE: PRT
<213> ORGANISM: Homo sapiens

<400> SEQUENCE: 30

Gly His Pro Arg Ser Ile Leu Lys
1               5

<210> SEQ ID NO 31
<211> LENGTH: 8
<212> TYPE: PRT
<213> ORGANISM: Homo sapiens

<400> SEQUENCE: 31

Gly Tyr Pro Gln Ser Thr Ala Arg
1               5

<210> SEQ ID NO 32
<211> LENGTH: 8
<212> TYPE: PRT
<213> ORGANISM: Homo sapiens

<400> SEQUENCE: 32

Asp Ala Pro Gln Pro Met Gly Pro
1               5

<210> SEQ ID NO 33
<211> LENGTH: 8
<212> TYPE: PRT
<213> ORGANISM: Homo sapiens

<400> SEQUENCE: 33

Gly Tyr Pro Arg Asn Ile Ser His
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: The residue in this position is cysteine.

```
<400> SEQUENCE: 34

Pro Arg Cys Gly Xaa Pro Asp
1               5

<210> SEQ ID NO 35
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: The residue in this position is histidine.
<220> FEATURE:
<221> NAME/KEY: MISC_FEATURE
<222> LOCATION: (6)..(7)
<223> OTHER INFORMATION: The residue in this position is histidine.
<220> FEATURE:
<221> NAME/KEY: MISC_FEATURE
<222> LOCATION: (9)..(10)
<223> OTHER INFORMATION: The residue in this position is histidine.

<400> SEQUENCE: 35

His Glu Xaa Xaa His Xaa Xaa Gly Xaa Xaa His
1               5                   10

<210> SEQ ID NO 36
<211> LENGTH: 582
<212> TYPE: PRT
<213> ORGANISM: Homo sapiens

<400> SEQUENCE: 36

Met Ser Pro Ala Pro Arg Pro Pro Arg Cys Leu Leu Leu Pro Leu Leu
1               5                   10                  15

Thr Leu Gly Thr Ala Leu Ala Ser Leu Gly Ser Ala Gln Ser Ser Ser
            20                  25                  30

Phe Ser Pro Glu Ala Trp Leu Gln Gln Tyr Gly Tyr Leu Pro Pro Gly
        35                  40                  45

Asp Leu Arg Thr His Thr Gln Arg Ser Pro Gln Ser Leu Ser Ala Ala
    50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Gly His Glu Lys Gln Ala Asp
                165                 170                 175

Ile Met Ile Phe Phe Ala Glu Gly Phe His Gly Asp Ser Thr Pro Phe
            180                 185                 190

Asp Gly Glu Gly Gly Phe Leu Ala His Ala Tyr Phe Pro Gly Pro Asn
        195                 200                 205

Ile Gly Gly Asp Thr His Phe Asp Ser Ala Glu Pro Trp Thr Val Arg
    210                 215                 220
```

Asn Glu Asp Leu Asn Gly Asn Asp Ile Phe Leu Val Ala Val His Glu
225                 230                 235                 240

Leu Gly His Ala Leu Gly Leu Glu His Ser Ser Asp Pro Ser Ala Ile
            245                 250                 255

Met Ala Pro Phe Tyr Gln Trp Met Asp Thr Glu Asn Phe Val Leu Pro
        260                 265                 270

Asp Asp Arg Arg Gly Ile Gln Gln Leu Tyr Gly Gly Glu Ser Gly
    275                 280                 285

Phe Pro Thr Lys Met Pro Pro Gln Pro Arg Thr Thr Ser Arg Pro Ser
    290                 295                 300

Val Pro Asp Lys Pro Lys Asn Pro Thr Tyr Gly Pro Asn Ile Cys Asp
305                 310                 315                 320

Gly Asn Phe Asp Thr Val Ala Met Leu Arg Gly Glu Met Phe Val Phe
                325                 330                 335

Lys Glu Arg Trp Phe Trp Arg Val Arg Asn Asn Gln Val Met Asp Gly
            340                 345                 350

Tyr Pro Met Pro Ile Gly Gln Phe Trp Arg Gly Leu Pro Ala Ser Ile
        355                 360                 365

Asn Thr Ala Tyr Glu Arg Lys Asp Gly Lys Phe Val Phe Phe Lys Gly
    370                 375                 380

Asp Lys His Trp Val Phe Asp Glu Ala Ser Leu Glu Pro Gly Tyr Pro
385                 390                 395                 400

Lys His Ile Lys Glu Leu Gly Arg Gly Leu Pro Thr Asp Lys Ile Asp
                405                 410                 415

Ala Ala Leu Phe Trp Met Pro Asn Gly Lys Thr Tyr Phe Phe Arg Gly
            420                 425                 430

Asn Lys Tyr Tyr Arg Phe Asn Glu Glu Leu Arg Ala Val Asp Ser Glu
        435                 440                 445

Tyr Pro Lys Asn Ile Lys Val Trp Glu Gly Ile Pro Glu Ser Pro Arg
    450                 455                 460

Gly Ser Phe Met Gly Ser Asp Glu Val Phe Thr Tyr Phe Tyr Lys Gly
465                 470                 475                 480

Asn Lys Tyr Trp Lys Phe Asn Asn Gln Lys Leu Lys Val Glu Pro Gly
                485                 490                 495

Tyr Pro Lys Ser Ala Leu Arg Asp Trp Met Gly Cys Pro Ser Gly Gly
            500                 505                 510

Arg Pro Asp Glu Gly Thr Glu Glu Thr Glu Val Ile Ile Ile Glu
        515                 520                 525

Val Asp Glu Glu Gly Gly Ala Val Ser Ala Ala Ala Val Val Leu
    530                 535                 540

Pro Val Leu Leu Leu Leu Leu Val Leu Ala Val Gly Leu Ala Val Phe
545                 550                 555                 560

Phe Phe Arg Arg His Gly Thr Pro Arg Arg Leu Leu Tyr Cys Gln Arg
                565                 570                 575

Ser Leu Leu Asp Lys Val
            580

<210> SEQ ID NO 37
<211> LENGTH: 3558
<212> TYPE: DNA
<213> ORGANISM: Homo sapiens

<400> SEQUENCE: 37
cagaccccag ttcgccgact aagcagaaga aagatcaaaa accggaaaag aggagaagag    60

```
caaacaggca ctttgaggaa caatcccctt taactccaag ccgacagcgg tctaggaatt      120
caagttcagt gcctaccgaa gacaaaggcg ccccgaggga gtggcggtgc gaccccaggg      180
cgtgggcccg gccgcggagc ccacactgcc cggctgaccc ggtggtctcg gaccatgtct      240
cccgccccaa gaccccccg ttgtctcctg ctcccctgc tcacgctcgg caccgcgctc        300
gcctccctcg gctcggccca aagcagcagc ttcagcccg aagcctggct acagcaatat      360
ggctacctgc ctcccgggga cctacgtacc cacacacagc gctcacccca gtcactctca      420
gcggccatcg ctgccatgca gaagttttac ggcttgcaag taacaggcaa agctgatgca      480
gacaccatga aggccatgag gcgccccga tgtggtgttc cagacaagtt tggggctgag       540
atcaaggcca atgttcgaag gaagcgctac gccatccagg gtctcaaatg caacataat      600 gaaatcactt tctgcatcca gaattacacc cccaaggtgg cgagtatgc cacatacgag       660 gccattcgca aggcgttccg cgtgtgggag agtgccacac cactgcgctt ccgcgaggtg      720
ccctatgcct acatccgtga gggccatgag aagcaggccg acatcatgat cttcttgcc       780 gagggcttcc atggcgacag cacgcccttc gatggtgagg gcggcttcct ggcccatgcc      840
tacttcccag gccccaacat tggaggagac acccactttg actctgccga gccttggact      900
gtcaggaatg aggatctgaa tggaaatgac atcttcctgg tggctgtgca cgagctgggc      960
catgccctgg ggctcgagca ttccagtgac ccctcggcca tcatggcacc cttttaccag     1020
tggatggaca cggagaattt tgtgctgccc gatgatgacc gccggggcat ccagcaactt     1080
tatgggggtg agtcagggtt ccccaccaag atgcccctc aacccaggac tacctccgg      1140 ccttctgttc ctgataaacc caaaaacccc acctatgggc caacatctg tgacgggaac      1200 tttgacaccg tggccatgct ccgagggag atgtttgtct tcaaggagcg ctggttctgg     1260
cgggtgagga ataaccaagt gatggatgga tacccaatgc ccattggcca gttctggcgg     1320
ggcctgcctg cgtccatcaa cactgcctac gagaggaagg atgcaaaatt cgtcttcttc     1380
aaaggagaca agcattgggt gtttgatgag gcgtccctgg aacctggcta ccccaagcac     1440
attaaggagc tgggccgagg gctgcctacc gacaagattg atgctgctct cttctggatg     1500
cccaatggaa agacctactt cttccgtgga aacaagtact accgtttcaa cgaagagctc     1560
agggcagtgg atagcgagta ccccaagaac atcaaagtct gggaagggat ccctgagtct     1620
cccagagggt cattcatggg cagcgatgaa gtcttcactt acttctacaa ggggaacaaa     1680
tactggaaat tcaacaacca gaagctgaag gtagaaccgg gctacccaa gtcagccctg      1740 agggactgga tgggctgccc atcgggaggc cggccggatg aggggactga ggaggagacg     1800
gaggtgatca tcattgaggt ggacgaggag ggcggcgggg cggtgagcgc ggctgccgtg     1860
gtgctgcccg tgctgctgct gctcctggtg ctggcggtgg gccttgcagt cttcttcttc     1920
agacgccatg ggaccccag gcgactgctc tactgccagc gttccctgct ggacaaggtc     1980
tgacgcccac cgccggcccg cccactccta ccacaaggac tttgcctctg aaggccagtg     2040
gcagcaggtg gtggtgggtg ggctgctccc atcgtcccga gcccctccc cgcagcctcc     2100 ttgcttctct ctgtccctg gctggcctcc ttcaccctga ccgcctccct ccctcctgcc     2160
ccggcattgc atcttccta gataggtccc ctgggggctc agtgggaggg cggcccttc      2220 cagcctctgc ccctcagggg aaccctgtag ctttgtgtct gtccagcccc atctgaatgt     2280
gttgggggct ctgcacttga aggcaggacc ctcagacctc gctggtaaag gtcaaatggg    2340
gtcatctgct ccttttccat cccctgacat accttaacct ctgaactctg acctcaggag    2400
```

```
gctctgggca ctccagccct gaaagcccca ggtgtaccca attggcagcc tctcactact    2460
ctttctggct aaaaggaatc taatcttgtt gagggtagag accctgagac agtgtgaggg    2520
ggtggggact gccaagccac cctaagacct tgggaggaaa actcagagag ggtcttcgtt    2580
gctcagtcag tcaagttcct cggagatctg cctctgcctc acctacccca gggaacttcc    2640
aaggaaggag cctgagccac tggggactaa gtgggcagaa gaaacccttg gcagccctgt    2700
gcctctcgaa tgttagcctt ggatggggct ttcacagtta gaagagctga aaccaggggt    2760
gcagctgtca ggtagggtgg ggccggtggg agaggcccgg gtcagagccc tgggggtgag    2820
cctgaaggcc acagagaaag aaccttgccc aaactcaggc agctggggct gaggcccaaa    2880
ggcagaacag ccagagggg caggagggga ccaaaaagga aaatgaggac gtgcagcagc     2940
attggaaggc tggggccggg caggccaggc caagccaagc aggggccac agggtgggct     3000 gtggagctct caggaagggc cctgaggaag gcacacttgc tcctgttggt ccctgtcctt    3060
gctgcccagg cagcgtggag gggaagggta gggcagccag agaaaggagc agagaaggca    3120
cacaaacgag gaatgagggg cttcacgaga ggccacaggg cctggctggc cacgctgtcc    3180
cggcctgctc accatctcag tgaggggcag gagctggggc tcgcttaggc tgggtccacg    3240
cttccctggt gccagcaccc ctcaagcctg tctcaccagt ggcctgccct ctcgctcccc    3300
cacccagccc acccattgaa gtctccttgg gccaccaaag gtggtggcca tggtaccggg    3360
gacttgggag agtgagaccc agtggaggga gcaagaggag agggatgtcg ggggggtggg    3420
gcacggggta ggggaaatgg ggtgaacggt gctggcagtt cggctagatt tctgtcttgt    3480 ttgtttttt gttttgttta atgtatattt ttattataat tattatatat gaattccaaa     3540
aaaaaaaaaa aaaaaaa                                                    3558

<210> SEQ ID NO 38
<211> LENGTH: 8
<212> TYPE: PRT
<213> ORGANISM: Homo sapiens

<400> SEQUENCE: 38

Ser Arg Pro Gln Gly Pro Glu Leu
1               5
```

COMPOSITIONS AND METHODS FOR INHIBITING MATRIX METALLOPROTEINASE (MMP)-MEDIATED CELL MIGRATION

This application claims priority to co-pending U.S. provisional Application Ser. No. 61/325,962, filed Apr. 20, 2010, which is herein incorporated by reference in its entirety for all purposes.

STATEMENT OF GOVERNMENT SUPPORT

This invention was made with government support under grant number CA113553 awarded by the National Institutes of Health (NIH). The government has certain rights in the invention.

FIELD OF INVENTION

The invention provides peptides, portions and derivatives thereof, that are useful for reducing cell migration, and for reducing symptoms of pathological diseases that are associated with undesirable cell migration, and in particular cell migration induced by one or more matrix metalloproteinase (MMP). This invention also provides peptides that are useful for detecting (e.g., imaging) cancers and for delivering toxins to cancer cells.

BACKGROUND

Several diseases involve undesired cell migration, including cancer, systemic lupus erythematosus (SLE), Sjogren's syndrome (SS), systemic sclerosis (SS), polymyositis, rheumatoid arthritis (RA), multiple sclerosis (MS), atherosclerosis, cerebral ischemia, abdominal aortic aneurysm (AAA), myocardial infarction (MI), cerebral amyloid angiopathy (CAA), angiogenesis, inflammation, and eczema. These diseases are the cause of loss of life and/or loss of the quality of life. While some therapeutic approaches have been successful, these diseases have not been completely eradicated. For example, cancer metastasis is responsible for 90% of treatment failure among cancer patients. Thus, there remains a need for development of novel treatment strategies to reduce diseases involving undesired cell migration, to improve the quality of life, and to prolong the survival, of patients suffering from these diseases.

SUMMARY OF THE INVENTION

The invention provides in one embodiment a composition comprising a purified polypeptide that contains an amino acid sequence selected from the group of a) GYPMP (SEQ ID NO:04), b) VMDGYPMP (SEQ ID NO:01), and c) GYPKSALR (SEQ ID NO:03), wherein the polypeptide a) does not comprise a PEX domain of an MMP, and b) reduces at least one of homodimerization and heterodimerization of an MMP that contains the amino acid sequence. While not intending to limit the invention to a particular mechanism, in one embodiment, the polypeptide reduces migration of a cell expressing a MMP. In a further embodiment, the polypeptide that contains GYPMP (SEQ ID NO:04), comprises VMDGYPMP (SEQ ID NO:01).

The invention also provides in one embodiment a method for reducing one or more symptoms of a disease (e.g., Table 3) associated with cell expression of a matrix metalloproteinase (MMP), comprising a) providing i) a mammalian subject in need of reducing one or more symptoms of the disease, and ii) any one or more of the compositions disclosed herein, and b) administering to the subject a therapeutic amount of the composition to produce a treated subject, wherein the administering is under conditions for reducing one or more symptoms of the disease. In one embodiment, the method further comprises c) detecting a reduction in one or more symptoms of the disease in the treated subject. In an alternative embodiment, one or more symptoms of the disease comprises increased cell migration in the presence of an MMP compared to in the absence of an MMP. In one embodiment, the therapeutic amount of the composition specifically reduces cell migration that is mediated by MT1-MMP. In another embodiment, the therapeutic amount of the composition does not reduce cell migration that is mediated by one or more of MMPs, e.g. MMP-9, MT3-MMP, and MT6-MMP. In yet a further embodiment, the composition comprises an amount of the polypeptide that reduces homodimerization of MT1-MMP. In an alternative embodiment, the composition comprises an amount of the polypeptide that reduces heterodimerization of MT1-MMP and CD44. In a preferred embodiment, the disease comprises cancer metastasis, including but not limited to metastases to the lung. In another embodiment, the polypeptide that is comprised in the composition is covalently linked to a cytotoxic agent or to a prodrug of a cytotoxic agent.

The invention additionally provides in one embodiment a method for reducing cell migration, comprising a) providing i) a cell expressing a matrix metalloproteinase (MMP), and ii) any one or more of the compositions disclosed herein, and b) administering the composition to the cell under conditions for reducing migration of the cell. In one embodiment, the method further comprises c) detecting reduced migration of the cell.

The invention also provides in one embodiment a composition comprising a purified polypeptide that contains an amino acid sequence selected from the group of a) a matrix metalloproteinase (MMP) sequence corresponding to the GYPMP (SEQ ID NO:04) of the hemopexin (PEX) domain of a membrane type 1 matrix metalloproteinase (MT1-MMP), and b) a MMP sequence corresponding to the VMDGYPMP (SEQ ID NO:01) of the PEX domain of the MT1-MMP, and c) a MMP sequence corresponding to the GYPKSALR (SEQ ID NO:03) of the PEX domain of the MT1-MMP, wherein the polypeptide a) does not comprise a PEX domain of a MMP, and b) reduces at least one of homodimerization and heterodimerization of an MMP that contains the amino acid sequence. In one embodiment, the polypeptide that contains the MMP sequence corresponding to the GYPMP (SEQ ID NO:04) of the PEX domain of the MT1-MMP comprises an amino acid sequence selected from the group of SEQ ID NO:05-18 (Table 1). In another embodiment, the polypeptide that contains the MMP sequence corresponding to the VMDGYPMP (SEQ ID NO:01) of the PEX domain of the MT1-MMP comprises an amino acid sequence selected from the group of SEQ ID NO:05-18 (Table 1). In a further embodiment, the polypeptide that contains the MMP sequence corresponding to the GYPKSALR (SEQ ID NO:03) of the PEX domain of the MT1-MMP comprises an amino acid sequence selected from the group of SEQ ID NO:20-33 (Table 2).

Also provided herein, in one embodiment, is a method for detecting a disease associated with cell expression of a matrix metalloproteinase (MMP) in a subject comprising a) providing i) any one or more of the compositions disclosed herein, and ii) a sample from the subject, b) contacting the composition with the sample, and c) detecting binding of the polypeptide that is comprised in the composition to the sample, thereby detecting the disease in the subject.

BRIEF DESCRIPTION OF THE DRAWINGS

FIG. 12: Biological function of MMPs.

FIG. 29: Shedding of cell surface E-cadherin by cells expressing MT1-GFP chimera.

FIG. 30: MT1-MMP enhances LNCaP cell migration.

FIG. 31: Digestion of fluorescein isothiocyanate (FITC)-labeled Matrigel by MT1-MMP expressing LNCaP cells.

FIG. 32: MT1-MMP-mediated cell migration is dependent on the PEX Domain of MT1-MMP, but not enzymatic activity.

FIG. 33: The cytoplasmic domain of MT1-MMP is not required for MT1-MMP-induced cell migration and scattering

FIG. 35: Expression of MT1-MMP in MCF-7 cells decreases the localization of vinculin in focal adhesion.

FIG. 36: Exploration of the signaling pathways in MT1-MMP mediated prostate cell migration.

FIG. 37: MT1-MMP induced LNCaP cell phenotypic change in type I collagen.

FIG. 38: MT-1-MMP promotes LNCaP and MCF-7 cell scattering and proliferation in a 3D culture model.

FIG. 39: MT1-MMP promotes tumorigenicity of breast carcinoma MCF7 cells.

FIG. 40: MT1-MMP enhanced prostate cancer invasion and metastasis.

FIG. 42: Strand four of blades I and IV are required for MT1-MMP-mediated proMMP-2 activation and cell migration, but not substrate degradation.

FIG. 43: Similarity of the PEX domain structures of MMP-1 and MT1-MMP.

FIG. 44: Summary of substituted mutations of the PEX domain of MT1-MMP and MMP-1.

FIG. 45: Purification of recombinant soluble MT1-MMP.

FIG. 47: *Homo sapiens* MT1-MMP, matrix metallopeptidase 14 (membrane-inserted) (MMP14), (NCBI Reference Sequence: NM_004995.2) amino acid sequence and nucleotide sequence (SEQ ID NOS: 36, and 37)

DEFINITIONS

Figure 1:
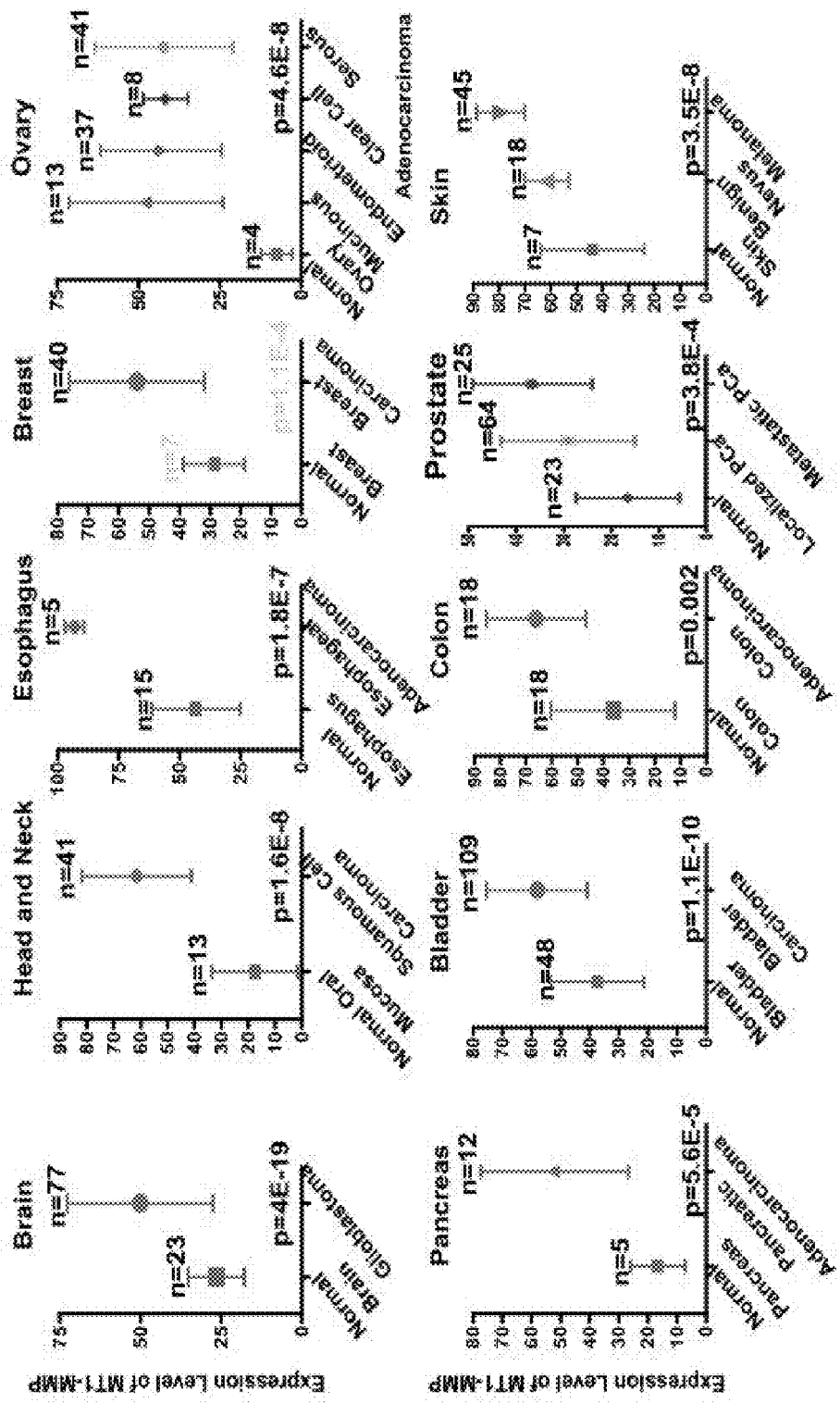
FIG. 1: Data mining of MT1-MMP expression in human cancers and normal tissues.

To facilitate understanding of the invention, a number of terms are defined below.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed using a recombinant DNA molecule.

The terms "endogenous" and "wild type" when in reference to a sequence refer to a sequence that is naturally found in the cell or virus into which it is introduced so long as it does not contain some modification relative to the naturally occurring sequence. The term "heterologous" refers to a sequence that is not endogenous to the cell or virus into which it is introduced.

The terms "mutation" and "modification" refer to a deletion, insertion, or substitution.

A "deletion" is defined as a change in a nucleic acid sequence or amino acid sequence in which one or more nucleotides or amino acids, respectively, is absent.

An "insertion" or "addition" is that change in a nucleic acid sequence or amino acid sequence that has resulted in the addition of one or more nucleotides or amino acids, respectively.

A "substitution" in a nucleic acid sequence or an amino acid sequence results from the replacement of one or more nucleotides or amino acids, respectively, by a molecule that is a different molecule from the replaced one or more nucleotides or amino acids. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol. Substitution of an amino acid may be conservative or non-conservative. "Conservative substitution" of an amino acid refers to the replacement of that amino acid with another amino acid which has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains that may be conservatively substituted one for the other include phenylalanine, tyrosine, and tryptophan. Cysteine and methionine are sulphur-containing amino acids which may be conservatively substituted one for the other. Also, asparagine may be conservatively substituted for glutamine, and vice versa, since both amino acids are amides of dicarboxylic amino acids. In addition, aspartic acid (aspartate) may be conservatively substituted for glutamic acid (glutamate) as both are acidic, charged (hydrophilic) amino acids. Also, lysine, arginine, and histidine may be conservatively substituted one for the other since each is a basic, charged (hydrophilic) amino acid. "Non-conservative substitution" is a substitution other than a conservative substitution. Guidance in determining which and how many amino acid residues may be substituted, inserted or deleted without abolishing biological and/or immunological activity may be found using computer programs well known in the art, for example, DNAStar™ software.

A "variant" or "homolog" of an amino acid sequence of interest refers to an amino acid sequence that differs by insertion, deletion, and/or conservative substitution of one or more amino acids from the amino acid sequence of interest. In one embodiment, the variant sequence has at least 95% identity, including at least 90% identity, at least 85% identity, at least 80% identity, at least 75% identity, at least 70% identity, and/or at least 65% identity with the amino acid sequence of interest. Guidance in determining which and how many amino acid residues may be substituted, inserted or deleted without abolishing biological and/or immunological activity may be found using computer programs well known in the art, for example, DNAStar™ software.

The term "corresponding" when in reference to a first amino acid sequence in a first polypeptide sequence in relation to a second amino acid sequence in a second polypeptide sequence means that the positions of the first and second amino acid sequences are aligned when the first and second polypeptide sequences are aligned.

"Alignment" of 2 or more sequences (e.g., DNA, RNA, and/or protein sequences) refers to arranging the 2 or more sequences to identify the highest number and/or proportion of matching amino acids in the sequences, thereby identifying regions of similarity between the sequences. Polypeptide sequences may be aligned using software available in the art.

The term "homodimerization" refers to the oligomerization between two polypeptides having the same amino acid sequence. On the other hand, the terms "heterodimerization" refers to the oligomerization between two polypeptides having different amino acid sequences. An amino acid sequence is different from another amino acid sequence if it contains one or more amino acids that are not the same as the amino acids in the other amino acid sequence.

The term "specific oligomerization," "specific binding," "specific pairing," "binding specificity," and "pairing specificity," when made in reference to two protein sequences is herein used to refer to the preferential oligomerization between two protein sequences as compared to the oligomerization between either of these two protein sequences to a third protein sequence. Specific oligomerization may be heterospecific or homospecific. The terms "homospecific oligomerization" and "homospecificity" as used herein refer to the specific oligomerization between two or more polypeptides having the same amino acid sequence. On the other hand, the terms "heterospecific oligomerization" and "heterospecificity" refer to the specific oligomerization between two or more polypeptides having different amino acid sequences.

A "variant" or "homolog" of a nucleotide sequence of interest refers to a nucleotide sequence that differs by insertion, deletion, and/or substitution of one or more nucleotides from the nucleotide sequence of interest. In one embodiment, the variant sequence has at least 95% identity, including at least 90% identity, at least 85% identity, at least 80% identity, at least 75% identity, at least 70% identity, and/or at least 65% identity with the nucleotide sequence of interest.

The term "expression vector" as used herein refers to a recombinant DNA molecule containing a desired coding sequence and appropriate nucleic acid sequences necessary for the expression (i.e., transcription and/or translation) of the operably linked coding sequence in a particular host organism. Expression vectors are exemplified by, but not limited to, plasmid, phagemid, shuttle vector, cosmid, virus, chromosome, mitochondrial DNA, plastid DNA, and nucleic acid fragment. Nucleic acid sequences used for expression in prokaryotes include a promoter, optionally an operator sequence, a ribosome binding site and possibly other sequences. Eukaryotic cells are known to utilize promoters, enhancers, and termination and polyadenylation signals.

The terms "purified," "isolated," and grammatical equivalents thereof as used herein, refer to the reduction in the amount of at least one undesirable component (such as cell type, protein, and/or nucleic acid sequence) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in an "enrichment," i.e., an increase in the amount of a desirable cell type, protein and/or nucleic acid sequence in the sample.

The terms "operable combination" and "operably linked" when in reference to the relationship between nucleic acid sequences and/or amino acid sequences refers to linking the sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest resulting in an mRNA that directs the synthesis of a polypeptide encoded by the nucleotide sequence of interest.

As used herein, the terms "treat", "treating", "treatment" and grammatical equivalents refers to combating a disease or disorder, as for example in the management and care of a patient. In one embodiment, treating a disease (e.g., cancer, metastasis, etc.) includes reducing one or more symptoms of the disease.

As used herein, the terms "diagnose", "diagnosis" or "diagnosing" refers to the recognition of a disease by its signs and symptoms (e.g., resistance to conventional therapies), or genetic analysis, pathological analysis, histological analysis, and the like.

As used herein, the term "diagnostic" refers to a compound that assists in the identification and characterization of a health or disease state. The diagnostic can be used in standard assays as is known in the art.

As used herein, the terms "cancer cell" and "tumor cell" refer to a cell undergoing early, intermediate or advanced stages of multi-step neoplastic progression as previously described (Pitot et al., Fundamentals of Oncology, 15-28 (1978)), herein incorporated by reference. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. A cell in the early stages of malignant progression is referred to as a "hyperplastic cell" and is characterized by dividing without control and/or at a greater rate than a normal cell of the same cell type in the same tissue. Proliferation may be slow or rapid but continues unabated. A cell in the intermediate stages of neoplastic progression is referred to as a "dysplastic cell". A dysplastic cell resembles an immature epithelial cell, is generally spatially disorganized within the tissue and loses its specialized structures and functions. During the intermediate stages of neoplastic progressions an increasing percentage of the epithelium becomes composed of dysplastic cells. "Hyperplastic" and "dysplastic" cells are referred to as "pre-neoplastic" cells. In the advanced stages of neoplastic progression a dysplastic cell become a "neoplastic" cell. Neoplastic cells are typically invasive i.e., they either invade adjacent tissues, or are shed from the primary site and circulate through the blood and lymph to other locations in the body where they initiate secondary cancers. Cancer cell includes a metastatic cancer cell and non-metastatic cancer cell.

"Metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates.

A "cancer at risk for metastases" refers to a cancer that may differentiate into a metastatic cancer. Such risk may be based on family history, genetic factors, type of cancer, environmental factors, etc.

The term "cancer" or "neoplasia" refers to a plurality of cancer cells.

"Carcinoma" refers to a malignant new growth made up of epithelial cells tending to infiltrate the surrounding tissues and give rise to metastases.

The terms "therapeutic amount," "pharmaceutically effective amount," "therapeutically effective amount," and "biologically effective amount," are used interchangeably herein to refer to an amount that is sufficient to achieve a desired result, whether quantitative or qualitative. In particular, a pharmaceutically effective amount is that amount that results in the reduction, delay, and/or elimination of undesirable effects (such as pathological, clinical, biochemical and the like) in the subject that are associated with disease. For example, a "therapeutic amount that reduces cancer metastasis" is an amount that that reduces, delays, and/or eliminates one or more symptoms of cancer metastasis. Also, a "therapeutic amount that reduces one or more symptoms of cancer" is an amount that reduces, delays, and/or eliminates one or more symptoms of cancer. The actual amount encompassed by the term "therapeutic amount" will depend on the route of administration, the type of subject being treated, and the physical characteristics of the specific subject under consideration. These factors and their relationship to determining this amount are well known to skilled practitioners in the medical, veterinary, and other related arts and are further discussed herein.

The terms "reduce," "inhibit," "diminish," "suppress," "decrease," and grammatical equivalents (including "lower," "smaller," etc.) when in reference to the level of any molecule (e.g., amino acid sequence, and nucleic acid sequence such as those encoding any of the polypeptides described herein), cell, and/or phenomenon (e.g., cell migration, disease symptom, heterodimerization, homodimerization, binding to a molecule, affinity of binding, expression of a nucleic acid sequence, transcription of a nucleic acid sequence, enzyme activity, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first subject is exemplified by, but not limited to, a subject to whom the invention's compositions have been administered. In a further embodiment, the second subject is exemplified by, but not limited to, a subject to whom the invention's compositions have not been administered. In an alternative embodiment, the second subject is exemplified by, but not limited to, a subject to whom the invention's compositions have been administered at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions is sought to be determined in one individual. In another embodiment, the first and second subjects may be different individuals, such as when comparing the effect of the invention's compositions on one individual participating in a clinical trial and another individual in a hospital.

The terms "increase," "elevate," "raise," and grammatical equivalents (including "higher," "greater," etc.) when in reference to the level of any molecule (e.g., amino acid sequence, and nucleic acid sequence such as those encoding any of the polypeptides described herein), cell, and/or phenomenon (e.g., cell migration, disease symptom, heterodimerization, homodimerization, binding to a molecule, affinity of binding, expression of a nucleic acid sequence, transcription of a nucleic acid sequence, enzyme activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first subject is exemplified by, but not limited to, a subject to whom the invention's compositions have been administered. In a further embodiment, the second subject is exemplified by, but not limited to, a subject to whom the invention's compositions have not been administered. In an alternative embodiment, the second subject is exemplified by, but not limited to, a subject to whom the invention's compositions have been administered at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions is sought to be determined in one individual. In another embodiment, the first and second subjects may be different individuals, such as when comparing the effect of the invention's compositions on one individual participating in a clinical trial and another individual in a hospital.

Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc.

BRIEF DESCRIPTION OF THE INVENTION

The invention provides peptides, portions and derivatives thereof, that are useful for reducing cell migration, and for reducing symptoms of pathological diseases that are associated with undesirable cell migration, and in particular cell migration induced by one or more matrix metalloproteinase (MMP). This invention also provides peptides that are useful for detecting (e.g., imaging) cancers.

To develop effective drugs and methods to treat patients with diseases that involve aberrant cell migration (e.g., cancer (including metastatic cancer), systemic lupus erythematosus (SLE), Sjogren's syndrome (SS), systemic sclerosis (SS), polymyositis, rheumatoid arthritis (RA), multiple sclerosis (MS), atherosclerosis, cerebral ischemia, abdominal aortic aneurysm (AAA), myocardial infarction (MI), cerebral amyloid angiopathy (CAA), angiogenesis, inflammation, and eczema), an initial requirement is to identify the weak link in the migrating cell that can be attacked with a specific drug.

Early diagnosis and prevention of metastasis are major stumbling blocks in the "war against cancer". Although important advances have been made in the management of solid tumors, the complexity of cancer biology continues to defy technologic advances. In diagnosing and monitoring malignant tumors, physicians classically rely on X-rays to image a space-occupying lesion. However, these images are often late indicators of tumors. Therefore, there is a pressing need for an effective tool for early diagnosis and treatment of cancer.

Noninvasive molecular imaging of a cancer will increase our understanding of cancer biology, enhance early detection of malignancies, locate metastatic disease, stage tumors, evaluate the availability of therapeutic targets, and monitor the efficacy of treatment. Due to the success of target-based therapies against kinases, cellular receptors, and signaling molecules, molecular probes to image these targets have been developed. Although these molecular probes show promise as methods to aid in the early detection of tumors, imaging probes for these targets have faced several hurdles. One of the difficulties is that frequent mutations of the target genes lead to potential false negative outcomes. Novel tools are needed to increase the reliability, efficiency, and cost-effectiveness of early cancer diagnosis.

Ideally, the target of a molecular imaging probe and/or invasion-inhibitory compound should be stable and ubiquitously expressed in most types of tumors at an early stage, in order that it can be used for primary screening and treatment. Membrane type 1-matrix metalloproteinase (MT1-MMP) meets these criteria since it is upregulated in most types of early human cancers and correlated with advanced clinical stage and poor prognosis. MT1-MMP has been demonstrated to play important roles in tumor growth, angiogenesis, invasion and metastasis by digesting extracellular matrix, activating proMMP-2, and -13, and inducing epithelial to mesenchymal transition. In migrating cancer cells, MT1-MMP localizes to invadopodia at the leading edge in invasive cells, placing it in an ideal position to be detected and targeted.

This invention describes a development of bi-functional peptide for early/aggressive cancer diagnosis and for prevention of cancer migration/invasion. This invention permits us to be able to detect early invasive cancer cells and inhibit cancer cell invasion in a live subject. This invention also facilitates to specifically deliver toxin to cancer cells expressing MT1-MMP. The invention has significant future implications because development of imaging tools for diagnosis of early/aggressive cancers will significantly improve the outcome of patients with cancer and facilitate translation from bench to bedside. In addition, the developed tools can be also used as "biological missile" specifically targeting cancer cells, hence, it prevents cancer spreading, which accounts for 90% treatment failure of all cancer patients.

Based on our studies of the structure-function relationship of the MT1-MMP hemopexin (PEX)-like domain, we designed and synthesized peptides mimicking 8 amino acids of the outermost β strand of blades I, II, III and IV from the PEX domain, named IS4-8 (VMDGYPMP) (SEQ ID NO:01), IIS4-8 (FDEASLEP) (SEQ ID NO:02), and IVS4-8 (GYPKSALR) (SEQ ID NO:03), respectively. Corresponding scrambled peptides were synthesized as controls. The IS4-8 and IVS4-8 peptides reduce cell migration in COS-1 cells transfected with MT1-MMP cDNA, or human MDA-MB-231, and -435 breast cancer cells, and human HT1080 fibrosarcoma cells expressing endogenous MT1-MMP.

These inhibitory peptides do not affect cell migration induced by MMP-9 or MT6-MMP. We further designed truncated forms of IS4-8 and IVS-8 peptides from the N- and C-terminus of the peptides. The C-terminal 5 amino acids of the IS4-8, named IS4-5 (GYPMP) (SEQ ID NO:04) is essential for inhibition of functional MT1-MMP. Using the 3D invasion assay, we demonstrated that IS4-8, IVS4-8, and IS4-5 peptides ($IC_{50}$=1.5, 10, and 1.5 µM, respectively) efficiently prevent human MDA-MB-231 breast cancer cell invasion. By flow cytometry analysis, biotinylated IS4-5 peptides specifically binds to cells expressing MT1-MMP. Thus, the PEX domain of MT1-MMP is a high-specificity target for interference with MT1-MMP-induced cancer cell invasion and for identification of cancer cells expressing MT1-MMP. These novel bi-functional inhibitory peptides will provide specificity with limited systemic toxicity.

Mounting evidence has demonstrated that both proteolytic and non-proteolytic activities of MT1-MMP are required for MT1-MMP-enhanced cancer cell invasion. The conditioned medium from human breast cancer MCF-7 cells ectopically expressing MT1-MMP in the presence of scrambled peptides or specific peptides was examined by gelatin zymography to determine whether interference with the PEX domain of MT1-MMP by the peptides also affects the proteolytic activity of MT1-MMP. We demonstrated that IS4-8 and -5 peptides specifically inhibited MT1-MMP-induced proMMP-2 activation, suggesting these peptides inhibits both cell migration and proteolytic activity.

We tested the stability of the synthetic peptides by incubating the peptides with serum prepared from mouse blood at 37° C. for 6, 24, and 48 hours. We did not observe significant reduction of inhibitory activity of the peptide on cell migration, suggesting that the peptides are not highly sensitive to serum peptidases or other proteases.

A chorioallantoic membrane (CAM) assay and xerographic tumor mice model may also be used to evaluate inhibition of MT1-MMP-mediated angiogenesis and metastasis by the invention's peptides.

Several studies attempted to develop molecular imaging probes for detection of MT1-MMP-expressing cancer cells. These probes include MT1-MMP cleavable peptides isolated from phage display peptide library and MT1-MMP monoclonal antibody (Watkins et al. (2009) *Bioorg Med Chem* 17, 653-659; Temma et al. (2009) *Biol Pharm Bull* 32, 1272-1277). However, potential problems of host immune response using MT1-MMP antibodies and lack of tumor homing feature of MT1-MMP-cleavable peptide hinder the process from the bench-to-bedside.

The invention's polypeptides solve these problems and are useful in a number of applications. For example, the invention's bi-functional peptides specifically bind to MT1-MMP at cancer cell surface, and therefore, the peptides facilitate homing to cancer cells. By covalently binding with fluorophore or radioisotope, the polypeptides can be used for cancer diagnosis and detection. In addition, the peptides can direct cytotoxic agents specifically to cancer cells for inducing cancer cell death and for preventing cancer cell migration and invasion.

This invention has significant useful applications because development of imaging tools for diagnosis of cancers will significantly improve the outcome of patients with cancer and facilitate translation from bench to bedside. In addition, the developed tools can be also used as "biological missile" specifically targeting cancer cells, hence, it prevents cancer spreading, which accounts for 90% treatment failure of all cancer patients.

To develop an effective drug to detect cancers at early stage and to prevent further dissemination of aggressive cancers, an initial requirement is to identify the weak link in the cancer cell that can be attacked with a specific drug. We and others have demonstrated that a membrane anchored tissue degrading enzyme, called MT1-MMP is highly expressed in human cancer tissues as compared to normal adjacent tissue. Expression of MT1-MMP is correlated with cancer stage and recurrence. MT1-MMP also can enhance cancer cell migration and invasion, hence MT1-MMP enhances cancer metastasis. Therefore, inhibition of functional MT1-MMP represents a viable approach to intervene in cancer metastasis (Itoh et al. (2001) EMBO Journal 20(17):4782-4793; Seiki et al., U.S. Patent Application No. US 2004/0120954). In addition, the invention's polypeptides, including portions of MT1-MMP, can be used as a biomarker for detection of cancer with aggressive properties.

By employing a biochemical approach, we identified a region that is required for MT1-MMP enhanced cell migration. Given the fact that cell migration is a critical determinant of cancer invasiveness and metastasis, targeting MMP-enhanced cell migration represents one viable approach to prevent cancer dissemination. In order to target MT1-MMP-enhanced cell migration, we have employed molecular techniques to identify a minimal motif within MT1-MMP molecule required for cell migration. Based on the identified sequence, we designed and synthesized inhibitory peptides. Using a cell testing assay to evaluate cell migratory ability, we found the inhibitory peptides efficiently blocked MT1-MMP-induced cell migration, but not reagents from the scrambled control peptide. We further demonstrated that the inhibitory peptides are specific for MT1-MMP-induced cell migration, but not for other MMP-induced cell migration. Therefore, the inhibitory peptide developed by the inventors can be used to therapeutically intervene in cancer metastasis. Furthermore, the developed peptides were found to interact with cancer cells expressing MT1-MMP, hence, these peptides can also be used as an imaging tool for early and aggressive cancer diagnosis. Therefore, the peptides of the invention can be used to diagnose and also to therapeutically intervene in diseases involving undesired cell migration (e.g., cancer metastasis).

DETAILED DESCRIPTION OF THE INVENTION

The invention provides peptides, portions and derivatives thereof, that are useful for reducing cell migration, and for reducing symptoms of pathological diseases that are associated with undesirable cell migration, and in particular cell migration induced by one or more matrix metalloproteinase (MMP). This invention also provides peptides that are useful for detecting (e.g., imaging) cancers.

The invention is further described under A. Matrix metalloproteinases, B. Exemplary Compositions Of The Invention, C. Conjugates Of The Invention's Peptide sequences Linked To Cytotoxic Agents And/Or To Prodrugs, D. Exemplary Uses Of The Invention's Compositions, Including Therapeutic Applications, and E. Exemplary Uses Of The Invention's Compositions in Detecting MMPs And Diagnostic Applications.

A. Matrix Metalloproteinases

Figure 11:
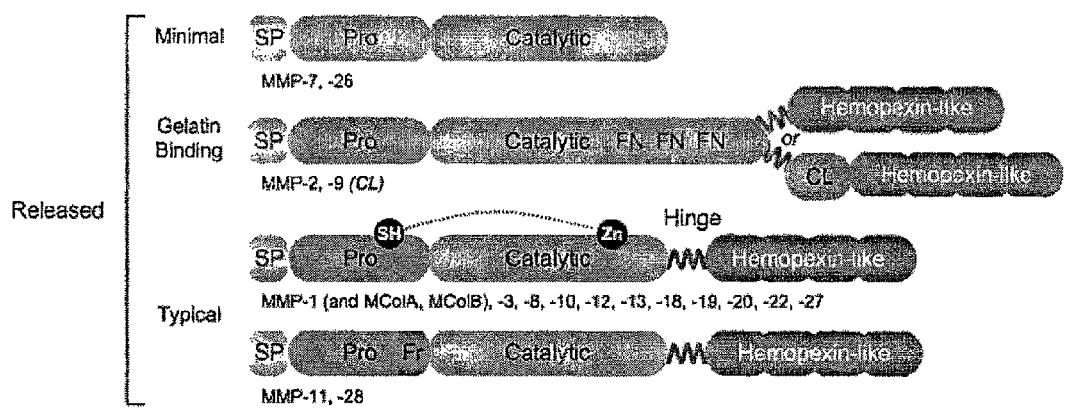
FIG. 11: Matrix metalloproteinase (MMP) family members
Figure 13:
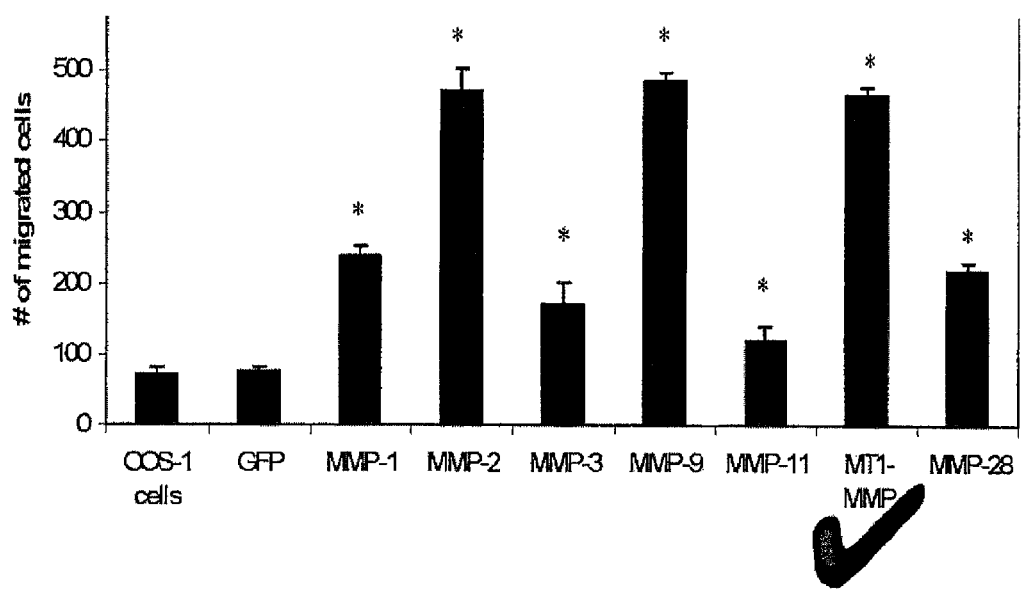
FIG. 13: Enhanced cell migration by over-expression of ProMMPs.
Figure 14:
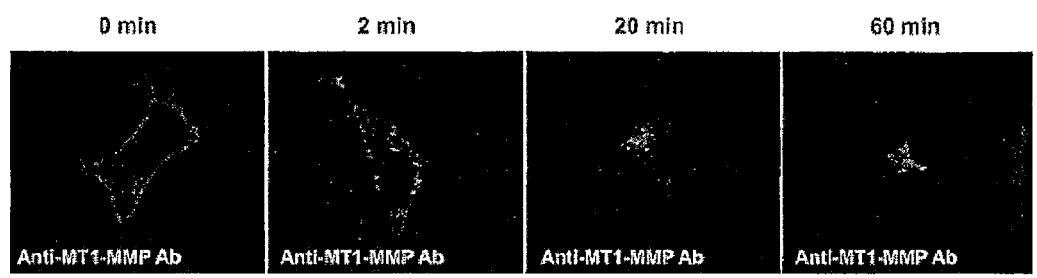
FIG. 14: Endocytosis of cell surface MT1-MMP.
Figure 15:
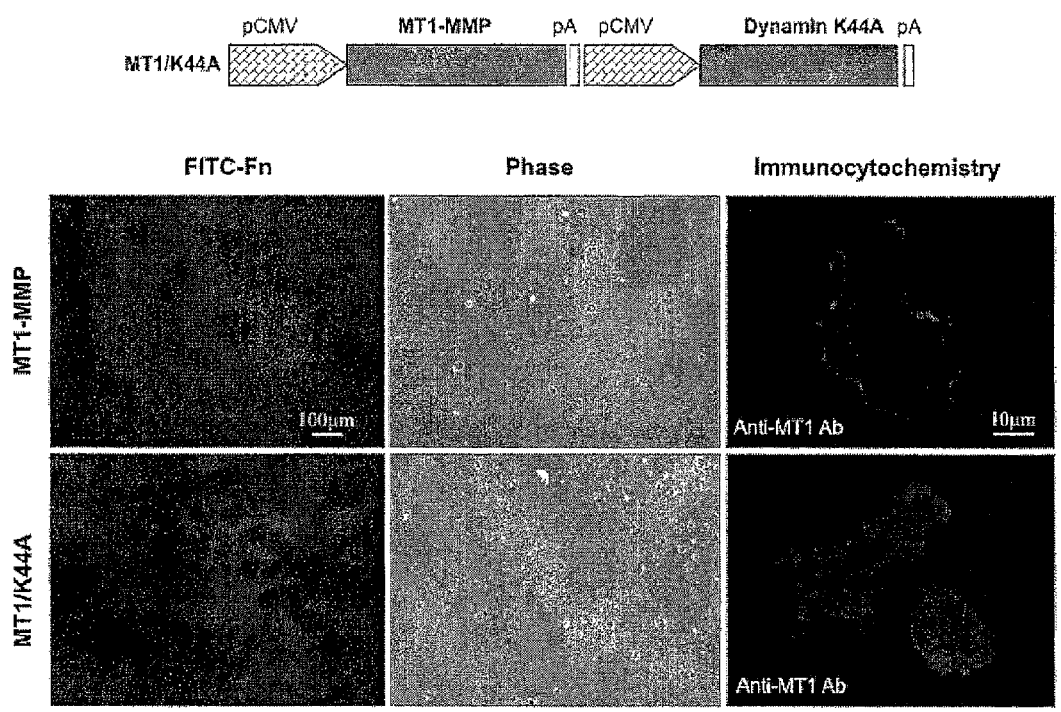
FIG. 15: Enhanced cell migration in transfected cells by blocking MT1-MMP endocytosis.
Figure 16:
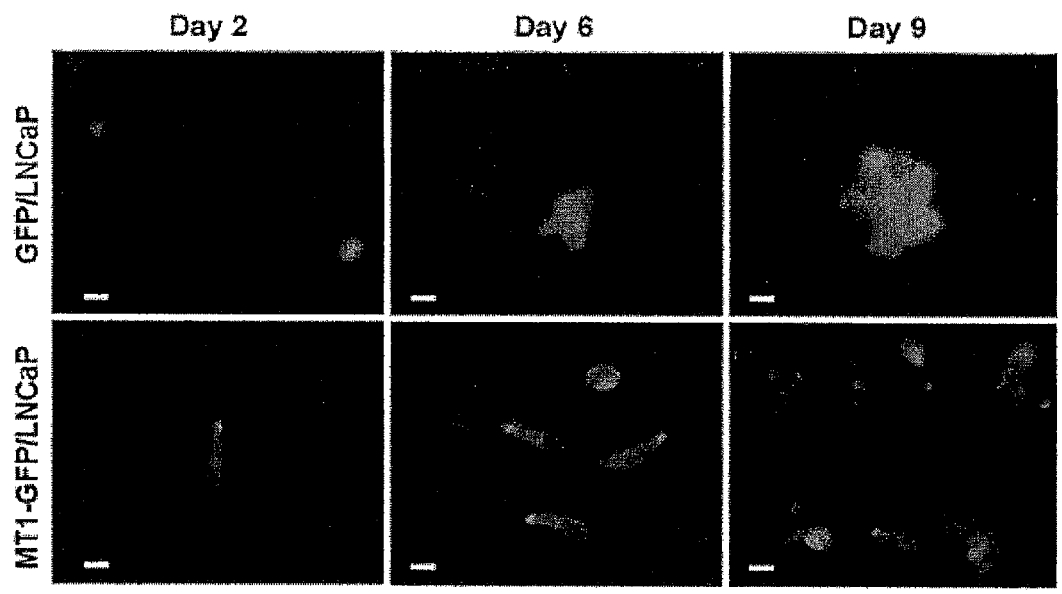
FIG. 16: MT1-MMP induces LNCaP Cell Scattering In 3-dimensional Type 1 Collagen Gels.
Figure 17:
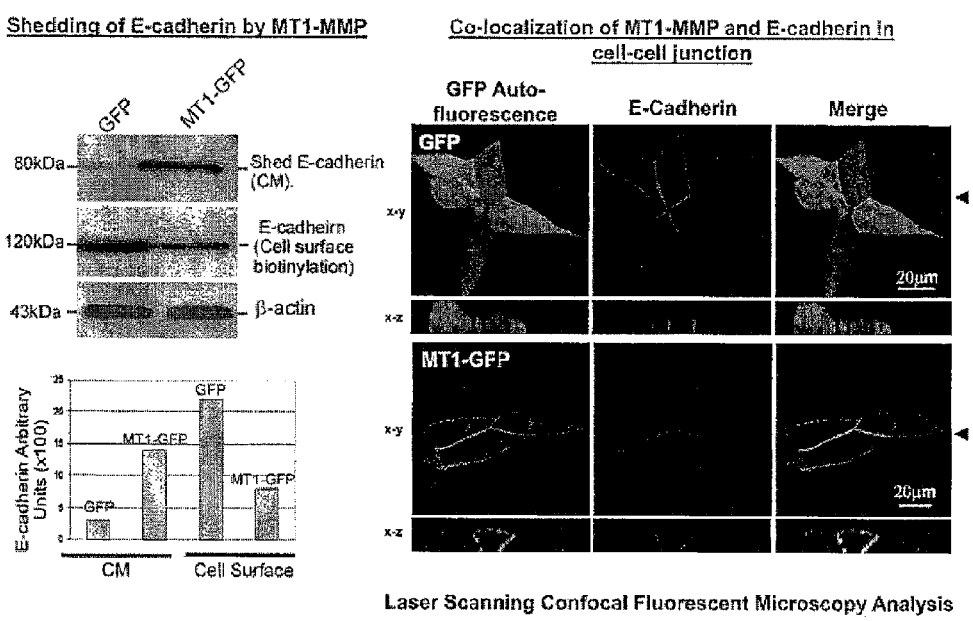
FIG. 17: Enhanced shedding of cell-cell adhering molecular E-cadherin by MT1-MMP in LNCaP cells.
Figure 18:
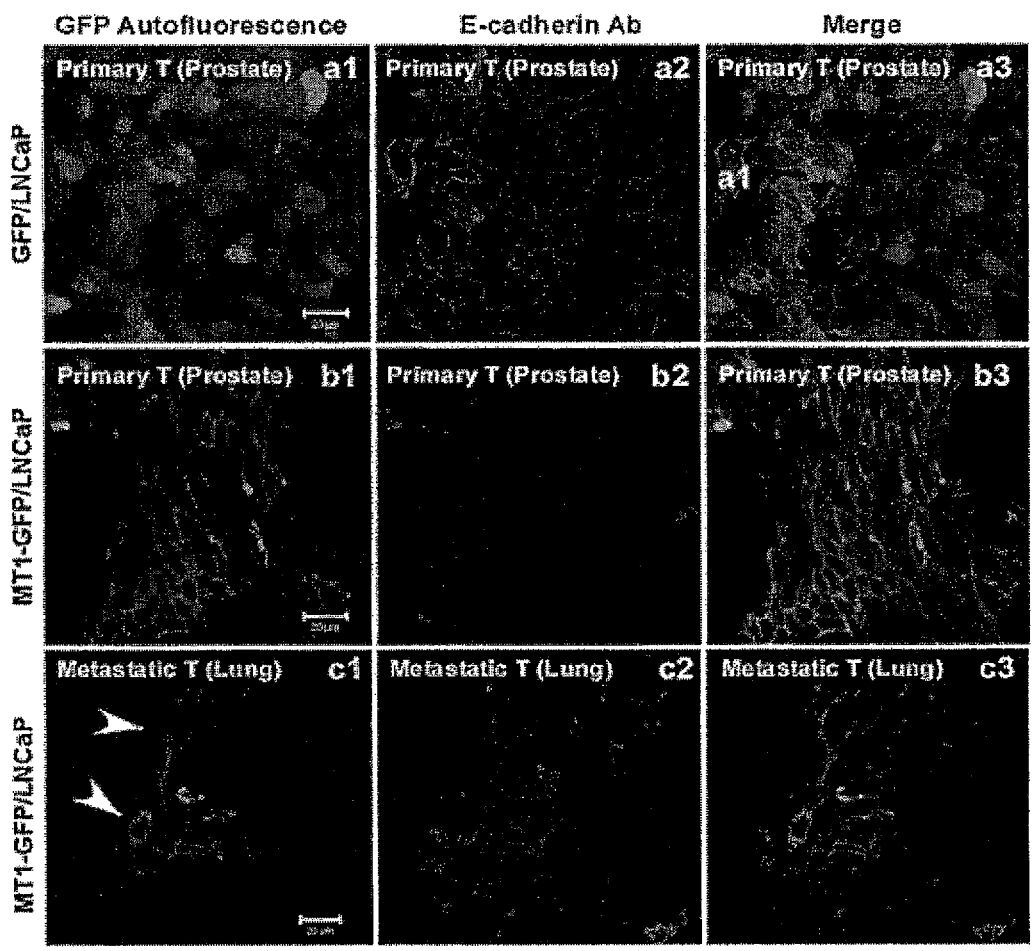
FIG. 18: Loss of E-cadherin expression in MT1-GFP prostate tumors.
Figure 19:
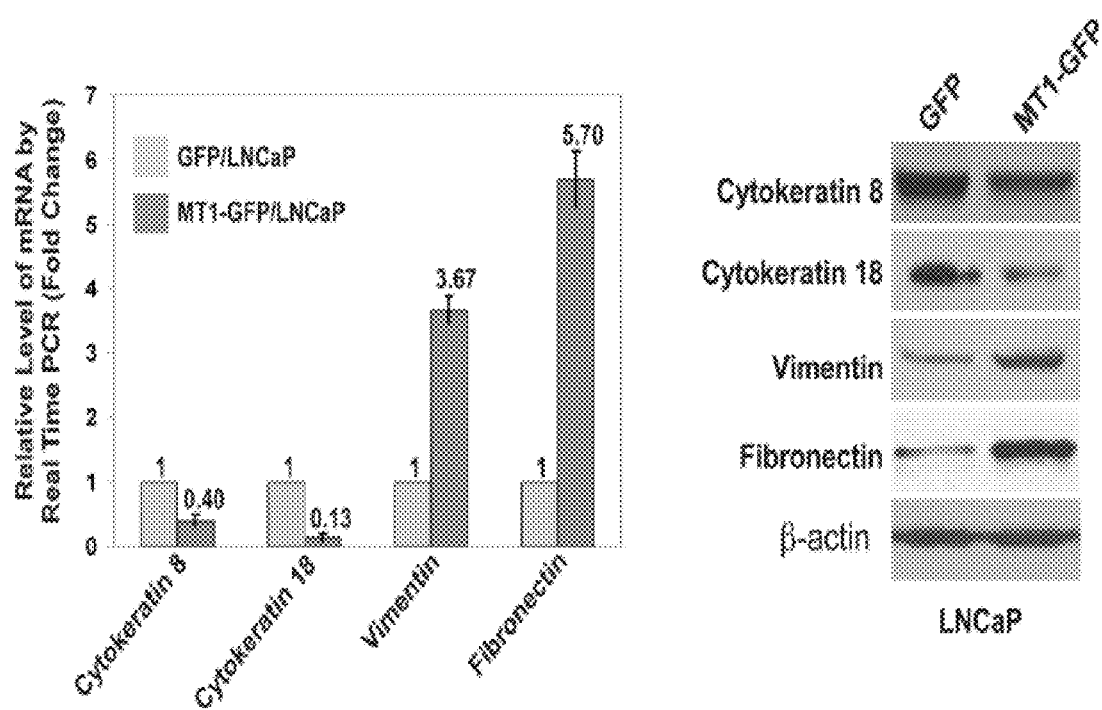
FIG. 19: MT1-MMP induces prostate cancer cell phenotypic changes.
Figure 20:
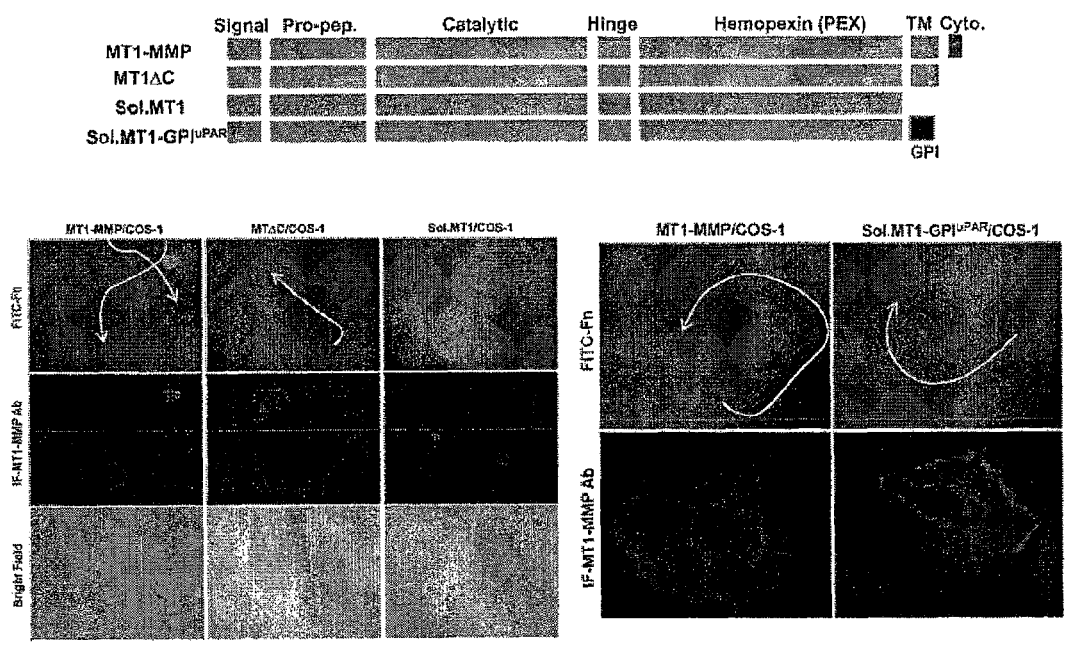
FIG. 20: Nonessential role of the cytoplasmic domain of MT1-MMP in cell migration.
Figure 21:
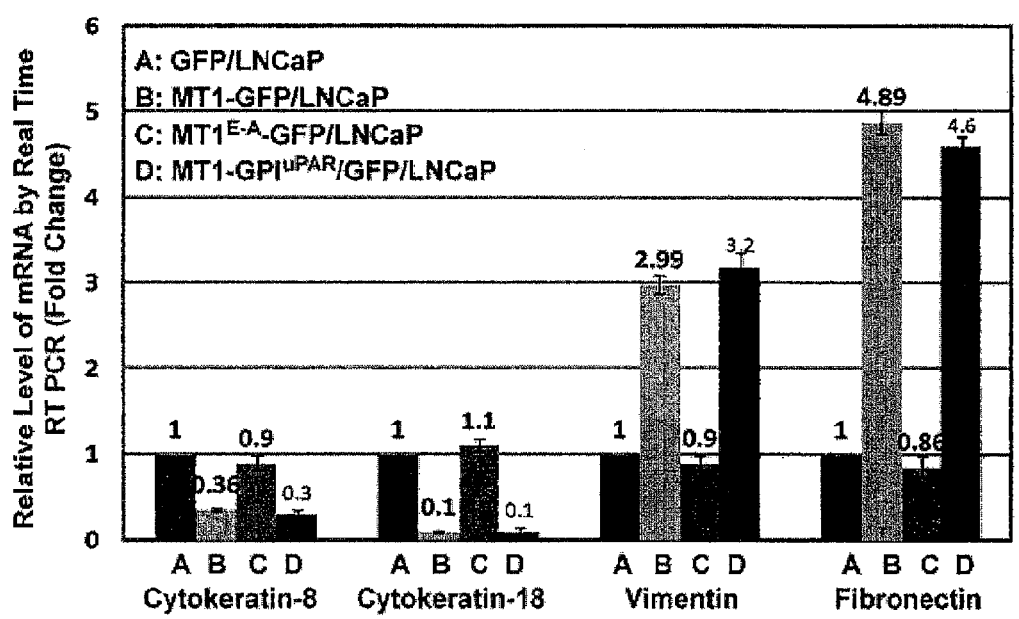
FIG. 21: Functional MT1-MMP is associated with phenotypic changes.
Figure 22:
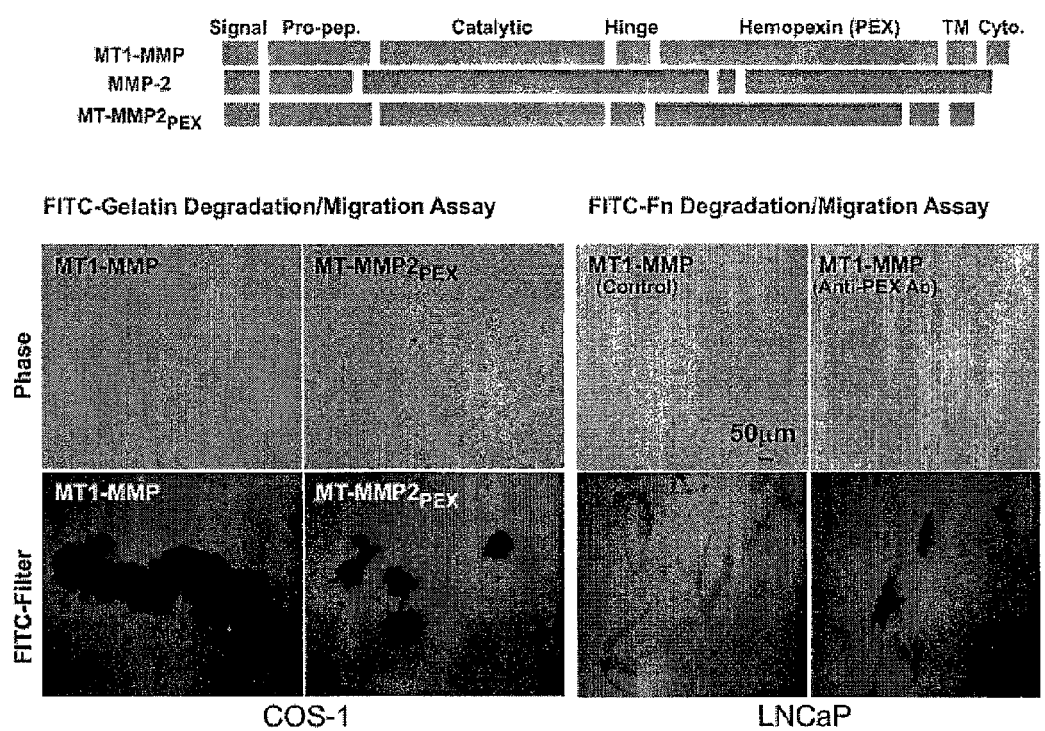
FIG. 22: Role of the hemopexin domain of MT1-MMP in cell migration.
Figure 23:
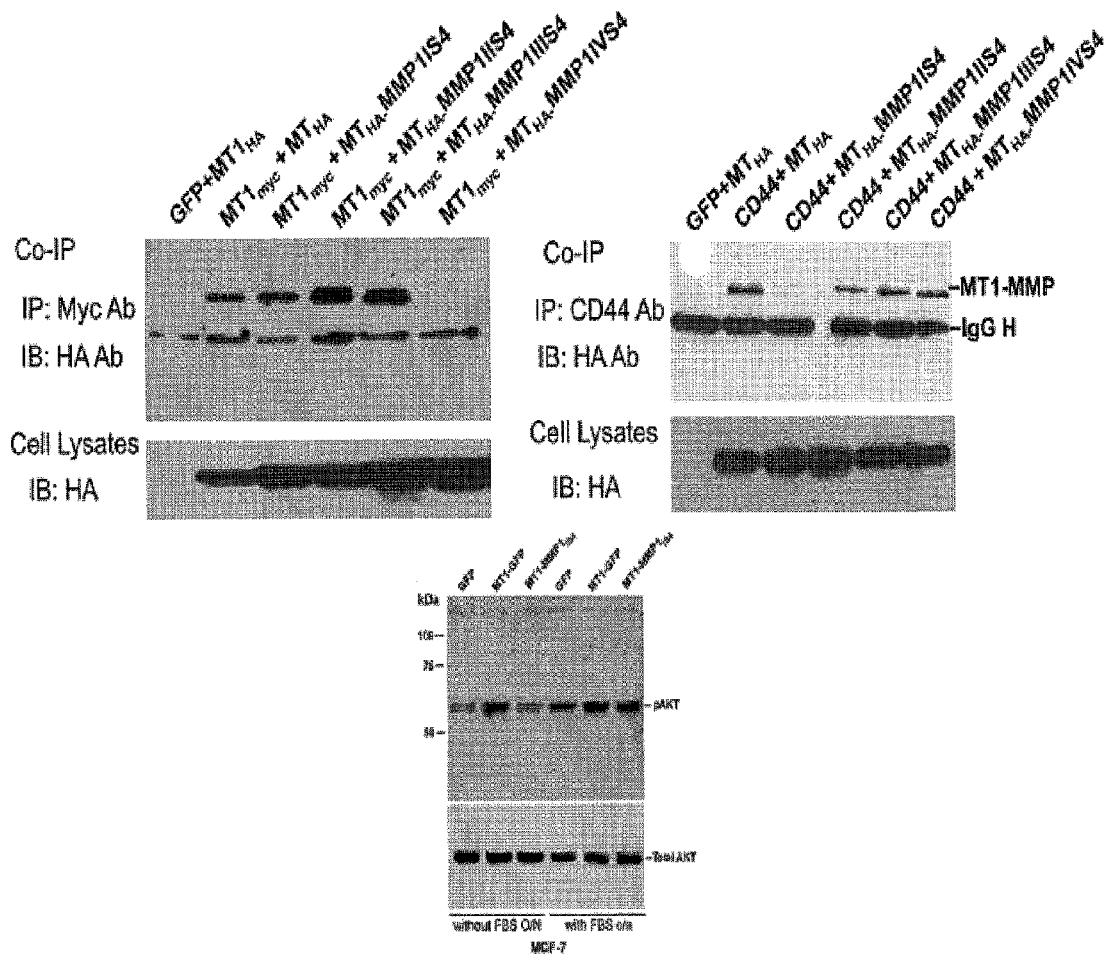
FIG. 23: Requirement of MT1-MMP IS4 and IVS4 for hetero-dimer and homo-dimer formation.
Figure 24:
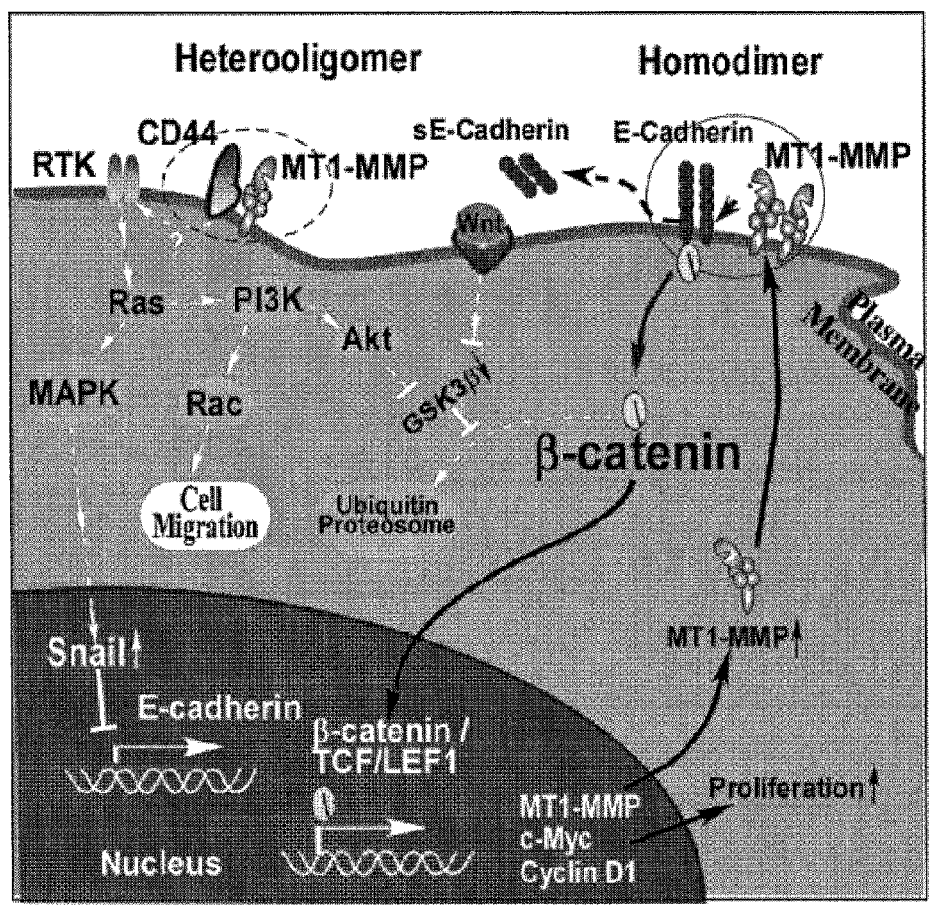
FIG. 24: Hypothetical model of MT1-MMP-induced EMT.
Figure 25:
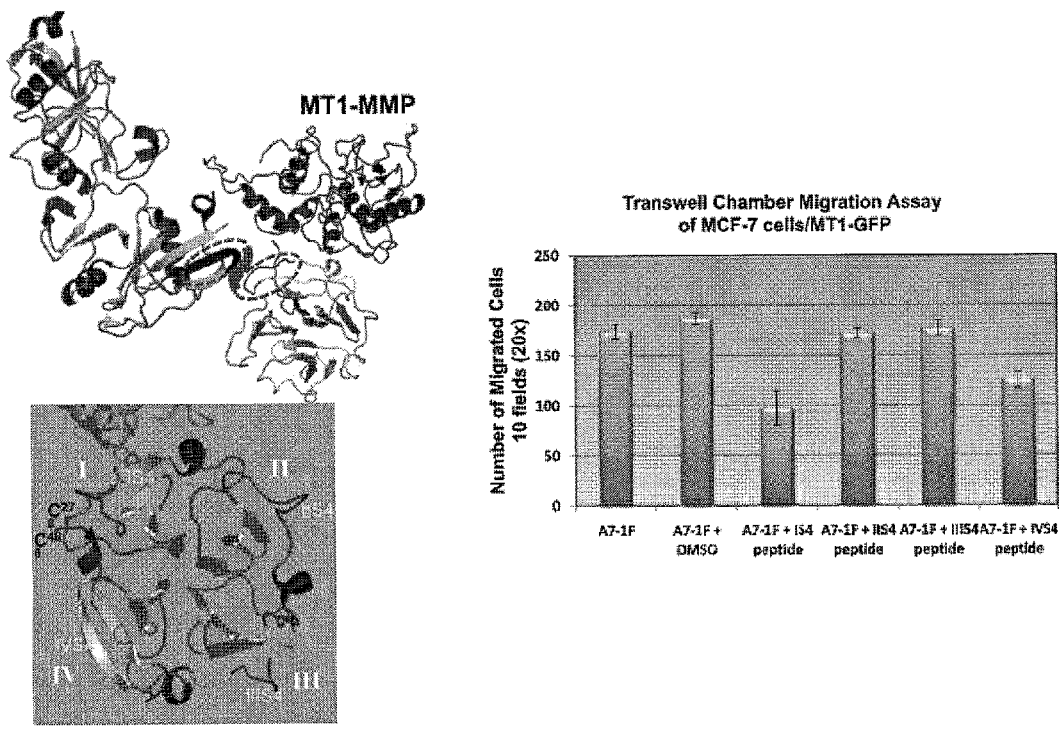
FIG. 25: Structure based peptide design of a competitive inhibitor for MT1-MMP-enhanced cell migration.
Figure 26:
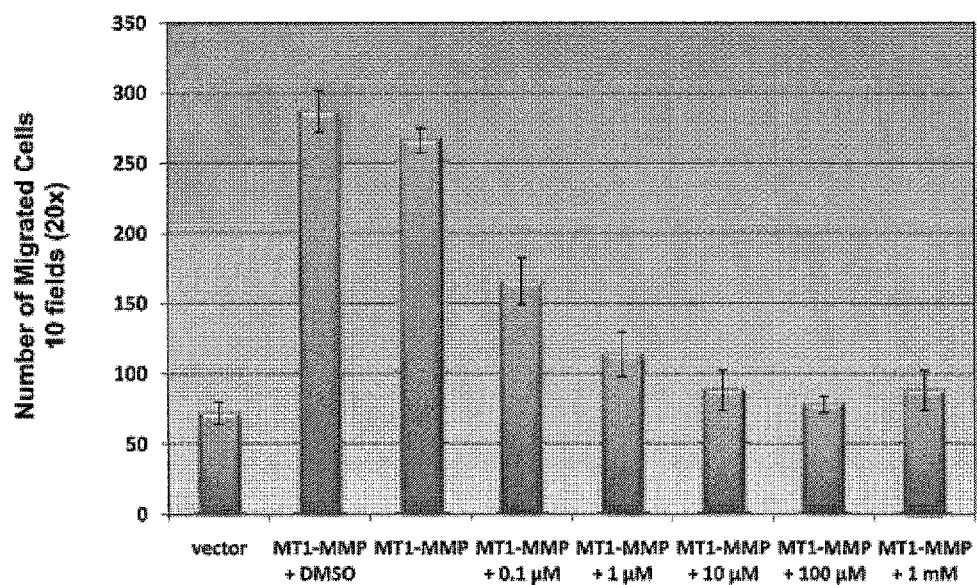
FIG. 26: Dose dependent inhibition of MT1-MMP-enhanced cell migration.
Figure 27:
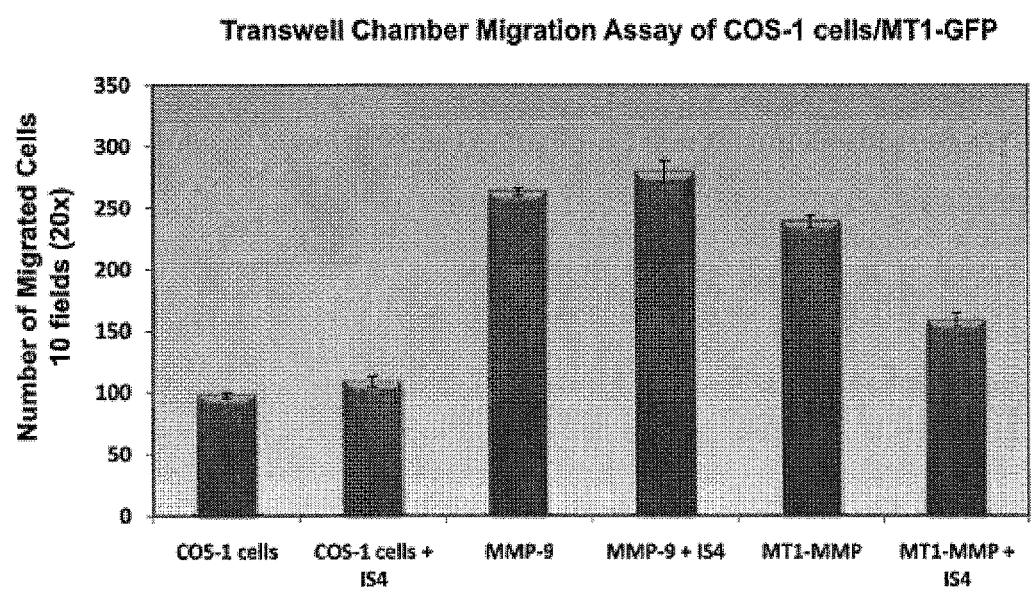
FIG. 27: Specific inhibition of MT1-MMP-enhanced migration by IS4 peptides.

"Matrix metalloproteinases" ("MMPs") are a family of nine or more highly homologous zinc dependent Zn(++)-endopeptidases (FIG. 11) that collectively cleave most if not all of the constituents of the extracellular matrix, and act on pro-inflammatory cytokines, chemokines and other proteins to regulate varied aspects of inflammation and immunity.

MMPs are exemplified by MMP-1, MMP-2, MMP-3, MMP-8, MMP-9 (CL), MMP-10, MMP-11, MMP-12, MMP-13, MMP-18, MMP-19, MMP-20, MMP-22, MMP-26, MMP-27, and MMP-28 (FIG. 11), MT2-MMP, MT3-MMP, MT4-MMP, and MT6-MMP. The MMPs share a common domain structure. The three common domains are the pro-peptide, the catalytic domain and the hemopexin domain that is linked to the catalytic domain by a flexible hinge region.

The MMPs are initially synthesized as inactive zymogens with a "pro-peptide domain" that is removed before the enzyme is active. The pro-peptide domain is part of the "cysteine switch." This contains a conserved cysteine residue that interacts with the zinc in the active site and prevents binding and cleavage of the substrate keeping the enzyme in an inactive form. In the majority of the MMPs, the cysteine residue is in the conserved sequence PRCGxPD (SEQ ID NO:34). The "catalytic domain" is an oblate sphere containing the "active site." In the part of the catalytic domain forming the active site there is a catalytically important $Zn^{2+}$ ion, which is bound by three histidine residues found in the conserved sequence HexxHxxGxxH (SEQ ID NO:35). Hence, this sequence is a zinc-binding motif. The catalytic domain is connected to the C-terminal domain by a flexible "hinge region" (also referred to as "linker region"). This is up to 75 amino acids long, and has no determinable structure. The "hemopexin domain" (also referred to as "PEX domain" and "hemopexin-like domain") is at the C-terminal of the MMP and has structural similarities to the serum protein hemopexin. It has a four bladed beta-propeller structure. Beta-propeller structures provide a large flat surface that is thought to be involved in protein-protein interactions. This determines substrate specificity and is the site for interaction with TIMP's (tissue inhibitor of metalloproteinases). The PEX domain is absent in MMP-7, MMP-23, MMP-26 and the plant and nematode. "Membrane-type matrix metalloproteinases" ("MT-MMPs") are anchored to the plasma membrane via a transmembrane or a GPI-anchoring domain.

The PEX domain of MMPs exhibits similar structures composed of a disc-like shape, with the chain folded into a β-propeller structure that has pseudo four-fold symmetry (75). Each propeller contains a sheet of four antiparallel strands with peptide loops linking one sheet to the next as illustrated in FIG. 43. Only strands 1-3 (S1-S3) within each blade are topologically conserved and can be superimposed (76). The outer strand 4 (S4) of each blade deviates considerably between different MMP PEX domains (76). This suggests that the inner three strands constitute the structural framework of the β-propeller architecture, while the outer strand of each blade mediates contacts with other specific protein components. The PEX domain of MT1-MMP shares 47% to 55% similarity with secreted MMP-1, -2, -9 and -13, and 83% similarity with MT2-MMP (SeqWeb version 2, GCG Wisconsin package). The genetic differences between the PEX domains of MT1-MMP and secreted MMPs determine the distinct role of the PEX domain in cell function. Substitution of the PEX domain of MT1-MMP with that of MT4-MMP, a GPI anchored MMP (5) or MMP-2 (8) abolished MT1-MMP-mediated proMMP-2 activation and cell migration, respectively. Structure-function relationships of the PEX domain in cell migration have not yet been defined.

Based on the similarity of MMP PEX domains, we generated substituted mutations by replacing each blade in the PEX domain of MT1-MMP with that of MMP-1. Mutations of the entire blade I or IV of MT1-MMP resulted in defects in cell migration (Table 1), but not substrate degradation using FITC-labeled gelatin substrate degradation assay. Using a similar approach, we recently identified the outer strands of blade I and IV within the PEX domain of MT1-MMP (IS4: $Asn^{346}$-$Phe^{359}$, and IVS4: $Asn^{488}$-$Gly^{507}$) as critical areas required for MT1-MMP-enhanced cell migration (FIGS. 42 & 44). This invention further defines the minimum motifs within IS4 and IVS4 strands required for MT1-MMP-mediated cell migration. In the absence of a three-dimensional structure of the PEX domain of MT1-MMP, we adopted a computational model of MT1-MMP and to employ a mutagenesis approach to identify critical motif(s) in the PEX domain of MT1-MMP required for cell migration and/or proMMP-2 activation. The success of this experiment provides fundamental evidence to better understand MT1-MMP outside-in signaling required for cell migration and to design sequence-based peptide targeting molecules aimed at inhibiting MT1-MMP-induced cell migration/invasion.

Emerging evidence has emphasized the role of matrix metalloproteinases (MMPs) in early aspects of cancer metastasis. Inhibition of proteolytic activity has been a long-term focus of MMP research. A decade ago, the pharmaceutical industry launched ambitious programs to develop MMP inhibitors (MMPI) for the treatment of cancer. Based on the assumption that degradation of collagen by MMPs is considered to be an essential component in progression from in situ carcinoma to invasive/metastatic cancer, the initial anti-MMP drugs for use in cancer were designed as peptide mimics of the collagen amino-acid sequence surrounding the collagenase cleavage site. These MMPIs bind to the catalytic site of MMPs and interfere with their proteolytic activity. Although these MMPIs were successful in interfering with cancer growth and dissemination in animal models, the use of these broad spectrum MMPIs in randomized clinical trials of patients with advanced cancers showed a lack of efficacy. Since the catalytic domain of all MMPs shares highly conserved sequence, lack of specificity of developed MMP enzymatic inhibitors has hindered MMP inhibitor drug discovery. Based on the lessons learned from MMP inhibitor clinical trials, alternative MMP inhibition strategies, based on blocking cell-surface interactions and activation, should form the basis of future therapies for targeting these enzymes in cancer prevention/treatment. A major conceptual advance in development of novel MMPIs to target non catalytic functions of the proteases.

"Membrane type 1 Matrix Metalloproteinase" and "MT1-MMP" interchangeably refer to a Matrix Metalloproteinase (exemplified in FIG. 47) that contains a C-terminal hemopexin domain. The PEX domain of MT1-MMP contains an IS4 peptide sequence and an IVS4 peptide sequence. The invention's IS4-5 (GYPMP) (SEQ ID NO:4) and IS4-8 (VMDGYPMP) (SEQ ID NO:01) sequences are contained within the IS4 peptide. The invention's (GYPKSALR) (SEQ ID NO:03) is contained within the IVS4 peptide.

B. Exemplary Compositions of the Invention

The invention provides compositions comprising a purified polypeptide that contains an amino acid sequence selected from a) GYPMP (SEQ ID NO:04) (IS4-5, of MT1-MMP, which is contained in the IS4 blade, and which is the minimal amino acid portion of IS4-8 peptide SEQ ID NO:01, b) VMDGYPMP (SEQ ID NO:01) (IS4-8 of MT1-MMP, which is the 8-amino acid sequence that contains at its C-terminal the 5-amino acid portion listed as SEQ ID NO:04), c) GYPKSALR (SEQ ID NO:03) (IVS4-8, contained in the IVS4 blade of MT1-MMP), d) a Matrix metalloproteinase (MMP) sequence corresponding to the GYPMP (SEQ ID NO:04) of the hemopexin (PEX) domain of a membrane type 1 matrix metalloproteinase (MT1-MMP), and e) a MMP sequence corresponding to the VMDGYPMP (SEQ ID NO:01) of the PEX domain of the MT1-MMP, and f) a MMP sequence corresponding to the GYPKSALR (SEQ ID NO:03) of the PEX domain of the MT1-MMP. In preferred embodiments, the polypeptide a) does not comprise a PEX domain of a MMP and/or b) reduces homodimerization of an MMP that contains the amino acid sequence. In particular embodiments, the polypeptide reduces migration of a cell expressing a MMP.

The invention's peptide sequences can be used for in vitro and/or in vivo confirmation of the effect of the invention's polypeptides on migration of different cell types that is mediated by an MMP (e.g., MT1-MMP) and for in vitro and/or in vivo confirmation of the effect of changes in cell migration that is mediated by an MMP (e.g., MT1-MMP) on pathological conditions and/or biochemical processes that involve expression of MMPs. In addition, the invention's peptide sequences can be used to diagnose and to therapeutically intervene in diseases (e.g., cancer metastasis) involving undesired cell migration that is mediated by an MMP (e.g., MT1-MMP).

The terms "peptide," "peptide sequence," "amino acid sequence," "polypeptide," and "polypeptide sequence" are used interchangeably herein to refer to at least two amino acids or amino acid analogs that are covalently linked by a peptide bond or an analog of a peptide bond. The term peptide includes oligomers and polymers of amino acids or amino acid analogs. The term peptide also includes molecules, which are commonly referred to as peptides, which generally contain from about two (2) to about twenty (20) amino acids. The term peptide also includes molecules, which are commonly referred to as polypeptides, which generally contain from about twenty (20) to about fifty amino acids (50). The term peptide also includes molecules, which are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide, which is produced by artificial means in vitro (e.g., was not produced in vivo).

In some embodiments, the invention's peptide sequences are portions of the IS4 region (Table 1) of an MMP.

TABLE 1

Matrix metalloproteinase (MMP) sequences that correspond to MT1-MMP VMDGYPMP (SEQ ID NO: 01) IS4 blade sequence and/or to MT1-MMP GYPMP (SEQ ID NO: 04) IS4 blade sequence

| SEQ ID NO: | Sequence | Matrix metalloproteinase |
|---|---|---|
| 05 | YPEVELNF (0%) | MMP-1 |
| 06 | KPMGPLL (12.5%) | MMP-2 |
| 07 | KLEPELHL (0%) | MMP-3 |
| 08 | LQRVEMNF (0%) | MMP-8 |
| 09 | SRPQGPFL (12.5%) | MMP-9 |
| 10 | NPEPEFHL (0%) | MMP-10 |
| 11 | LQPGYPAL (37.5%) | MMP-11 |
| 12 | RPKTSVNL (0%) | MMP-12 |
| 13 | QVDAELFL (12.5%) | MMP-13 |
| 14 | VLDNYPMP (75%) | MT2-MMP |

TABLE 1 -continued

Matrix metalloproteinase (MMP) sequences that correspond to MT1-MMP VMDGYPMP (SEQ ID NO: 01) IS4 blade sequence and/or to MT1-MMP GYPMP (SEQ ID NO: 04) IS4 blade sequence

| SEQ ID NO: | Sequence | Matrix metalloproteinase |
|---|---|---|
| 15 | VMDGYPMQ (87.5%) | MT3-MMP |
| 16 | LVSLQPAQ (12.5%) | MT4-MMP |
| 17 | LVSPRPAR (12.5%) | MT6-MMP |
| 18 | GPLFR (0%) | MMP-19 |

Thus, in one embodiment, the polypeptide that in one embodiment, the polypeptide that contains GYPMP (SEQ ID NO:04), comprises VMDGYPMP (SEQ ID NO:01) (i.e., IS4-8 of MT1-MMP, which is the 8-amino acid sequence that contains at it C-terminal the 5-amino acid portion SEQ ID NO:04).

In another embodiment, the polypeptide that contains the MMP sequence corresponding to the GYPMP (SEQ ID NO:04) of the PEX domain of the MT1-MMP comprises an amino acid sequence selected from SEQ ID NO:05-18 (Table 1).

In a further embodiment, the polypeptide that contains the MMP sequence corresponding to the VMDGYPMP (SEQ ID NO:01) of the PEX domain of the MT1-MMP comprises an amino acid sequence selected from SEQ ID NO:05-18 (Table 1). In some embodiments, the invention's peptide sequences are portions of the IVS4 region (Table 2) of an MMP.

TABLE 2

Matrix metalloproteinase (MMP) sequences that correspond to MT1-MMP GYPKSALR (SEQ ID NO: 03) IVS4 blade sequence

| SEQ ID NO: | Sequence | Matrix metalloproteinase |
|---|---|---|
| 20 | LQKANS (0%) | MMP-1 |
| 21 | LKSVK (25%) | MMP-2 |
| 22 | TLKSNS (25%) | MMP-3 |
| 23 | VARGNK (0%) | MMP-8 |
| 24 | NQVDQVGY (0%) | MMP-9 |
| 25 | ILKSNS (25%) | MMP-10 |
| 26 | GFPRLVGP (25%) | MMP-11 |
| 27 | TLKSNS (25%) | MMP-12 |
| 28 | VMPANS (12.5%) | MMP-13 |
| 29 | GYPKSILR (87.5%) | MT2-MMP |
| 30 | GHPRSILK (50%) | MT3-MMP |
| 31 | GYPQSTAR (62.5%) | MT4-MMP |
| 32 | DAPQPMGP (0%) | MT6-MMP |
| 33 | GYPRNISH (37.5%) | MMP-19 |

Thus, in a particular embodiment, the polypeptide that contains the MMP sequence corresponding to the GYPK- SALR (SEQ ID NO:03) of the PEX domain of the MT1-MMP comprises an amino acid sequence selected from SEQ ID NO:20-33 (Table 2).

Thus, the invention provides sequences that are derived from MMP-1, wherein the MMP-1 sequence corresponding to one or more of the GYPMP (SEQ ID NO:04), and VMDGYPMP (SEQ ID NO:01), of the PEX domain of the MT1-MMP comprises YPEVELNF (SEQ ID NO:05), and wherein the MMP-1 sequence corresponding to the GYPKSALR (SEQ ID NO:03) of the PEX domain of the MT1-MMP comprises LQKANS (SEQ ID NO:20). These amino acid sequences are useful in reducing MT1-MMP activity, reducing one or more symptoms of a disease (e.g., cancer, and including cancer metastasis) that is associated with expression of MT1-MMP, reducing migration of a cell expressing MT1-MMP, and/or detecting MT1-MMP (e.g., that is expressed by cancer cells).

In another embodiment, the invention provides sequences that are derived from MMP-2, wherein the MMP-2 sequence corresponding to one or more of the GYPMP (SEQ ID NO:04), and VMDGYPMP (SEQ ID NO:01), of the PEX domain of the MT1-MMP comprises KPMGPLL (SEQ ID NO:06), and wherein the MMP-2 sequence corresponding to the GYPKSALR (SEQ ID NO:03) of the PEX domain of the MT1-MMP comprises LKSVK (SEQ ID NO:21). These amino acid sequences are useful in reducing MMP-2 activity, reducing one or more symptoms of a disease (e.g., cancer, and including cancer metastasis) that is associated with expression of MMP-2, reducing migration of a cell expressing MMP-2, and/or detecting MMP-2 (e.g., that is expressed by cancer cells).

In a further embodiment, the invention provides sequences that are derived from MMP-3, wherein the MMP-3 sequence corresponding to one or more of the GYPMP (SEQ ID NO:04), and VMDGYPMP (SEQ ID NO:01), of the PEX domain of the MT1-MMP comprises KLEPELHL (SEQ ID NO:07), and wherein the MMP-3 sequence corresponding to the GYPKSALR (SEQ ID NO:03) of the PEX domain of the MT1-MMP comprises TLKSNS (SEQ ID NO:22). These amino acid sequences are useful in reducing MMP-3 activity, reducing one or more symptoms of a disease (e.g., cancer, and including cancer metastasis) that is associated with expression of MMP-3, reducing migration of a cell expressing MMP-3, and/or detecting MMP-3 (e.g., that is expressed by cancer cells).

In another embodiment, the invention provides sequences that are derived from MMP-8, wherein the MMP-8 sequence corresponding to one or more of the GYPMP (SEQ ID NO:04), and VMDGYPMP (SEQ ID NO:01), of the PEX domain of the MT1-MMP comprises LQRVEMNF (SEQ ID NO:08), and wherein the MMP-8 sequence corresponding to the GYPKSALR (SEQ ID NO:03) of the PEX domain of the MT1-MMP comprises VARGNK (SEQ ID NO:23). These amino acid sequences are useful in reducing MMP-8 activity, reducing one or more symptoms of a disease (e.g., cancer, and including cancer metastasis) that is associated with expression of MMP-8, reducing migration of a cell expressing MMP-8, and/or detecting MMP-8 (e.g., that is expressed by cancer cells).

In a further embodiment, the invention provides sequences that are derived from MMP-9, wherein the MMP-9 sequence corresponding to one or more of the GYPMP (SEQ ID NO:04), and VMDGYPMP (SEQ ID NO:01), of the PEX domain of the MT1-MMP comprises SRPQGPFL (SEQ ID NO:09), and wherein the MMP-9 sequence corresponding to the GYPKSALR (SEQ ID NO:03) of the PEX domain of the MT1-MMP comprises NQVDQVGY (SEQ ID NO:24). These amino acid sequences are useful in reducing MMP-9 activity, reducing one or more symptoms of a disease (e.g., cancer, and including cancer metastasis) that is associated with expression of MMP-9, reducing migration of a cell expressing MMP-9, and/or detecting MMP-9 (e.g., that is expressed by cancer cells).

In yet another embodiment, the invention provides sequences that are derived from MMP-10, wherein the MMP-10 sequence corresponding to one or more of the GYPMP (SEQ ID NO:04), and VMDGYPMP (SEQ ID NO:01), of the PEX domain of the MT1-MMP comprises NPEPEFHL (SEQ ID NO:10), and wherein the MMP-10 sequence corresponding to the GYPKSALR (SEQ ID NO:03) of the PEX domain of the MT1-MMP comprises ILKSNS (SEQ ID NO:25). These amino acid sequences are useful in reducing MMP-10 activity, reducing one or more symptoms of a disease (e.g., cancer, and including cancer metastasis) that is associated with expression of MMP-10, reducing migration of a cell expressing MMP-10, and/or detecting MMP-10 (e.g., that is expressed by cancer cells).

In a further embodiment, the invention provides sequences that are derived from MMP-11, wherein the MMP-11 sequence corresponding to one or more of the GYPMP (SEQ ID NO:04), and VMDGYPMP (SEQ ID NO:01), of the PEX domain of the MT1-MMP comprises LQPGYPAL (SEQ ID NO:11), and wherein MMP-11 sequence corresponding to the GYPKSALR (SEQ ID NO:03) of the PEX domain of the MT1-MMP comprises GFPRLVGP (SEQ ID NO:26). These amino acid sequences are useful in reducing MMP-11 activity, reducing one or more symptoms of a disease (e.g., cancer, and including cancer metastasis) that is associated with expression of MMP-11, reducing migration of a cell expressing MMP-11, and/or detecting MMP-11 (e.g., that is expressed by cancer cells).

In another embodiment, the invention provides sequences that are derived from MMP-12, wherein the MMP-12 sequence corresponding to one or more of the GYPMP (SEQ ID NO:04), and VMDGYPMP (SEQ ID NO:01), of the PEX domain of the MT1-MMP comprises RPKTSVNL (SEQ ID NO:12), and wherein the MMP-12 sequence corresponding to the GYPKSALR (SEQ ID NO:03) of the PEX domain of the MT1-MMP comprises TLKSNS (SEQ ID NO:27). These amino acid sequences are useful in reducing MMP-12 activity, reducing one or more symptoms of a disease (e.g., cancer, and including cancer metastasis) that is associated with expression of MMP-12, reducing migration of a cell expressing MMP-12, and/or detecting MMP-12 (e.g., that is expressed by cancer cells).

In a further embodiment, the invention provides sequences that are derived from MMP-13, wherein the MMP-13 sequence corresponding to one or more of the GYPMP (SEQ ID NO:04), and VMDGYPMP (SEQ ID NO:01), of the PEX domain of the MT1-MMP comprises QVDAELFL (SEQ ID NO:13), and wherein the MMP-28 sequence corresponding to the GYPKSALR (SEQ ID NO:03) of the PEX domain of the MT1-MMP comprises VMPANS (SEQ ID NO:28). These amino acid sequences are useful in reducing MMP-13 activity, reducing one or more symptoms of a disease (e.g., cancer, and including cancer metastasis) that is associated with expression of MMP-13, reducing migration of a cell expressing MMP-13, and/or detecting MMP-13 (e.g., that is expressed by cancer cells).

In another embodiment, the invention provides sequences that are derived from MT2-MMP, wherein the MT2-MMP sequence corresponding to one or more of the GYPMP (SEQ ID NO:04), and VMDGYPMP (SEQ ID NO:01), of the PEX domain of the MT1-MMP comprises VLDNYPMP (SEQ ID NO:14), and wherein the MT2-MMP sequence corresponding to the GYPKSALR (SEQ ID NO:03) of the PEX domain of the MT1-MMP comprises GYPKSILR (SEQ ID NO:29). These amino acid sequences are useful in reducing MT2-MMP activity, reducing one or more symptoms of a disease (e.g., cancer, and including cancer metastasis) that is associated with expression of MT2-MMP, reducing migration of a cell expressing MT2-MMP, and/or detecting MT2-MMP (e.g., that is expressed by cancer cells).

In a further embodiment, the invention provides sequences that are derived from MT3-MMP, wherein the MT3-MMP sequence corresponding to one or more of the GYPMP (SEQ ID NO:04), and VMDGYPMP (SEQ ID NO:01), of the PEX domain of the MT1-MMP comprises VMDGYPMQ (SEQ ID NO:15), and wherein the MT3-MMP sequence corresponding to the GYPKSALR (SEQ ID NO:03) of the PEX domain of the MT1-MMP comprises GHPRSILK (SEQ ID NO:30). These amino acid sequences are useful in reducing MT3-MMP activity, reducing one or more symptoms of a disease (e.g., cancer, and including cancer metastasis) that is associated with expression of MT3-MMP, reducing migration of a cell expressing MT3-MMP, and/or detecting MT3-MMP (e.g., that is expressed by cancer cells).

In another embodiment, the invention provides sequences that are derived from MT4-MMP, wherein the MT4-MMP sequence corresponding to one or more of the GYPMP (SEQ ID NO:04), and VMDGYPMP (SEQ ID NO:01), of the PEX domain of the MT1-MMP comprises LVSLQPAQ (SEQ ID NO:16), and wherein the MT4-MMP sequence corresponding to the GYPKSALR (SEQ ID NO:03) of the PEX domain of the MT1-MMP comprises GYPQSTAR (SEQ ID NO:31). These amino acid sequences are useful in reducing MT4-MMP activity, reducing one or more symptoms of a disease (e.g., cancer, and including cancer metastasis) that is associated with expression of MT4-MMP, reducing migration of a cell expressing MT4-MMP, and/or detecting MT4-MMP (e.g., that is expressed by cancer cells).

In yet a further embodiment, the invention provides sequences that are derived from MT6-MMP, wherein the MT6-MMP sequence corresponding to one or more of the GYPMP (SEQ ID NO:04), and VMDGYPMP (SEQ ID NO:01), of the PEX domain of the MT1-MMP comprises LVSPRPAR (SEQ ID NO:17), and wherein the MT6-MMP sequence corresponding to the GYPKSALR (SEQ ID NO:03) of the PEX domain of the MT1-MMP comprises DAPQPMGP (SEQ ID NO:32). These amino acid sequences are useful in reducing MT6-MMP activity, reducing one or more symptoms of a disease (e.g., cancer, and including cancer metastasis) that is associated with expression of MT6-MMP, reducing migration of a cell expressing MT6-MMP, and/or detecting MT6-MMP (e.g., that is expressed by cancer cells).

In another embodiment, the invention provides sequences that are derived from MMP-19, wherein the MMP-19 sequence corresponding to one or more of the GYPMP (SEQ ID NO:04), and VMDGYPMP (SEQ ID NO:01), of the PEX domain of the MT1-MMP comprises GPLFR (SEQ ID NO:18), and wherein the MMP-19 sequence corresponding to the GYPKSALR (SEQ ID NO:03) of the PEX domain of the MT1-MMP comprises GYPRNISH (SEQ ID NO:33). These amino acid sequences are useful in reducing MMP-19 activity, reducing one or more symptoms of a disease (e.g., cancer, and including cancer metastasis) that is associated with expression of MMP-19, reducing migration of a cell expressing MMP-19, and/or detecting MMP-19 (e.g., that is expressed by cancer cells).

The invention's peptides may be derivative peptides. The terms "derivative" or "modified" when used in reference to a peptide mean that the peptide contains at least one derivative amino acid. A "derivative" of an amino acid and a "modified" amino acid is a chemically modified amino acid. Derivative amino acids can be "biological" or "non-biological" amino acids. Chemical derivatives of one or more amino acid members may be achieved by reaction with a functional side group. Illustrative derivatized molecules include for example those molecules in which free amino groups have been derivatized to form amine hydrochlorides, p-toluene sulfonyl groups, carboxybenzoxy groups, t-butyloxycarbonyl groups, chloroacetyl groups or formyl groups. Free carboxyl groups may be derivatized to form salts, methyl and ethyl esters or other types of esters and hydrazides. Free hydroxyl groups may be derivatized to form O-acyl or O-alkyl derivatives. The imidazole nitrogen of histidine may be derivatized to fond N-im-benzylhistidine. Also included as chemical derivatives are those peptides, which contain naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine, and ornithine for lysine. Other included modifications are amino terminal acylation (e.g., acetylation or thioglycolic acid amidation), terminal carboxylamidation (e.g., with ammonia or methylamine), and similar terminal modifications. In one embodiment, peptides of the present invention are modified to resist proteolysis. Terminal modifications are useful, as is well known, to reduce susceptibility by (i.e. increases resistance to) proteinase (or protease) digestion and therefore to prolong the half-life of the peptides in solutions, particularly in biological fluids where proteases may be present. Exemplary modified amino acids include, without limitation, 2-Aminoadipic acid, 3-Aminoadipic acid, beta-Alanine, beta-Aminopropionic acid, 2-Aminobutyric acid, 4-Aminobutyric acid, piperidinic acid, 6-Aminocaproic acid, 2-Aminoheptanoic acid, 2-Aminoisobutyric acid, 3-Aminoisobutyric acid, 2-Aminopimelic acid, 2,4-Diaminobutyric acid, Desmosine, 2,2'-Diaminopimelic acid, 2,3-Diaminopropionic acid, N-Ethylgilycine, N-Ethylasparagine, Hydroxylysine, allo-Hydroxylysine, 3-Hydroxyproline, 4-Hydroxyproline, Isodesmosine, allo-Isoleucine, N-Methylglycine, sarcosine, N-Methylisoleucine, N-Methylavaline, Norvaline, Norleucine, and Ornithine. Derivatives also include peptides containing one or more additions or deletions as long as the requisite activity is maintained.

The amino acids of the peptides are contemplated to include biological amino acids as well as non-biological amino acids. Accordingly, as used herein, the term "biological amino acid" refers to any one of the known 20 coded amino acids that a cell is capable of introducing into a polypeptide translated from an mRNA. The term "non-biological amino acid," as used herein, refers to an amino acid that is not a biological amino acid. Non-biological amino acids are useful, for example, because of their stereochemistry or their chemical properties. The non-biological amino acid norleucine, for example, has a side chain similar in shape to that of methionine. However, because it lacks a side chain sulfur atom, norleucine is less susceptible to oxidation than methionine. Other examples of non-biological amino acids include aminobutyric acids, norvaline and allo-isoleucine, that contain hydrophobic side chains with different steric properties as compared to biological amino acids.

Peptides that are useful in the instant invention may be synthesized by several methods, including chemical synthesis and recombinant DNA techniques. Synthetic chemistry techniques, such as solid phase Merrifield synthesis are preferred for reasons of purity, freedom from undesired side products, ease of production, etc. A summary of the techniques available are found in several articles, including Steward et al., Solid Phase Peptide Synthesis, W. H. Freeman, Co., San Francisco (1969); Bodanszky, et al., Peptide Synthesis, John Wiley and Sons, Second Edition (1976); J. Meienhofer, Hormonal Proteins and Peptides, 2:46, Academic Press (1983); Merrifield, Adv. Enzymol. 32:221-96 (1969); Fields, et al., Intl. Peptide Protein Res., 35:161-214 (1990), and U.S. Pat. No. 4,244,946 for solid phase peptide synthesis; and Schroder et al., The Peptides, Vol 1, Academic Press (New York) (1965) for classical solution synthesis. Protecting groups usable in synthesis are described as well in Protective Groups in Organic Chemistry, Plenum Press, New York (1973). Solid phase synthesis methods consist of the sequential addition of one or more amino acid residues or suitably protected amino acid residues to a growing peptide chain. Either the amino or carboxyl group of the first amino acid residue is protected by a suitable selectively removable protecting group. A different, selectively removable protecting group is utilized for amino acids containing a reactive side group such as lysine.

The resultant exemplary linear peptides may then be reacted to form their corresponding cyclic peptides. A method for cyclizing peptides is described in Zimmer, et al., Peptides, 393-394 (1992), ESCOM Science Publishers, B.V., 1993. To cyclize peptides containing two or more cysteines through the formation of disulfide bonds, the methods described by Tam et al., J. Am. Chem. Soc., 113:6657-6662 (1991); Plaue, Int. J. Peptide Protein Res., 35:510-517 (1990); Atherton, J. Chem. Soc. Trans. 1:2065 (1985); B. Kamber, et al., Helv. Chim. Acta 63:899 (1980) are useful in some embodiments. Polypeptide cyclization is a useful modification to generate modified peptides (e.g., peptidomimetics) because of the stable structures formed by cyclization and in view of the biological activities observed for cyclic peptides.

Alternatively, selected peptides that are useful in the present invention are produced by expression of recombinant DNA constructs prepared in accordance with well-known methods once the peptides are known. Such production can be desirable to provide large quantities or alternative embodiments of such compounds. Production by recombinant means may be more desirable than standard solid phase peptide synthesis for peptides of at least 8 amino acid residues. The DNA encoding the desired peptide sequence is preferably prepared using commercially available nucleic acid synthesis methods. Following these nucleic acid synthesis methods, DNA is isolated in a purified form that encodes the peptides. Methods to construct expression systems for production of peptides in recombinant hosts are also generally known in the art. Preferred recombinant expression systems, when transformed into compatible hosts, are capable of expressing the DNA encoding the peptides. Other preferred methods used to produce peptides comprise culturing the recombinant host under conditions that are effective to bring about expression of the encoding DNA to produce the peptide of the invention and ultimately to recover the peptide from the culture.

Expression can be effected in either procaryotic or eukaryotic hosts. Prokaryotes most frequently are represented by various strains of *E. coli*. However, other microbial strains may also be used, such as bacilli, for example *Bacillus subtilis*, various species of *Pseudomonas*, or other bacterial strains. In such procaryotic systems, plasmid vectors that contain replication sites and control sequences derived from a species compatible with the host are used. For example, a workhorse vector for *E. coli* is pBR322 and its derivatives. Commonly used procaryotic control sequences, which contain promoters for transcription initiation, optionally with an operator, along with ribosome binding-site sequences, include such commonly used promoters as the beta-lactamase (penicillinase) and lactose (lac) promoter systems, the tryptophan (trp) promoter system, and the lambda-derived PL promoter and N-gene ribosome binding site. However, any available promoter system compatible with procaryote expression can be used.

In one embodiment, the invention's compositions are pharmaceutical compositions. The terms "pharmaceutical" and "physiologically tolerable" composition refers to a composition that contains pharmaceutically acceptable molecules, i.e., molecules that are capable of administration to or upon a subject and that do not substantially produce an undesirable effect such as, for example, adverse or allergic reactions, dizziness, gastric upset, toxicity and the like, when administered to a subject. Preferably also, the pharmaceutically acceptable molecule does not substantially reduce the activity of the invention's compositions. Pharmaceutical molecules include, but are not limited to excipients and diluents.

An "excipient" is an inactive substance used as a carrier for the invention's compositions that may be useful for delivery, absorption, bulking up to allow for convenient and accurate dosage of the invention's compositions. Excipients include, without limitation, antiadherents, binders (e.g., starches, sugars, cellulose, modified cellulose such as hydroxyethyl cellulose, hydroxypropyl cellulose and methly cellulose, lactose, sugar alcohols such as xylitol, sorbital and maltitol, gelatin, polyvinyl pyrrolidone, polyethylene glycol), coatings (e.g., shellac, corn protein zein, polysaccharides), disintegrants (e.g., starch, cellulose, crosslinked polyvinyl pyrrolidone, sodium starch glycolate, sodium carboxymethyl cellulosemethylcellulose), fillers (e.g., cellulose, gelatin, calcium phosphate, vegetable fats and oils, and sugars, such as lactose), diluents, flavors, colors, glidants (e.g., silicon dioxide, talc), lubricants (e.g., talc, silica, fats, stearin, magnesium strearate, steaic acid), preservatives (e.g., antioxidants such as vitamins A, E, C, selenium, cystein, methionine, citric acids, sodium citrate, methyl papaben, propyl paraben), sorbents, sweetners (e.g., syrup). In one embodiment, the excipient comprises HEC (hydroxyethylcellulose), which is a nonionic, water-soluble polymer that can thicken, suspend, bind, emulsify, form films, stabilize, disperse, retain water, and provide protective colloid action. HEC is non-inflammatory and has been used as a delivery vehicle for vaginal microbicides (Tien et al., AIDS Research & Human Retroviruses, (2005). 21:845).

Exemplary "diluents" include water, saline solution, human serum albumin, oils, polyethylene glycols, aqueous dextrose, glycerin, propylene glycol or other synthetic solvents.

C. Conjugates of the Invention's Peptide Sequences Linked to Cytotoxic Agents and/or to Prodrugs The invention contemplates that in some embodiments, e.g. therapeutic uses, the invention's peptide sequences are covalently linked to a cytotoxic agent and/or a prodrug of a cytotoxic agent.

"Cytotoxic agent" refers any agent that is capable of reducing the growth of, and/or killing, a target cell. A "prodrug" is an analog of a cytotoxic agent that substantially lacks cytotoxic activity until subjected to an activation step. Activation steps may include enzymatic cleavage, a chemical activation step such as exposure to a reductant, or a physical activation step such as photolysis.

The covalent linkage between the invention's peptide sequences and the cytotoxic agent or prodrug can include cleavable linkages such as disulfide bonds, which may advantageously result in cleavage of the covalent linkage within the reducing environment of the target cell. Such conjugates are useful as tumor-cell specific therapeutic agents.

In one embodiment, the cytotoxic agent is a small drug molecule (Payne et al., U.S. Pat. No. 7,202,346). In another embodiment, the cytotoxic agent a maytansinoid, an analog of a maytansinoid, a prodrug of a maytansinoid, or a prodrug of an analog of a maytansinoid (U.S. Pat. Nos. 6,333,410; 5,475,092; 5,585,499; 5,846,545; 7,202,346). In another embodiment, the cytotoxic agent may be a taxane (see U.S. Pat. Nos. 6,340,701 & 6,372,738 & 7,202,346) or CC-1065 analog (see U.S. Pat. Nos. 5,846,545; 5,585,499; 5,475,092 & 7,202,346).

In another embodiment, the cytotoxic agent is exemplified by an auristatin, a DNA minor groove binding agent, a DNA minor groove alkylating agent, an enediyne, a duocarmycin, a maytansinoid, and a vinca alkaloid (U.S. Pat. No. 7,662,387).

In a further embodiment, the cytotoxic agent is an antitubulin agent (U.S. Pat. No. 7,662,387). In yet another embodiment, the cytotoxic agent is exemplified by dimethylvaline-valine-dolaisoleuine-dolaproine-phenylalanine-p-phenylenediamine (AFP), dovaline-valine-dolaisoleunine-dolaproine-phenylalanine (MMAF), and monomethyl auristatin E (MAE) (U.S. Pat. No. 7,662,387).

In an additional embodiment the toxic agent is exemplified by radioisotope emitting radiation, immunomodulator, lectin, and toxin (U.S. Pat. No. 6,429,295). In particular, the radioisotope emitting radiation is an alpha-emitter selected from $^{212}$Bi, $^{213}$Bi, and $^{211}$At, or a beta-emitter selected from $^{186}$Re and $^{90}$Y, or a gamma-emitter $^{131}$I (U.S. Pat. No. 7,666,425).

In an alternative embodiment, the toxin is exemplified by ricin, the A-chain of ricin, and pokeweed antiviral protein (U.S. Pat. No. 5,057,313).

In yet another embodiment, the cytotoxic agent is an anticancer drug selected from methotrexate, 5-fluorouracil, cycloheximide, daunomycin, doxorubicin, chlorambucil, trenimon, phenylenediamine mustard, adriamycin, bleomycin, cytosine arabinoside or Cyclophosphamide (U.S. Pat. No. 5,057,313).

D. Exemplary Uses of the Invention's Compositions, Including Therapeutic Applications The invention's compositions may be used in a method for reducing one or more symptoms of a disease associated with expression of a matrix metalloproteinase (MMP), comprising a) providing i) a mammalian subject in need of reducing one or more symptoms of the disease, and ii) any one or more of the compositions disclosed herein, and b) administering to the subject a therapeutic amount of the composition to produce a treated subject, wherein the administering is under conditions for reducing one or more symptoms of the disease. In some embodiments, the methods may further comprise detecting a reduction in one or more symptoms of the disease in the treated subject.

The term "administering" when in reference to a polypeptide, means providing the polypeptide to a subject. This may be done using methods known in the art (e.g., Erickson et al., U.S. Pat. No. 6,632,979; Furuta et al., U.S. Pat. No. 6,905,839; Jackobsen et al., U.S. Pat. No. 6,238,878; Simon et al., U.S. Pat. No. 5,851,789). The invention's compositions may be administered prophylactically (i.e., before the observation of disease symptoms) and/or therapeutically (i.e., after the observation of disease symptoms). Administration also may be concomitant with (i.e., at the same time as, or during) manifestation of one or more disease symptoms. Also, the invention's compositions may be administered before, concomitantly with, and/or after administration of another type of drug or therapeutic procedure (e.g., surgery). Methods of administering the invention's compositions include, without limitation, administration in parenteral, oral, intraperitoneal, intranasal, topical and sublingual forms. Parenteral routes of administration include, for example, subcutaneous, intravenous, intramuscular, intrasternal injection, and infusion routes.

In one embodiment, the invention's compositions comprise a lipid for delivery as liposomes. Methods for generating such compositions are known in the art (Borghouts et al. (2005). J Pept Sci 11, 713-726; Chang et al. (2009) PLoS One 4, e4171; Faisal et al. (2009) Vaccine 27, 6537-6545; Huwyler et al. (2008) Int J Nanomedicine 3, 21-29; Song et al. (2008) Int J Pharm 363, 155-161; Voinea et al. J Cell Mol Med 6, 465-474).

A "subject" and "animal" that may benefit from the invention's methods interchangeably includes any multicellular animal, preferably a mammal. Mammalian subjects include humans, non-human primates, murines, ovines, bovines, ruminants, lagomorphs, porcines, caprines, equines, canines, felines, ayes, etc.). Thus, mammalian subjects are exemplified by mouse, rat, guinea pig, hamster, ferret and chinchilla.

"Subject in need of reducing one or more symptoms of" a disease, e.g., in need of reducing cancer metastasis and/or in need of reducing one or more symptoms of cancer, includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable).

The invention's compositions are administered to a subject in a therapeutically effective amount. As used herein the terms "therapeutically effective amount" and "protective amount" of a composition with respect to HIV infection refer to, in one embodiment, an amount of the composition that delays, reduces, palliates, ameliorates, stabilizes, prevents and/or reverses one or more symptoms of a disease, compared to in the absence of the composition of interest. Examples include, without limitation, tumor size and/or tumor number in cancer disease, glucose levels in blood and/or urine in diabetes, standard biochemical kidney function tests in kidney disease, etc. The term "delaying" symptoms refers to increasing the time period between exposure to the immunogen or virus and the onset of one or more symptoms of the exposure. The term "eliminating" symptoms refers to 100% reduction of one or more symptoms.

Specific dosages (i.e., amounts) that are encompassed by the "pharmaceutically effective amount," "therapeutically effective amount" and "protective amount" can be readily determined by clinical trials and depend, for example, on the route of administration, patient weight (e.g. milligrams of drug per kg body weight), the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors that those skilled in the art will recognize. The dosage and frequency are selected to create an effective level of the compound without substantially harmful effects.

A pharmaceutically effective amount may be determined using in vitro and in vivo assays known in the art and disclosed herein.

Indeed, the invention's methods are useful in any disease that involves MMP-induced cell migration, such as migration of a cancer cell. In one embodiment, the disease is exemplified by cancer (e.g., cancer metastasis), systemic lupus erythematosus (SLE), Sjogren's syndrome (SS), systemic sclerosis (SS), polymyositis, rheumatoid arthritis (RA), multiple sclerosis (MS), atherosclerosis, cerebral ischemia, abdominal aortic aneurysm (AAA), myocardial infarction (MI), cerebral amyloid angiopathy (CAA), angiogenesis, inflammation, ectopic eczema, and contact eczema.

Cancer that may be ameliorated using the invention's methods and compositions include, for example, carcinomas 231, MDA-435, HT-1080, LNCaP, DU145, PC3, TK4, C-1H, C-26, Co-3, HT-29, KM12SM, 253F B-V), etc.

In yet another embodiment, the invention's methods are useful in reducing symptoms of disease associated with expression of a matrix metalloproteinase (MMP). The term "disease associated with cell expression of a matrix metalloproteinase (MMP)" refers to a disease having one or more symptoms that are caused, in whole or in part, by cell expression of a MMP. These diseases include diseases that involve MMP-induced cell migration, such as migration of an endothelial cell, leukocyte cell (including neutrophils, dendritic cells, macrophages, eosinophils, mast cells, T lymphocytes, Langerhans' cells (LCs), etc.), fibroblast cell, osetoclast cell, osteoblast cell, etc.

Table 3 lists exemplary cells whose migration may be altered by the invention's compositions, thereby resulting in a reduction of one or more symptoms of the associated pathological condition.

TABLE 3

Exemplary cells and pathological conditions

| Cell | Pathological condition |
|---|---|
| Cancer cells (including metastatic cancer cells), cancer cell lines, e.g., MCF-7, MDA-MB-231, MDA-435, HT-1080, LNCaP, DU145, PC3, TK4, C-1H, C-26, Co-3, HT-29, KM12SM, 253F B-V | Cancer and cancer metastasis (e.g., Bjorklund et al. (2005) Biochimica et Biophysica Acta 1755: 37-69) |
| Neutrophils, macrophages, T cells | Systemic lupus erythematosus (SLE) |
| White blood cells | Sjogren's syndrome (SS) |
| Fibroblasts | Systemic sclerosis (SS) |
| T lymphocytes | Polymyositis |
| Neutrophils, macrophages, T cells, osteoclasts, | Rheumatoid arthritis (RA) |
| T cells, macrophages | Multiple sclerosis (MS) |
| Macrophages, T lymphocytes, endothelial cells | Atherosclerosis |
| Endothelial cells, macrophages | Cerebral ischemia |
| Macrophages | Abdominal aortic aneurysm (AAA) |
| Leukocytes, macrophages | Myocardial infarction (MI) |
| Endothelial cells, macrophages | Cerebral amyloid angiopathy (CAA) |
| Endothelial cell | Angiogenesis (Bjorklund et al. (2005)) |
| Leukocytes (including neutrophils, dendritic cells, macrophages, eosinophils, mast cells and lymphocytes) | Inflammation (Bjorklund et al. (2005)) |
| Leukocytes (including Langerhans' cells (LCs) | Ectopic eczema, contact eczema (Msika, patent application us 2004/0067910, filed Aug. 25, 2003) | such as lung cancer, breast cancer, prostate cancer, cervical cancer, pancreatic cancer, colon cancer, ovarian cancer; stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia. Malignant neoplasms are further exemplified by sarcomas (such as osteosarcoma and Kaposi's sarcoma). In a particular embodiment, the cancer is exemplified by cancer of the breast, brain and CNS, gastrointestine, head and neck, kidney, lung, lymphoma, melanoma, ovary, sarcoma, neuroblastoma, and lymphoblastic cancer.

In another particular embodiment, the cancer cell is a metastatic cancer cell, cancer cell line (e.g. MCF-7, MDA-MB- The invention's methods may further comprise c) detecting a reduction in one or more symptoms of the disease in the treated subject. In one embodiment, the one or more symptoms of the disease comprise increased cell migration in the presence of MMP compared to in the absence of MMP.

Figure 2:
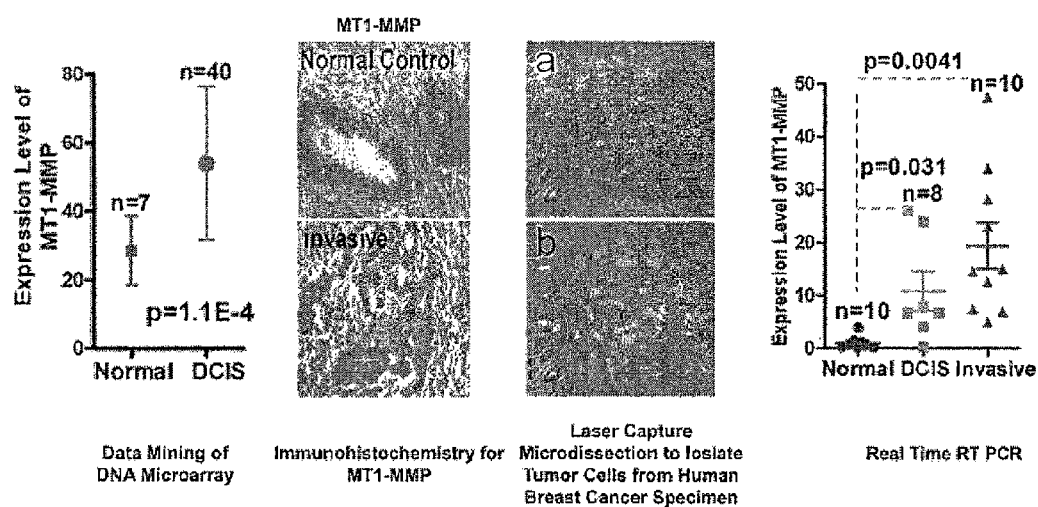
FIG. 2: Upregulated MT1-MMP expression in human breast cancer tissues.
Figure 3:
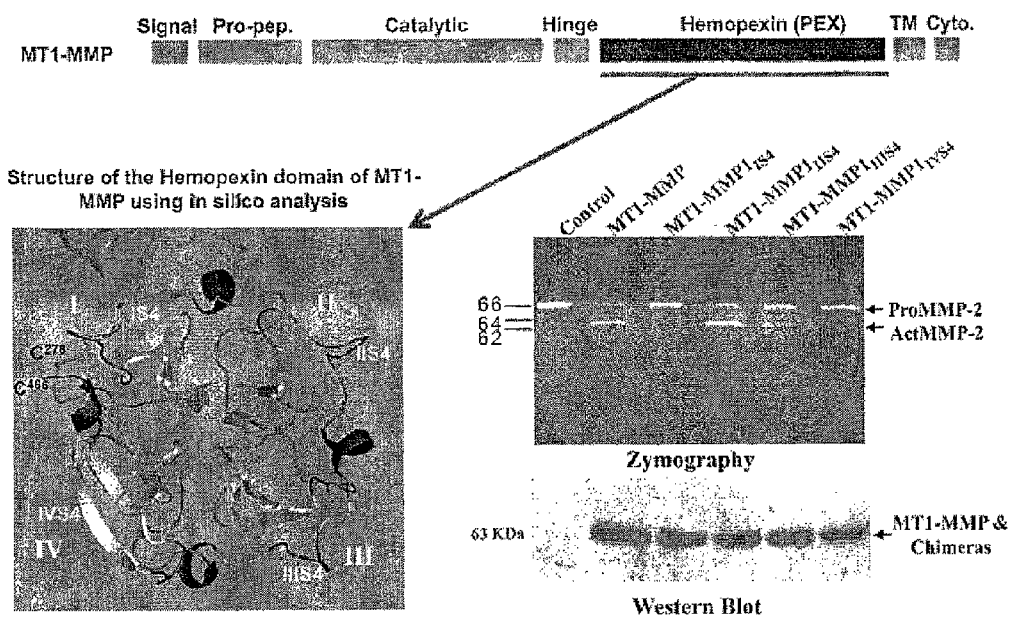
FIG. 3: Strand four of blade I and IV are required for functional MT1-MMP.

"Migration," "migrating," "motility" and grammatical equivalents when used in reference to a cell, interchangeably refer to the spatial movement of a cell on a 2-dimensional substrate (such as a solid substrate, or on a feeder layer of cells on a solid substrate), and/or within a 3-dimensional matrix (such as within a 3-dimensional collagen matrix). Methods for determining the level of cell migration are known in the art, such as wound induced migration assay (e.g., Ezhilarasan et al. (2009) Int. J. Cancer 125:306-315), and disclosed herein, such as transwell migration assay (Example 3, FIG. 2 & Example 4, FIG. 3)

In one embodiment, the therapeutic amount of the invention's composition specifically reduces the cell migration. The term "specifically reduces" when in reference to the level of a particular compound (e.g., the invention's polypeptides)

and/or particular phenomenon (e.g., MMP-induced cell migration)" means the preferential reduction (i.e., a statistically significant reduction) in the level of the particular compound and/or particular phenomenon as compared to the level of another compound and/or phenomenon.

In one embodiment, one or more symptoms of the disease comprise increased cell migration in the presence of an MMP compared to in the absence of an MMP.

In addition to using the invention's polypeptides in reduced symptoms of disease associated with expression of one or more MMP, these polypeptides may additionally be used in a method for reducing cell migration, comprising a) providing i) a cell expressing a matrix metalloproteinase (MMP), and ii) any one or more of the compositions disclosed herein, and b) administering the composition to the cell under conditions for reducing migration of the cell. These methods can be used for in vitro and/or in vivo confirmation of the effect of the invention's polypeptides on migration of different cell types, and the effect of changes in cell migration on pathological conditions and/or biochemical processes. In some embodiments, the method further comprises c) detecting reduced migration of the cell. The cell expressing MMP may be in vivo or in vitro.

Figure 7:
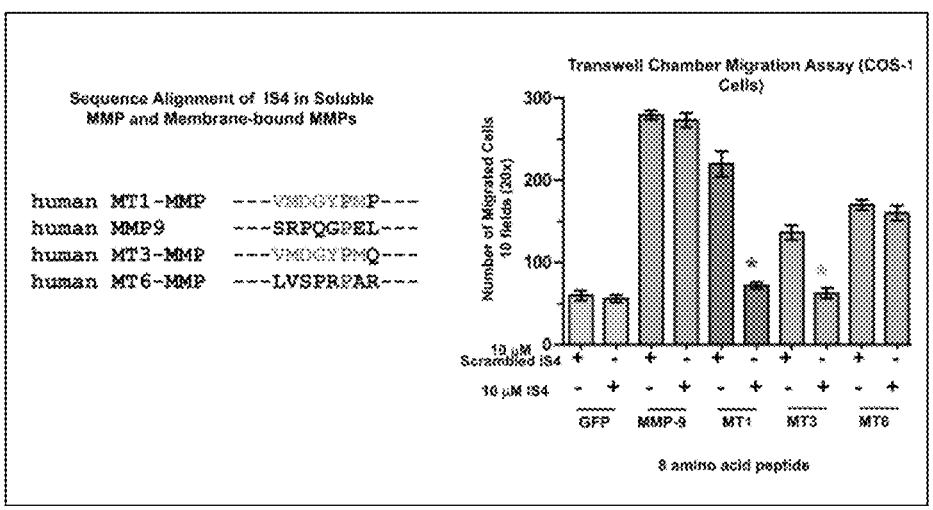
FIG. 7: Specificity of MT1-MMP inhibitory peptides.
Figure 8:
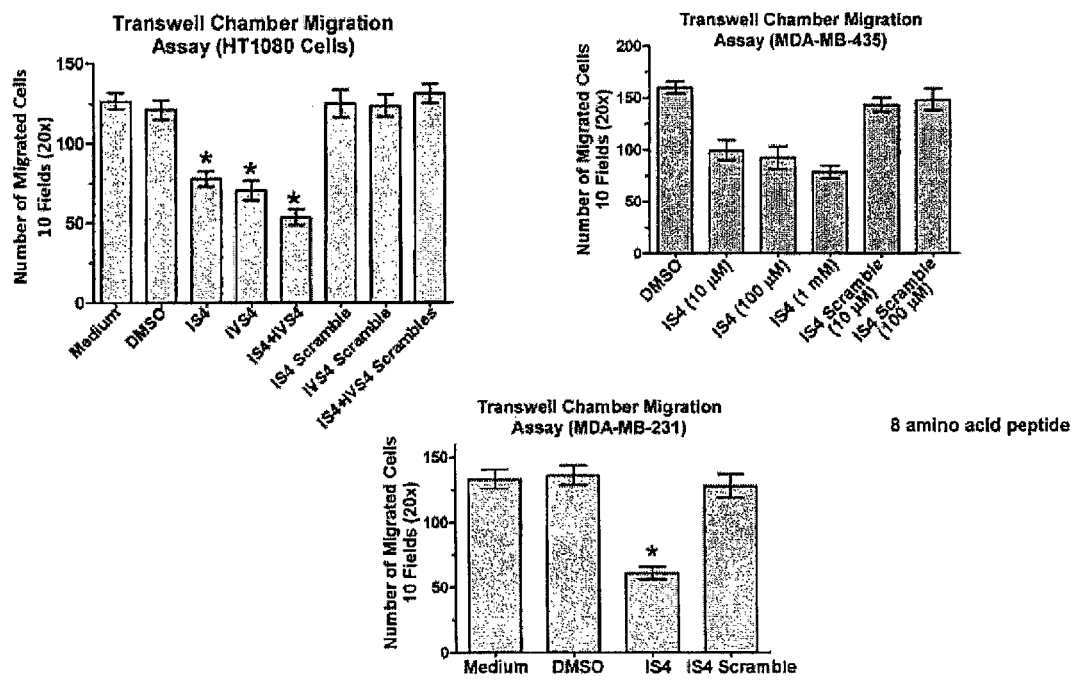
FIG. 8: Inhibition of migration of cancer cells expressing endogenous MT1-MMP by IS4 peptides.
Figure 9:
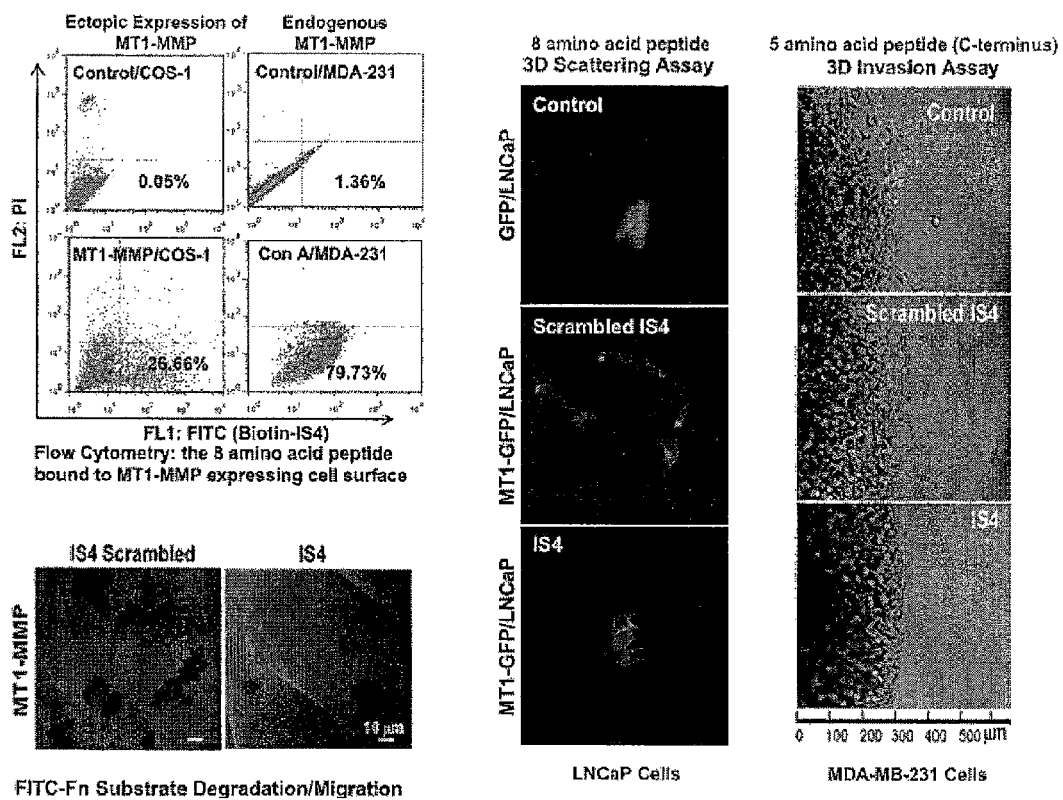
FIG. 9: Inhibition of MT1-MMP-induced cancer cell migration/invasion by IS4 peptide.
Figure 10:
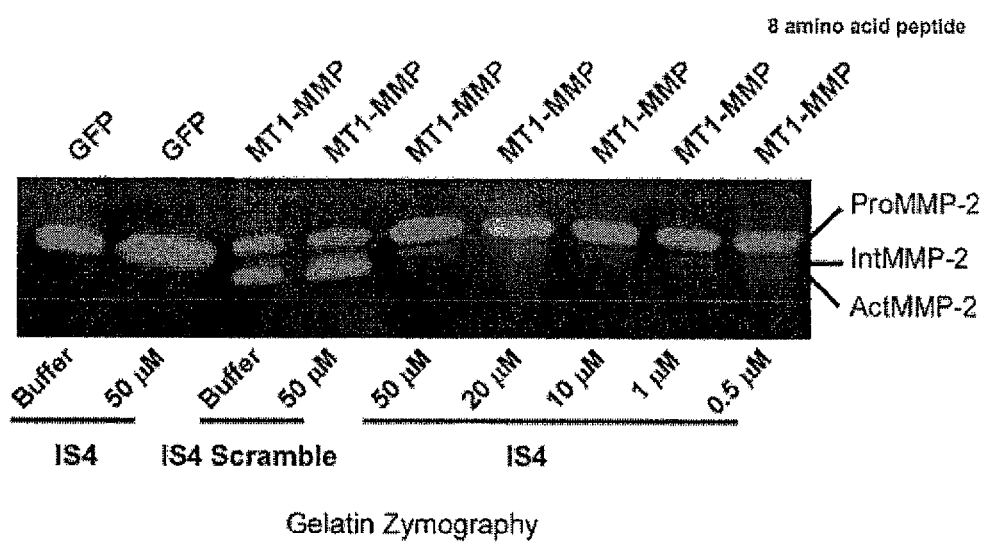
FIG. 10: Inhibition of ProMMP-2 activation by the IS4 peptides.

With respect to any of the invention's methods that employ the invention's compositions, in a particular embodiment, the MMP is MT1-MMP, and the amino acid sequence is selected from the a) GYPMP (SEQ ID NO:04) (1S4-5), b) VMDGYPMP (SEQ ID NO:01)) IS4-8), and c) GYPKSALR (SEQ ID NO:03) (IVS4-8), and the therapeutic amount of the composition specifically reduces cell migration that is mediated by MT1-MMP (FIG. 7).

Cell migration that is "mediated by" or "induced by" a molecule (such as MT1-MMP, MMP-9, MT3-MMP, MT1-MMP, MT6-MMP, etc.) means that the level of cell migration depends on the activity of the molecule, such that altering (i.e., increasing or decreasing) the activity of the molecule results in altering (i.e., increasing or decreasing) the level of cell migration.

The term "specifically reduces cell migration that is mediated by MT1-MMP" when in reference to a composition means that the composition reduces cell migration that is mediated by MT1-MMP, in the absence of a reduction of cell migration that is mediated by MMP-9 and/or MT3-MMP and/or MT6-MMP (FIG. 7). For example, data herein demonstrate that the invention's polypeptides specifically reduce MT1-MMP-induced cell migration, and did not reduce cell migration that is mediated by MMP-9, MT3-MMP, and/or MT6-MMP (FIG. 7).

With respect to any of the invention's methods that employ the invention's compositions, while not intending to limit the invention's sequences to any particular mechanism, in one embodiment, the invention's sequences are administered in an amount of that reduces homodimerization of an MMP that contains the invention's sequence.

Thus, in one embodiment, the invention's sequences that are derived from MT1-MMP (e.g., GYPMP (SEQ ID NO:04), VMDGYPMP (SEQ ID NO:01), and GYPKSALR (SEQ ID NO:03)) are administered in an amount to reduce homodimerization of MT1-MMP. In another embodiment, these sequences are administered in an amount that reduces heterodimerization of MT1-MMP and CD44.

E. Exemplary Uses of the Invention's Compositions in Detecting MMPs and Diagnostic Applications The invention provides a method for detecting a disease associated with expression of a matrix metalloproteinase (MMP) (e.g., cancer metastasis) in a subject comprising a) providing i) any one or more of the compositions disclosed herein, and ii) a sample from the subject, b) contacting the composition with the sample, and c) detecting binding of the polypeptide that is comprised in the composition to the sample, thereby detecting the disease in the subject. In some embodiments, the invention's polypeptide that is comprised in the composition is covalently linked to a detectable label, and the detecting comprises detecting the label.

"Probe," "label" and "reporter molecule" are interchangeably used to describe a chemical moiety that, when attached to a composition of interest, acts as a marker for the presence of the composition of interest, such that detection of the label corresponds to detection of the composition of interest.

The label may be detectable in any detection system, including, but not limited to enzyme (e.g., ELISA, as well as enzyme-based histochemical assays), fluorescent, radioactive, and luminescent systems. Examples of imaging reporters include, without limitation, Technetium-99m (Tc-99m), Indium-111 (In-111), Gallium-68 (Ga-68), Gallium-67 (Ga-67), Rhenium-186 (Re-186) (Visser et al. (1993) *J Nucl Med* 34: 1953-1963), Rhenium-188 (Re-188) (Guhlke et al. (1998) *Nucl Med Biol* 25: 621-631); Iodine-123 (I-123), Iodine-125 (I-125), Iodine-131 (I-131), Iodine (I), Gadolinium (Gd), Ytterbium (Yb) (Krause et al. (1996) *Invest Radiol* 31:502-511), Dysprosium (Dy) (Vera et al. (2002) *Acad Radiol* 9:784-792), Europium (Eu), Perflubron-based emulsions (Mattrey et al. (1990) *Invest Radiol* 25: 915-921), and Microbubble-based emulsions (Sirlin et al. (1999) *Ultrasound Med Biol* 25: 331-338).

The invention's methods are particularly useful in detecting any disease in which MMP is expressed (Table 3), and in particular, cancer (e.g., cancer metastasis).

The invention's methods are not limited to a particular approach to detecting binding of the invention's peptide sequences to their cognate MMP. In one embodiment, detecting binding to the invention's peptide sequences typically involves using peptide sequences that are labeled with a detectable moiety, such as radioisotope (e.g., $^3$H, $^{14}$C, $^{32}$P, $^{35}$S, and/or $^{125}$I), fluorescent or chemiluminescent compound (e.g., fluorescein isothiocyanate, rhodamine, and/or luciferin) and/or an enzyme (e.g., alkaline phosphatase, beta-galactosidase and/or horseradish peroxidase).

Methods for covalently linking peptide sequences to a detectable moiety are known in the art (e.g., Hunter, et al., Nature 144:945 (1962); David, e at., Biochemistry 13:1014 (1974); Pain, et al., J. Immunol. Meth. 40:219 (1981); and Nygren, J. Histochem. and Cytochem. 30:407 (1982).

Thus, the invention's peptide sequences may be employed in radiographic in vivo imaging, wherein an invention's peptide sequence labeled with a detectable moiety such as a radio-opaque agent or radioisotope is administered to a subject, preferably into the bloodstream, and the presence and location of the labeled peptide sequence in the host is assayed. This imaging technique is useful in the staging and treatment of malignancies.

The invention's peptide sequences are additionally useful as affinity purification agents. In this process, the peptide sequences are immobilized on a suitable support, such a Sephadex resin or filter paper, using methods well known in the art, to capture and purify MMPs (Table 1 & 2) that contain sequences that specifically bind to the invention's peptide sequences.

EXPERIMENTAL

The following examples serve to illustrate certain embodiments and aspects of the present invention and are not to be construed as limiting the scope thereof. The results of Examples 1-15 are illustrated in FIG. 28-42. Examples 16-26 refers to planned experiments, of which the results of those that have been completed are illustrated in FIG. 43-46.

Example 1

Establishment of Stable Human Prostate Cancer LNCaP and Human Breast Cancer MCF-7 Cell Lines Expressing "Physiologic" Levels of MT1-MMP-GFP Chimera (MT1-GFP)

Figure 28:
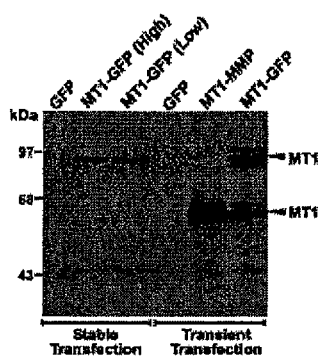
FIG. 28: Evaluation of stable LNCaP cells expressing MT-1GFP chimeric cDNA.

The goals of these experiments (previous DOD PCRP funding period) were to: 1) identify a minimally aggressive human prostate cancer and breast cancer cell lines that produced negligible amounts of MT1-MMP; 2) transfect these cells with MT1-MMP cDNA and isolate stable cell lines producing variable amounts of MT1-MMP, and 3) correlate MT1-MMP expression with cancer invasion/metastasis. To this end, MT1-MMP-GFP (MT1-GFP) chimera by fusing GFP cDNA to the C-terminus of MT1-MMP cDNA was constructed and this chimera has been demonstrated to have similar features with wild-type MT1-MMP (45-48). MCF-7 and LNCaP cells were chosen for these studies because of the absence of detectable MT1-MMP (49,50). Stable MCF-7 and LNCaP cell lines expressing MT1-GFP chimeric cDNA were generated (48). High and low MT1-MMP expression clones were selected. As assessed by Western blotting, protein levels of MT1-MMP in high expressing LNCaP cells were roughly equivalent to non-transfected DU-145 prostate cancer cells and HT1080 fibrosarcoma cells and ~10 fold less than transiently transfected LNCaP cells (FIG. 28). Expanded clones of high, medium, and low expression of MT1-GFP and GFP were examined by cell proliferation assay (MTT assay, Promega) in 2-dimentional (2D) tissue culture dishes. No difference of selected clones in cell proliferation was noted as compared to non-transfected cells.

Example 2

Enhanced Shedding of E-Cadherin by MT1-MMP Expressing Cancer Cells

We recently demonstrated that soluble E-cadherin (80 kDa) was detected in the conditioned medium of non- and GFP transfected LNCaP cells. Overexpression of MT1-GFP in stably transfected LNCaP cells as compared to GFP-only transfected cells, resulted in 5-fold increase of shed E-cadherin in the conditioned medium, indicating induction of cleavage of E-cadherin by MT1-MMP (FIGS. 29A &B). To examine if shedding of E-cadherin at cell-cell adherens junctions correlated with loss of cell surface E-cadherin, biotinylation of cell surface proteins followed by streptavdin precipitation and Western blotting using anti-E-cadherin antibody was performed (51). Decreased biotinylated surface E-cadherin (120 kDa) was observed in MT1-GFP expressing LNCaP cells (FIGS. 29A & B). Inhibition of enzymatic activity of MT1-MMP by tissue inhibitor of matrix metalloproteinase-2 (TIMP-2) (52), but not TIMP-1, interfered with cell surface E-cadherin shedding, confirming the specific role of MT1-MMP in E-cadherin cleavage.

Employing laser scanning confocal microscopy, co-localization of MT1-MMP with E-cadherin was examined based on GFP auto-fluorescence along with immunofluorescence staining using anti-E-cadherin antibody. MT1-MMP distribution was reorganized from uniform cell surface localization in isolated cells to distribution limited to the cell-cell junction area following partial confluence of MT1-GFP expressing cells. Endogenous E-cadherin, primarily enriched along the lateral membrane (53), was co-localized with MT1-MMP in LNCaP cells and displayed decreased intensity as compared to GFP expressing LNCaP cells (FIG. 29C, manuscript in preparation). These data confirm that MT-MMP induced loss of E-cadherin at the adherens junctions.

Example 3

Enhancement of LNCaP Cell Migration by MT1-MMP

We previously demonstrated that MT1-MMP enhanced cell migration in transfected non-tumorigenic COS-1 cells (8). To examine if MT1-MMP increased LNCaP cell migration, phagokinetic assay was employed (8). MT1-GFP expressing LNCaP cells contain more intracellular gold particles because of phagocytosis and displayed a long migratory path based on cleared gold particle tracks (FIG. 30-b1) as compared to LNCaP cells expressing GFP (FIG. 30-a1). Frames a2 and b2 in FIG. 4 demonstrate the auto-fluorescence of GFP and MT1-GFP expressing cells corresponded to the left panel. By image analysis with the same number of the cells, the cleared gold particles area was three-fold increase in cells expressing MT1-MMP (FIG. 30B).

Example 4

Figure 5:
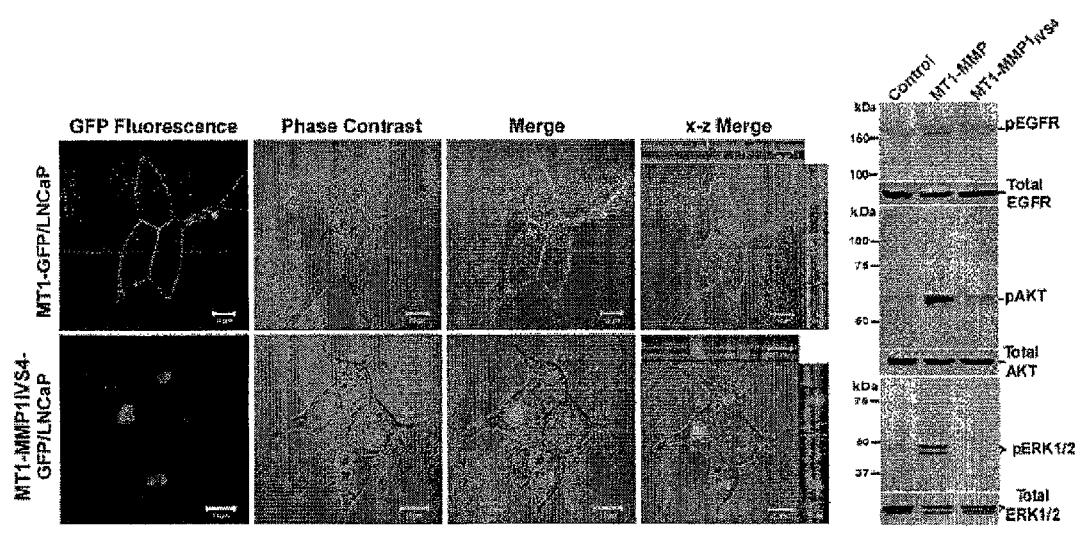
FIG. 5: Requirement of the IVS4 of MT1-MMP for cell surface localization.
Figure 6:
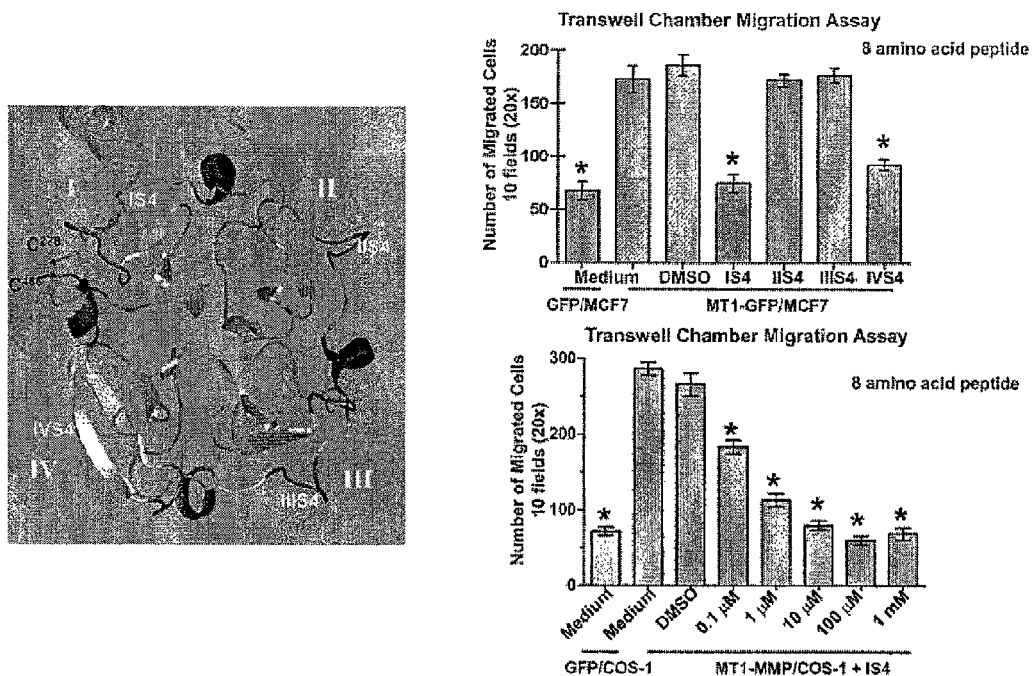
FIG. 6: Structure-based peptide design: Targeting the hemopexin domain of MT1-MMP.

Digestion of Fluorescein Isothiocyanate (FITC)-Labeled Matrigel by MT1-MMP Expressing LNCaP Cells To examine the role of MT1-MMP in invasion through basement membrane in an in vitro assay, we labeled Matrigel, a soluble basement membrane matrix from the EHS tumor with FITC. Western blotting using anti-type IV collagen and anti-laminin V antibodies confirmed that type IV collagen and laminin V remained intact in FITC-labeled Matrigel. Using FITC-labeled Matrigel-coated coverslips, LNCaP cells producing MT1-GFP were examined for Matrigel degradation. MT1-MMP expressing LNCaP cells readily degraded the FITC-labeled substrate (depicted by loss of fluorescence-labeled Matrigel in FIG. 31A-a). Interestingly, MT1-GFP producing LNCaP cells migrated over Matrigel in a random fashion leaving a track of digested substrate as a finger-print. The digestion of Matrigel was dramatically increased in the presence of recombinant proMMP-2 (FIGS. 31A-b & 5B) but was limited in area to the cell migration track. Addition of recombinant TIMP-1 resulted in partial inhibition of substrate digestion (down to the basal digestion level resulting from MT1-MMP alone) induced by MT1-GFP expressing cells in the presence of proMMP-2 (FIG. 31A-c), but did not interfere with cell migration. In contrast, addition of TIMP-2 with proMMP-2 (FIG. 31A-d) totally abolished the digestion of Matrigel. Using a similar strategy, FITC-labeled type IV collagen (Chemicon) was found to be degraded by MT1-GFP expressing LNCaP cells. Highly concentrated soluble MT1-MMP, however, was not able to cleave FITC-type IV collagen in a cell-free system suggesting that the MT1-MMP membrane anchor and/or coordination with adjacent molecule(s) is required for type IV collagen degradation.

Example 5

Distinct Domains of MT1-MMP Plays a Different Role in Substrate Degradation and Cell Migration (8)

Using FITC-labeled gelatin coated coverslips and engineered MT1-MMP substitution mutations, structure-function relationships of MT1-MMP in cell invasion and migration were studied by domain shuffling experiments (FIG. 32A). As expected, MT1-MMP expressing cells degraded FITC-labeled gelatin and migrated over digested substrate (FIG. 32B). Compared with MT1-MMP expressing cells, MT1-MMP2$_{PEX}$ expressing cells demonstrated full ability to degrade local gelatin, but failed to initiate cell migration (FIG. 32B). To examine the effect of proteolytic activity of MT1-MMP on cell migration, we employed a natural MMP inhibitor, TIMP-2 in combined FITC-labeled substrate degradation assay and phagokinetic assay (54) by coating coverslips with both FIT-labeled fibronectin and colloidal gold particles. As expected, TIMP-2 interfered with substrate degradation of MT1-GFP expressing cells (FIG. 32C). Surprisingly, the migration of these cells in the presence of TIMP-2 was not altered as demonstrated by the unimpaired cleared gold particle track (FIG. 32C). This observation was further confirmed by examining a constitutively inactive MT1-GFP chimera (MT$^{E240 \rightarrow A}$-GFP) in a cell migration assay (8). Our data indicate for the first time that the catalytic and hemopexin (PEX) domains of MT1-MMP play independent roles in ECM degradation and cell migration, respectively.

Example 6

The Cytoplasmic Domain of MT1-MMP is not Required for MT1-MMP Mediated Cell Migration The role of the cytoplasmic domain of MT1-MMP is controversial (55,56). Hotary et al. (55) demonstrated that the cytosolic tail of MT1-MMP is not required for MT1-MMP-enhanced cell invasion. We have demonstrated that the cytoplasmic domain of MT1-MMP is not required for proMMP-2 activation and cell migration (8). We demonstrated that deletion of the cytoplasmic domain of MT1-MMP (MTΔC) did not result in loss of protease activity in transfected human breast cancer cells (MDA-MB-231). MDA-MB-231 cells transfected with MTΔC and MT1-MMP cDNAs similarly digested FITC-labeled fibronectin and migrated over digested substrate (FIGS. 33A-a1 & c1). The migration of MTΔC expressing cells is not dependent on the substrate since the same result was observed with FITC-labeled Matrigel and type IV collagen. As expected, the transmembrane domain-deleted MT1-MMP (Sol.MT1) was not able to digest FITC-fibronectin (FIG. 33A-b1).

We recently found that expression of MT1-GPI$^{uPAR}$ chimera (FIG. 33B), by fusing a glycosyl-phosphatidyl-inositol (GPI) linker of urokinase plasminogen activator receptor (uPAR) to mutant MT1-MMP lacking the transmembrane and cytoplasmic domains of MT1-MMP, in LNCaP cells resulted in cell scattering in 3D type I collagen gels, similar to wild-type MT1-MMP, whereas inactive MT1$^{E240 \rightarrow A}$-GFP/LNCaP failed to scatter in 3D type I gels (FIG. 33C). This result reinforces the notion that the cytoplasmic tail of MT1-MMP is not required for cell migration and scattering. These data raise an important question of how MT1-MMP signals the cell to migrate.

Example 7

Interference with MT1-MMP-Induced Cell Migration, but not Substrate Degradation by Exogenous GST-MT$_{PEX}$ Fusion Protein We previously demonstrated that distinct domains of MT1-MMP play different roles in substrate degradation and cell migration (FIG. 32) (8). Our results and others emphasized the critical role of the PEX domain of MT1-MMP in cells migration (8,57). Since MT1-MMP forms homodimer and/or heterooligomers at the cell surface (5,6), interference with complex formation has been demonstrated to block downstream events. As proof of this hypothesis, we generated chimeric cDNAs encoding GST and GST-MT$_{PEX}$ chimera. The purified GST-tagged MT$_{PEX}$ protein (FIG. 34A) inhibited MT1-MMP-mediated cell migration as examined by FITC-fibronectin degradation assay and Transwell chamber migration assay (FIGS. 34B & C), but not substrate degradation (FIG. 34B) and proMMP-2 activation. These data support our hypothesis that interference with homodimer or heterooligomer will inhibit MT1-MMP-mediated cell migration.

Example 8

FAK is not Involved in MT1-MMP-Mediated Cell Migration

The sites of cell-ECM contact are established by the assembly of various proteins, including integrins, focal adhesion kinase p125$^{FAK}$, and vinculin, which together form complexes known as focal adhesions (58). To determine the potential connection between MT1-MMP and integrin signaling, we examined if FAK is involved in the MT1-MMP-mediated signaling pathway for cell migration. FAK−/− fibroblasts (ATCC) exhibit a rounded morphology as compared to a fibrillar pattern of FAK+/+ fibroblast control (FIG. 35A)(59). Western blotting using anti-FAK antibody (Biosource) confirmed the genotypic difference between FAK−/− and FAK+/+ fibroblasts (FIG. 35B). Employing a FITC-fibronectin substrate degradation assay, FAK−/− fibroblast transfected with MT1-GFP cDNA digested FITC-fibronectin and migrated over digested substrate similar to wild type FAK+/+ cells (FIGS. 35C-a1 & b1). Likewise, these cells displayed fibrillar cell morphology as compared to non-transfected FAK−/− cells (FIG. 35C-a2). Thus, FAK is not required for these MT1-MMP mediated-activities.

Since vinculin is present both at adherens junctions and focal adhesions (60,61) and is associated with the E-cadherin adhesion complex (62), we examined co-localization of both FAK and vinculin by co-immunofluorescent staining with anti-phosphorylated FAK and anti-vinculin antibodies in MT1-GFP transfected MCF-7 breast cancer cells (FIG. 35D). Phosphorylated FAK was detected at focal adhesions in all cells examined (FIG. 35D-a1-c1). Vinculin in MT1-GFP expressing MCF-7 cells (FIG. 35D-c2), but not in control cells, was diminished possible through relocation from focal adhesions since vinculin was found to be similar in the total cell lysates as examined by Western blotting using anti-vinculin antibody. Since cancer cells devoid of vinculin are highly metastatic and motile (63,64), MT1-MMP induced dissociation of E-cadherin adhesion complex components including β-catenin and vinculin, would be expected to enhance EMT.

Example 9

Involvement of Rho GTPase Rac 1, Mitogen-Activated Protein Kinase (MAPK) and Phosphoinositide 3-Kinase PI3K in MT1-MMP-Induced Cell Migration but not Substrate Degradation We previously demonstrated that MT1-MMP-mediated cell migration requires signaling through the Rac 1 pathway (8). By employing inhibitors targeting MAPK, PI3K, protein kinase A (PKA), and Rho-associated protein kinase (ROCK) signaling pathways and examining MT1-GFP-expressing LNCaP cell function in a FITC-labeled fibronectin substrate degradation/migration assay, we recently found that MT1-MMP mediated cell migration, but not substrate degradation, requires activation of MAPK and 10C not PKA or ROCK (FIGS. 36 A & B). These results were validated in a Transwell chamber migration assay. By Western blotting analysis, we confirmed that active extracellular-signal-related kinase 1/2 (ERK1/2) were dramatically enhanced in MT1-GFP/LNCaP cells (FIG. 36 C).

Example 10

Scattered Growth Pattern of MT1-GFP Expressing LNCaP Cells in Type I Collagen Gels Although increasing evidence highlight the importance of proteolytic remodeling of the ECM during invasion (65,66), recent reports have challenged this concept showing that the ability of tumor cells to migrate through collagenous barriers by switching to an amoeboid-like form was independent on proteinases (67). This observation, however, was possible due to reversible MMP inhibitors and low concentration of inhibitors (68). Employing fibroblasts isolated from gene-targeted mice, Sabeh et al. (68) demonstrated that MT1-MMP plays a dominant role in most tissue-invasive processes as MT1-MMP-suppressed tumor cells were unable to traverse through type I collagen gels, the chicken chorioallantoic membrane (CAM) interstitial matrix, or human dermis. Employing a 3-dimensional (3D) culture in native type I collagen gel, we examined the cell scattering effect of MT1-GFP. MT1-GFP transfected LNCaP cells displayed a change in morphology from epithelial to fibroblast-like cells with MT1-MMP polarized at the leading edge (FIG. 37A-b1). GFP-alone expressing LNCaP cells formed spherical aggregates (FIG. 37A-a2-a3), while MT-GFP expressing LNCaP cells presented a scattered distribution in the gels (FIG. 37-b2-b3). H & E staining of frozen sections confirmed this observation (FIG. 37A-a4,b4). The scattered distribution of MT1-GFP expressing LNCaP cells was abolished in the presence of TIMP-2 (10 nM), but not TIMP-1 (FIG. 37B). These data demonstrate that MT1-MMP induces EMT-like phenotypic changes and emphasize that the enzymatic activity of MT1-MMP plays critical role in cancer cell scattering in type I collagen gel.

Example 11

MT1-MMP Promotes Human Prostate Cells (LNCaP) and Breast Cancer (MCF-7) Cell Proliferation in a 3D Culture Model We recently also demonstrated that MCF-7 cells stably transfected with MT1-GFP chimeric cDNA presented a scattering growth pattern as compared to the spheroid growth pattern of GFP-transfected MCF-7 cells cultured in 3D type I collagen gels (FIG. 38A). We observed that cells expressing MT1-GFP in 3D gels proliferated more rapidly than control cells (FIG. 38A, 37A-b3). To quantitate cell proliferation, we employed a MTT cell proliferation assay in 3D culture (69) as compared to 2D culture (collagen coated plastic dishes). MT1-GFP significantly enhanced LNCaP and MCF-7 cells proliferation in 3D culture, but not in 2D cultures (FIG. 38B). Hotary et al (70) proposed that pericellular proteolytic activity in 3D culture, but not in 2 D culture, was responsible for the growth enhancing effects of MT1-MMP.

Example 12

T1-MMP Expressing MCF-7 Breast Cancer Cells Exhibit Enhanced Growth, Invasion and Metastasis in an Orthotopic Tumor Model, Even in the Absence of Estrogen Supplementation Cells from stable MCF-7 clones expressing high levels of MT1-GFP and GFP were injected subcutaneously into the mammary fat pad of 4-5 week old female athymic nude mice (nu/nu) in the absence of estradiol pellets; tumor growth was monitored as we previously described (71). MT1-GFP tumors were visible at week 3 and grew rapidly after week 9 (FIG. 39). Sounni et al. (72) previously reported that suspension of MCF-7 cells in a Matrigel slurry prior to injection into nude mice supplemented with estradiol pellets resulted in a long latency and limited growth rate, as compared to MT1-MMP expressing clones which produced large, well vascularized tumors. This limited growth rate even in estrogen-stimulated mice supports the concept that MT1-MMP expression induced a more aggressive tumor phenotype. Of considerable interest, MT1-MMP expressing clones display increased levels of VEGF mRNA and protein through an unidentified transcriptional mechanism (72,73).

Example 13

MT1-MMP Dramatically Enhanced Prostate Cancer Invasion/Metastasis in an Orthotopic Prostate Cancer Model (48)

Employing an orthotopic prostate cancer model (tumor cells injected directly into the prostate of nude mice), we demonstrated that MT1-GFP/LNCaP tumors displayed more invasive local growth in tumor-bearing mice. Metastases to inguinal nodes were noted in MT1-GFP/LNCaP tumor bearing mice with enlarged inguinal nodes, but not in GFP/LNCaP-bearing mice. GFP/LNCaP primary prostate tumors were well-organized (FIG. 40C); MT1-GFP/LNCaP tumors were anaplastic and more invasive with areas of hemorrhage (FIG. 40D). Isolated single metastatic cells were infrequently found in the lungs of GFP/LNCaP-bearing mice based on GFP fluorescence (FIG. 40A). In contrast, dramatic enhancement of tumor metastases was noted in the lungs and lymph nodes of MT1-GFP/LNCaP tumor-bearing mice (FIGS. 40B & F). This result emphasizes the pivotal role of MT1-MMP in this prostate cancer model and confirms that MT1-MMP is a suitable therapeutic target to interfere with prostate cancer metastasis.

Example 14

MT1-MMP Forms a Complex with CD44H in Cells

It has been proposed that MT1-MMP cross-talks with an adjacent molecule which signals for cell migration (29). Several reports have demonstrated that MT1-MMP forms a heterodimer with cell surface CD44H through the PEX domain of MT1-MMP resulting in shedding of CD44H and leading to cell migration (6,7,74). To set up a testing model system to pinpoint critical motifs within the PEX domain of MT1-MMP required for interacting with CD44, co-immunoprecipitation between MT1-MMP and CD44H in cell lysates was performed. In experiment 1, COS-1 cells co-transfected with CD44H cDNA (generously provided by Dr. Bryan Toole, Medical Univ. of S. Carolina) plus GFP control or MT1-MMP cDNA were lysed and immunoprecipitated with anti-MT1-MMP catalytic domain antibody followed by Western blotting with anti-CD44 antibody. CD44H was noted to co-precipitated with MT1-MMP (FIG. 41A). Specificity of coimmunoprecipiation was confirmed by in experiment 2 employing cells co-transfected with MT1-MMP cDNA plus CD44H or GFP cDNA followed by CD44 antibody for precipitation and MT1-MMP antibody in Western blot (FIG. 41B).

Example 15

Strand Four of Blades I and IV is Required for MT1-MMP-Mediated Cell Migration

The PEX domain of MMPs is organized into four □-sheets (blades) (75). Each blade consists of four anti-parallel □-strands connected in a W-like strand topology. Since the outermost strands of the MMP PEX domain is believed to mediate contacts with other protein components (76), the outermost strands of each blade (IS4 to IVS4, see FIG. 43) were replaced with corresponding regions of MMP-1 (minimal homology with MT1-MMP). Substituted mutations of the strand four of blades I and IV failed to result in proMMP-2 activation and cell migration (FIGS. 42B & C). Interestingly, the proteolytic activity of MT1-MMP mutations in terms of substrate degradation was intact (FIG. 42C).

Example 16

Determine the Critical Motifs within the Outer Strands of Blades I and Iv of the PEX Domain of MT1-MMP Responsible for Cell Migration We proposed to individually swap the β-strand and loops flanking the β-strand of the strand 4 of blades 1 and 4 with that of MMP-1 (based on lack of similarity). Specifically, the β-strands (IS4β-$Y^{352}$-$P^{355}$, and IVS4β-$P^{495}$-$A^{501}$) and loops of IS4 and IVS4 will be individually replaced by the corresponding regions in the MMP-1 (FIG. 44) using the Site-Directed Mutagenesis Kit (Stratagene) as described previously (8). These mutations are based on in silico analysis of hemopexin-like structures. As control experiments, β-strands and flanking loops of the strand 4 of blades II and III of MT1-MMP (blade II and III not required for MT1-MMP-mediated cell migration) (FIG. 42), will be also replaced by corresponding regions of MMP-1. The resultant PCR products containing MT1-MMP1 chimeric cDNAs, named MT1-MMP1 (IS4β, IS4L1 IS4L2, (L refers to loop flanking the β-strand), and so on) will be cloned upstream of the internal ribosomal entry site (IRES) in the pIRES2-EGFP vector (Clontech) to facilitate green fluorescence for determination of transfected cells. The constructs will be confirmed by DNA sequencing for junction areas and by Western blotting of transfected cells using an anti-MT1-MMP catalytic domain antibody (Oncogene). This mutagenesis strategy should not abrogate the symmetric β-propeller shape of the MT1-MMP PEX domain, but will change the surface residue presentation, presumably leading to interference with homodimer formation and/or heterooligomer formation. We will provide 3D structural information of the PEX domain of MT1-MMP to further refine our mutagenesis data once this information is available. Based on our preliminary data (FIG. 42), the minimum motif within the strands IS4 and IVS4 required for MT1-MMP migratory function will be identified.

Example 17

Evaluate Substitution Mutations of MT1-MMP1 Chimera in Cell Migration/Invasion

To examine the role of β-strand and flanking loops in each blade of MT1-MMP PEX domain in cell migration, LNCaP cells transfected with each of the MT1-MMP1 chimeric cDNAs (FIG. 44) will be plated onto FITC-labeled gelatin-coated coverslips. Wild-type MT1-MMP transfected cells will serve as a positive control. Enzymatic activity of MT1-MMP1 chimeras will be determined based on the local degradation of the FITC-labeled gelatin and cell migration will be observed based on the path of loss of FITC-labeled substrate. MT1-MMP1 chimera(s) with a mutated critical region in the PEX domain will be defective in cell migration, but not in FITC-gelatin degradation (FIG. 42). This data will be validated by the Transwell chamber migration assay. Based on these migration assays, a minimum motif(s) in the IS4 and IVS4 will be identified.

If none of the mutations affects cell migration, it suggests that the junctions between β-strand and flanking loops are required for MT1-MMP-mediated cell migration since mutation of the entire fourth strand of blades I and IV resulted in cells lacking migration ability (FIG. 42). If this is the case, scanning mutations of 4-5 residues that span both β-strand and flanking loops of the fourth strand of blades I and IV (FIG. 44) will be generated similarly to the substituted mutations described in D2.1. They will be tested by cell migration assay. If the mutation results are again negative, we will increase the number of residues mutated. We are initially focusing on short spans for developing inhibitors based on the critical motif.

Example 18

Identify Region(s) within the PEX Domain of MT1-MMP Required for Homodimer Formation Itoh et al. (5) reported that homodimer formation of MT1-MMP through the PEX domain facilitates proMMP-2 activation on the cell surface and promotes tumor cell invasion. The detailed mechanism, however, has not been characterized. Our observation (FIG. 42) shows that substituted mutations of MT1-PEX IS4 and IVS4 inhibited both cell migration (heterooligomer requirement) and proMMP-2 activation (homodimer requirement), but did not affect proteolytic activity (FITC-labeled gelatin). We will test whether these mutations disrupt homodimerization of the MT1-MMP PEX domain, thus supporting our hypothesis that homodimerization is required for pro-MMP2 activation. In addition, we will test those mutants identified as described herein that disrupt cell migration, pro-MMP2 activation, or both. To identify a potential motif(s) required for homodimer formation, a FLAG-tag will be inserted into mutant MT1-MMP1 chimeric cDNAs (MT1-MMP1-IS4, -IIS4, -IIIS4 and -IVS4) described in FIG. 42 between the propeptide domain and catalytic domain by employing a two-step PCR as described before (8). COS-1 cells will be co-transfected with FLAG-tagged wild-type and mutant MT1-MMP1 cDNAs (four different forms, MT1-MMP1-IS4, -IIS4, -IIIS4 and -IVS4) and Myc-tagged wild-type MT1-MMP cDNA (Myc inserted between propeptide and catalytic domains) (5) and immunoprecipitated with anti-FLAG antibody-conjugated beads followed by Western blotting with anti-Myc antibody. Based on this co-immunoprecipitation result, the critical motif(s) required for homodimer formation will be defined.

We will analyze the oligomerization state of native and mutant MT1-MMP PEX domains using analytical ultracentrifugation (AUC). Because current constructs of the PEX domain of MT1-MMP (FIG. 34) contain a large fusion partner that will interfere with the analysis, we will produce a His-tagged recombinant PEX domain in *E. coli* that can easily be purified by immobilized-metal affinity chromatography (IMAC). Western blotting using anti-PEX domain antibody (Chemicon) and anti-His tag antibody will be used to validate the constructs.

A key feature of sedimentation experiments by AUC for determining protein interactions is that the faster sedimenting complexes migrate through a solution of the slower sedimenting components, permitting the hydrodynamic and thermodynamic characterization of even weak and transient interaction. The quantity of material required is typically on the order of a few hundred micrograms. Two basic types of experiments will be run: (1) a sedimentation velocity (SV) experiment in which a high centrifugal force is used to analyze the time-course of the sedimentation process; and (2) a sedimentation equilibrium experiment (SE) in which a low centrifugal force permits diffusion to balance the sedimentation such that a time-invariant equilibrium gradient can be observed (125). We will initially use SV experiments to determine the self-association properties of native and mutant MT1-MMP PEX domains. We will prepare at least three samples (400 µL each) ranging from 0.1 to 1 mg/ml for each mutant and wild-type. The association state and number of species present, e.g. monomer, dimer, or higher order oligomers will be determined. Furthermore, the experiment will allow us to generate a qualitative binding kinetic scheme that will be used to design SE experiments. The SE experiments will be used to determining binding association constants. They will be run at a similar range of concentrations. Both SV and SE experiments will be analyzed using software packages SEDFIT and SEDPHAT.

Based on the results of these experiments we will elucidate which structural mutations disrupt homodimerization. In conjugation with the results of cell migration assays, and pro-MMP2 activation assays, we will ascertain whether the protein interface of MT1-MMP PEX domain responsible for cell migration is distinct or overlapping with the interface responsible for pro-MMP2 activation. Moreover, our dimerization studies will elucidate whether homodimerization is required for pro-MMP2 activation, cell migration or both. Next, we will evaluate which protein interface is required for heteroligomer formation.

Example 19

Evaluate Critical Motif(s) in MT1-MMP Required for Heterooligomer Formation

Figure 41:
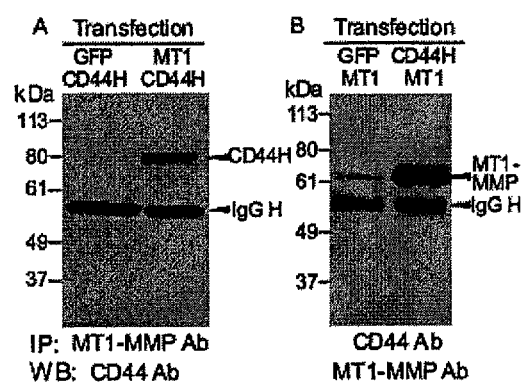
FIG. 41: MT1-MMP forms a complex with CD44H.

A. Employing co-immunoprecipitation experiments, we recently demonstrated that MT1-MMP interacted with CD44H in the transfected cells (FIG. 41). To examine the critical motif(s) within the PEX domain of MT1-MMP required for heterooligomer formation, the CD44H cDNA and MT1-MMP1 chimeric cDNAs generated as described herein will be co-transfected into COS-1 cells, and cell lysates will be precipitated with anti-CD44 antibody followed by Western blotting using anti-MT1-MMP (catalytic domain) antibody as shown in FIG. 41. Data generated from this co-immunoprecipitation test will be validated by switching of antibodies for precipitation and subsequent Western blotting. PEX mutants will be generated by swapping critical regions will no longer co-precipitate with CD44H. These experiments will identify the regions critical for interaction. However, the immunoprecipitation experiments do not eliminate the possibility that another binding partner may be required for complex formation. Thus, we will directly characterize the interaction between CD44H and the PEX domain.

B. Requirement of minimum motif(s) for CD44H-MT1-MMP complex formation will be validated by an analytical ultracentrifugation (AUC) technique (125). Similarly, we will start with SV experiments on CD44 alone to characterize its self-association properties. In combination with the self-association properties of MT1-MMP obtained from above mentioned experiments, this will provide reference for the heteroassociation study of CD44-MT1-MMP complex by SV experiments. The CD44 to MT1-MMP molar ratio will be varied according to their loading concentrations. The SV run will help to assess the purity of the samples and allow the estimation of the binding constant and the size of the complexes formed. This will help in planning the sample concentrations and the rotor speeds for the subsequent SE experiments. Interactions of soluble CD44 (~70 KDa) (74) and MT1-MMPpex (~25 KDa) can be detected through the emergence of new peaks (~120 KDa for CD44-MT1-MMP-MT1-MMP, ~95 KDa for CD44-MT1-MMP) at higher concentrations, shifts in the ratios of the peak areas, and/or shifts in the peak positions, depending on their binding affinity.

Although recombinant soluble CD44H from *E. Coli* is capable of binding to hyaluronan (126), the binding of other proteins including HGF, bFGF, and fibronectin is dependent on various post-translational modifications of CD44 at alternative exons that are not present in recombinant fusion proteins isolated from *E. coli* (127-129). Given this consideration, we propose to generate soluble CD44H in mammalian cell lines. The AUC experiments will require 500 µg to 2 mg of protein depending on the association constant (125). Based on our experience with soluble MT1-MMP expressed in COS-1 cells (FIG. 45), 2.25 mg/litter protein was obtained from the conditioned medium. The similar concentration of soluble CD44H will be obtained from the conditioned medium of transfected COS-1 cells. An advantage of the AUC method is that the protein can be recovered from the cell at the end of the run. A cDNA encoding the extracellular domain of CD44H from amino acid methionine 1 ($Met^1$) to glutamic acid 268 ($Glu^{268}$) will be amplified by a PCR approach and cloned into pcDNA3.1/Myc/His vector to facilitate affinity purification using a histidine (His) binding resin (Novagen). The construct will be evaluated by DNA sequencing and Western blotting using an anti-CD44 extracellular domain antibody (BD Biosciences Pharmingen). The soluble CD44H will be then purified from conditioned media of COS-1 cells transfected with the cDNA using the His binding resin as we employed previously for purification of soluble MT1-MMP (FIG. 45). The function of purified soluble CD44H will be examined by a modified ELISA assay employing immobilized hyaluronan (Sigma) as previously reported (126). Binding between MT1-MMP and soluble CD44H will be confirmed by a pull-down assay in which immobilized CD44 on the His resin beads will be incubated with MT1-MMP-expressing cell lysate in a low stringency buffer followed by Western blotting assay using anti-MT1-MMP antibody. Soluble CD44 will associate with MT1-MMP. If low secretion of soluble CD44H occurs, we propose to substitute the leading signal peptide of CD44H with V-J2-C region of the mouse Ig κ chain for efficient secretion of recombinant proteins (130) (pSecTag2/His, Invitrogen). Similar purification approach will be employed for soluble CD44H.

C. Validate the Critical Motif(s) Required for Heterooligomer Formation Using AUC The recombinant PEX domain substituted mutation proteins will be incubated with purified CD44H protein and analyzed by AUC as described in D2.3.2. This experiment will validate the data as described herein.

Example 20

Develop Sequence-Based Peptide Inhibitors Directed Against the Hemopexin-Like (PEX) Domain of MT1-MMP as Anti-Cancer Agents Degradation of collagen by MMPs has long been considered to be an essential component in progression from in situ carcinoma to invasive/metastatic cancer. Hence, the initial anti-MMP drugs for use in cancer were designed as peptide mimics of the collagen amino-acid sequence surrounding the collagenase cleavage site (131). Based on the supposition that MMPs were important in late stage cancer and the greater availability of advanced stage patients for recruitment to clinical trials, early stage cancer patients have been omitted from clinical trials of MMPIs.

More recently, the spectrum of MMP function has widened to include important aspects of early cancer development (132). Selective MMPs cleave growth factors, cell surface receptors, chemokines, angiogenesis and apoptosis factors, and expose neoepitopes in the extracellular matrix that alter various aspects of cell development. Bergers et al. (133) demonstrated that whereas MMPIs were quite effective in early treatment of experimental cancer, MMPIs were ineffective in advanced stage cancer. These results highlight the need for better understanding of the mechanisms by which multifunctional MMPs contribute to tumor growth, cell migration and ECM degradation. It is also essential to develop more selective MMP inhibitors that are devoid of side effects commonly seen with broad-spectrum inhibitors.

Figure 34:
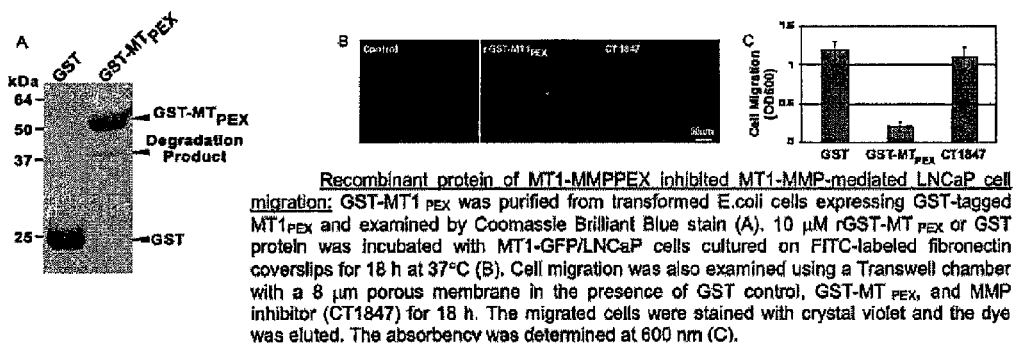
FIG. 34: Recombinant protein of MT1-MMPPEX inhibited MT1-MMP-medicated LNCaP cell migration.

Non-catalytic targeting of MMPs is an innovative strategy to block their various functions. Targeting the PEX domains of MMP-2 or -9 has efficiently inhibited cell migration induced by these MMPs (41,134). We recently demonstrated that recombinant MT1-PEX protein blocked MT1-MMP-mediated cell migration (FIG. 34). These studies shed light on alternative MMP inhibition strategies that could be useful in preventing cancer progression. Based on the identification of the critical PEX motifs required for cells migration, we propose to develop inhibitory peptides to competitively interfere with MT1-MMP-enhanced cell migration/invasion. These inhibitors will be also used to validate the role of MT1-MMP in EMT and to provide a lead compound to interference with early stages of cancer dissemination.

Figure 46:
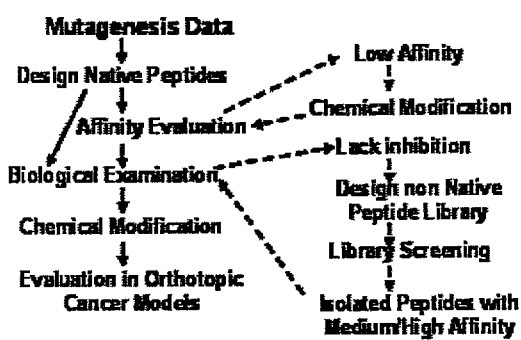
FIG. 46: Strategy for development of non-catalytic peptide inhibitors for MT1-MMP.

Co-expression of MT1-MMP and CD44H promotes cell migration accompanied with increased CD44H shedding (74, 135). Mori et al. (6) further demonstrated that the PEX domain of MT1-MMP bound to the CD44 stem region is a prerequisite for MT1-MMP-mediated cancer cell migration. The three-dimensional structure of CD44 is not known. Using a co-immunoprecipitation assay, we have confirmed the interaction between CD44H and MT1-MMP in transfected COS-1 cells (FIG. 41). As discussed herein, we propose to characterize the binding interaction between CD44H and MT1-MMP using analytical ultracentrifugation to test our hypothesis that these proteins directly interact. We further hypothesize that peptides derived from the MT1-MMP PEX domain will interact with CD44H and inhibit cell migration, if there is a direct CD44H-MT1-MMP interaction. If we are unable to demonstrate a direct interaction between CD44H and MT1-MMP, then peptides derived from the MT1-MMP PEX domain that inhibit cell migration will be useful for developing tools to identify additional PEX binding partners, e.g., pull down experiments. FIG. 46 illustrates a working chart for designing and charactering inhibitory peptides targeting the PEX domain of MT1-MMP.

Example 21

Design Sequence-Based, Native Competitive Inhibitory Peptides to Mimic the Critical Region of the PEX Domain of MT1-MMP Required for Cell Migration Based on data generated as described herein, targeting peptides will be synthesized to competitively inhibit the MT1-MMP PEX domain binding partner, that promotes migration, presumably CD44. Initially, we will synthesize peptides that correspond to the smallest (shortest sequence) regions mutated (FIG. 44) that abrogate cell migration. As control peptides, we will synthesize peptides with scrambled sequences. Depending on the outcome of the experiments proposed below, we will modify the peptides in order to improve binding and/or stability. Peptides will be synthesized by the ICB&DD Synthesis core. We will test peptides in three different ways to determine if they 1) bind to CD44H; 2) inhibit cell migration; and 3) inhibit pro-MMP2 activation. The combination of these assays will enable us to determine the mechanism of action of the peptides and to refine their structures if necessary.

Example 22

Determine the Binding Affinity of Synthesized Peptides for Purified CD44H

The binding affinity of synthesized peptide(s) will be evaluated using steady-state intrinsic tryptophan fluorescence spectroscopy. The tryptophan fluorescence of soluble mature CD44H protein will be monitored as peptide is titrated into the sample. If the peptide(s) bind, we expect to observe a change in the tryptophan signal, either a blue or red-shift or a change in quantum yield. What change we observe will depend on the orientation of the peptide with respect to the CD44H protein. If the sensitivity of the changes is too low, we will fluorescently label the recombinant CD44H with a higher quantum efficiency label like acrylodan or bimane in order to detect binding of the peptides. The titration data will be fit to a binding isotherm and the dissociation constant $K_d$ of the peptide(s)-CD44H interaction calculated. We will pursue these studies whether heteroligomerization of CD44H and PEX were observed or not. In the case that no heteroligomerization was observed, the peptide studies will serve as an additional test of the system.

Example 23

Examine if Peptides Competitively Interfere with Complex Formation Between Soluble CD44H and Soluble MT1-MMP In Vitro If the peptides bind to CD44H, we will examine if the selected peptide(s) competitively interferes with CD44H and MT1-MMP complex formation. The selected peptide(s) will be incubated with soluble CD44H-bound His resin at a saturating concentration (as determined in the binding isotherm experiments above) followed by incubating with soluble MT1-MMP. Scrambled peptide will be used as a control. After extensive washing with PBS, soluble MT1-MMP-bound to CD44 will be eluted from the resin and Western blotting using anti-MT1-MMP antibody will be then performed. This experiment will confirm if selected peptide(s) interferes with MT1-MMP heterooligomer formation with CD44.

Example 24

A. Evaluate the Biological Effect of Selected Peptide(s) on MT1-MMP-Mediated Cancer Cell Migration The peptide(s) will be tested for their effect on MT1-MMP-mediated cell migration, scattering in 3D culture, and validation of MT1-MMP PEX domain-related signaling pathways as we previously demonstrated (FIGS. 32, 36, & 37). If no effect is seen with a single dose in the following examinations, cells will be dosed several times to overcome any stability problems.

B. Evaluate the Effect of Synthetic Peptides on MT1-MMP-Mediated Cell Migration in 2D Cultures To select the inhibitory peptides that interfere with MT1-MMP-mediated cell migration, we will employ a FITC-labeled fibronectin substrate degradation/migration assay (FIG. 34). Peptide concentrations 10-100 times the CD44H $K_d$'s will be used to pre-incubate the peptides with LCNaP cells expressing MT1-GFP for 1 h at room temperature followed by transferring the cells to FITC-fibronectin-coated coverslips for 18 h at 37° C. in the presence of selected peptides. Interference with cell migration by inhibitory peptides will be examined by fluorescensce microscopy. Cell migratory ability will be determined by analyzing cell migration tracks using NIH imaging software (48). Ten fields of each group will be analyzed. Inhibitory effect of peptides on cell migration will be validated by the Transwell migration assay.

C. Determine the Effect of Selected Peptide(s) on MT1-MMP-Induced Cell Scattering in 3D Culture To determine the effect of selected inhibitory peptides on MT1-MMP-induced cell scattering in 3D collagen gels, MT1-GFP expressing LNCaP cells will be mixed with type I collagen and selected peptides (dose to be determined based on $K_d$ determined as described herein). Inhibitory effect of peptides will be determined by microscopic examination. Recombinant TIMP-2 will be employed as a control (FIG. 37).

D. Determine the Effect of Peptides on MT1-MMP-Mediated Pro-MMP2 Activation

It has been reported that homodimer formation of MT1-MMP is required for MT1-MMP-mediated proMMP-2 activation (5). We demonstrated that mutations at the strand four of blades I and IV resulted in the defect of cell migration and proMMP-2 activation (FIG. 44). It is possible that interfaces for homodimer and heterooligomer formation are overlapped or partially overlapped. To test this hypothesis, gelatin zymography in terms of proMMP-2 activation will be employed. LNCaP cells co-transfected with MT1-MMP and CD44H cDNAs will be incubated with and without tittered selected peptides based on $K_d$ in the serum-free medium at 37° C. for 8 hour. The conditioned medium will be then collected and examined by gelatin zymography. Densitometric analysis of activated MMP-2 will be performed. Interference with proMMP-2 activation by selected peptides will be determined. Selected peptides will interfere with proMMP-2 activation based on our previous observations (FIG. 42).

Example 25

Iterative Design of Peptides

There are several possible outcomes of these experiments. The most likely possibilities will each be examined in turn.

Binding of peptide to CD44H is of high affinity, i.e., at least low micromolar, the peptide inhibits MT1-MMP binding, and the peptide inhibits cell migration and/or pro-MMP2 activation. In this case, our hypotheses about the role of CD44H and the hemopexin domain of MT1-MMP are correct.

Binding of peptide to CD44H is of high affinity, i.e., at least low micromolar, the peptide inhibits MT1-MMP binding, yet no inhibition of cell migration or pro-MMP2 activation is observed. In this case, the most likely reason for no in vitro inhibition is the stability of the peptide under cellular conditions.

Binding of peptide to CD44H is of low affinity, i.e., high micromolar, the peptide inhibits MT1-MMP binding, yet no inhibition of cell migration or pro-MMP2 activation is observed. In this case, the most likely reason for lack of inhibition in vitro is low affinity of the peptide.

No binding of peptide to CD44H is observed, yet the peptide inhibits cell migration and/or pro-MMP-2 activation. In this case, the data suggest that the peptide binding partner and by inference the MT1-MMP binding partner is a protein other than CD44. These results will suggest that the inhibitory peptide sequence can be used as "bait", e.g., as a fusion protein, in a pull down experiment to identify the unknown binding partner.

No binding of peptide to CD44H is observed, and the peptide does not inhibit cell migration and/or pro-MMP-2 activation. In this case, the interpretation depends on the results of the heteroligomerization studies performed as discussed herein. If CD44H does bind to the PEX domain of MT1-MMP, then the most likely reason for this result is that the binding affinity for CD44H is too low. If CD44H does not bind to the PEX domain of MT1-MMP, then the result is most likely due to low stability of peptide in vitro, or low affinity of the protein for the unknown binding partner.

The cases of low affinity or stability require the design of new peptides. We will take two approaches depending on the CD44H results.

If CD44H does appear to be a direct binding partner for MT1-MMP, then we will use soluble CD44H to screen a limited library of peptides (50-100 sequences) based on the original target sequence. To increase in vitro stability, the peptide sequences will be modified with D-amino acids, secondary amino acids (for example, N-methyl amino acids) and non-natural amino acids that are close isosteres to the original residue. To increase affinity, we will employ modified amino acids that are close isosteres to the original residue, but more hydrophobic. In addition, we will modify the termini with hydrophobic groups, e.g., an N,N-dibenzyl amino acid. Increasing hydrophobicity often improves the van der Waals interactions between peptide and protein interface and improves binding affinity (136). These libraries will be synthesized by Dr. Seung-yub Lee, the Director of the Synthesis Core of the ICB&DD.

If CD44H does not appear to be a direct binding partner, then a more limited number of peptides can be tested because the available cell migration assays are not high-throughput assays. In this situation, we will make larger cyclic peptides that mimic the critical blades I and IV of the MT1-MMP PEX domain, individually. The length of the linker that connects the N-terminus to the C-terminus of the two strands will be varied to find the optimal length for biological activity. Cyclization will stabilize the peptides for in vitro studies and provide a larger contact surface to aid inhibition (137).

Example 26

Evaluate the Effectiveness of Inhibitory Peptides in Prevention of Prostate Cancer Invasion and Metastasis in an Animal Model Inhibitory peptides will be subsequently examined in the orthotopic prostate cancer implantation mouse model that we have employed previously (48). We propose to use LNCaP cells stably expressing MT1-GFP chimera cDNA. Based on the variability of tumor growth in animals and our previous experiments with prostate cancer metastasis, ~10 immunodeficient male SCID mice will be required for each experimental variable. Following orthotopic surgical implantation of the prostate with transfected LNCaP cells (48), the peptides will be administered to mice by i.v. injection, initially at a dose of ~10 mg/kg peptide twice a week (138); subsequent doses will be determined based on pilot studies. The half-life, toxicity, and stability of inhibitory peptides in mice will be determined as previously described (138,139). Pathological examination will be performed to characterize the invasive process (71) in collaboration with Dr. Hu. Inhibitory peptides will reduce prostate cancer invasion/metastases and prolong survival as compared to scrambled peptide-treated mice.

Example 27

Examination of Tumor Growth and Metastasis by MT1-MMP Expressing Cells in the Presence of Inhibitory Peptide $2 \times 10^6$ GFP expressing MDA-MB-435 cells were injected in the mammary fat pad of immunodeficient female mice followed by administering 20 mg/kg/day of specific and scrambled peptides via i.p. and intratumoral injection, alternatively. Primary tumor size was monitored over a 10-week time course. Inhibitory peptides had no effect on tumor growth (A). After twelve weeks, the mice were sacrificed and the organs were pathologically examined. The lungs were sliced into 3 mm thick sections. The incidence of lung metastasis was assessed by examining metastatic tumors in the lungs (B). The number (C) and size (D) of metastasized tumors in the lungs were microscopically counted based on GFP expression and measured using Nikon NIS Elements Imaging software, respectively.

Figure 48:
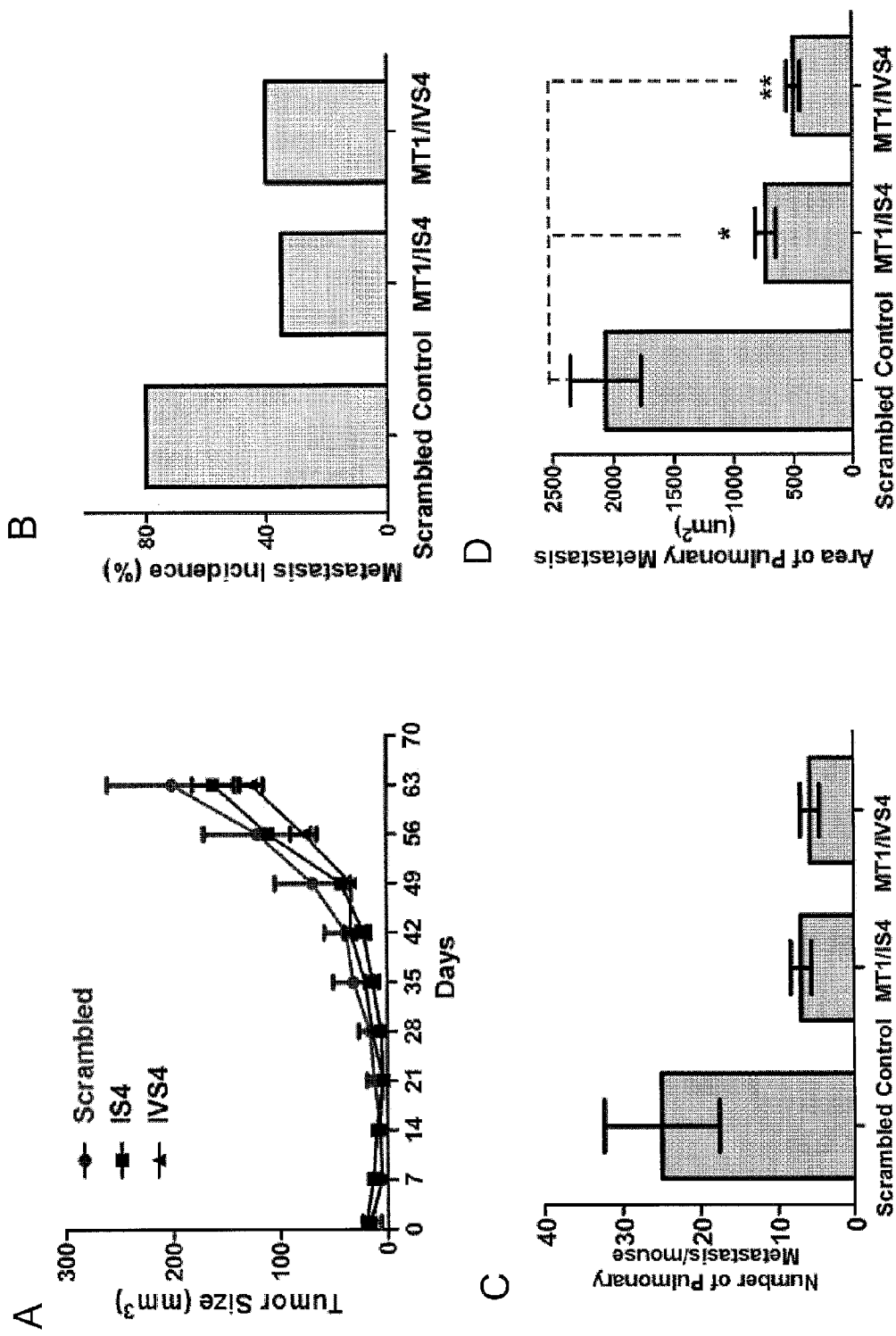
FIG. 48: Inhibition of lung metastasis without affecting primary tumor growth by the specific inhibitory peptides.

The results are shown in FIG. 48. Scrambled control peptide treated mice exhibited multiple large nodules, whereas the degree of lung metastasis was reduced in IS4 and IVS4 treated mice (C). Tumor foci area in the lung was subsequently quantified, and the tumor sizes in scramble peptide treated mice were noticeably larger than in mice treated with IS4 and IVS4 peptide (D).

Example 28

Figure 4:
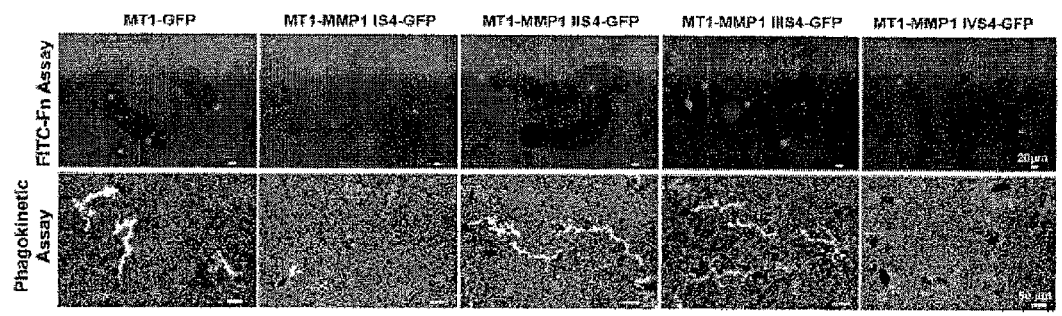
FIG. 4: Requirement of the fourth strand of blade I and IV of the PEX domain of MT1-MMP in cell migration.
Figure 49:
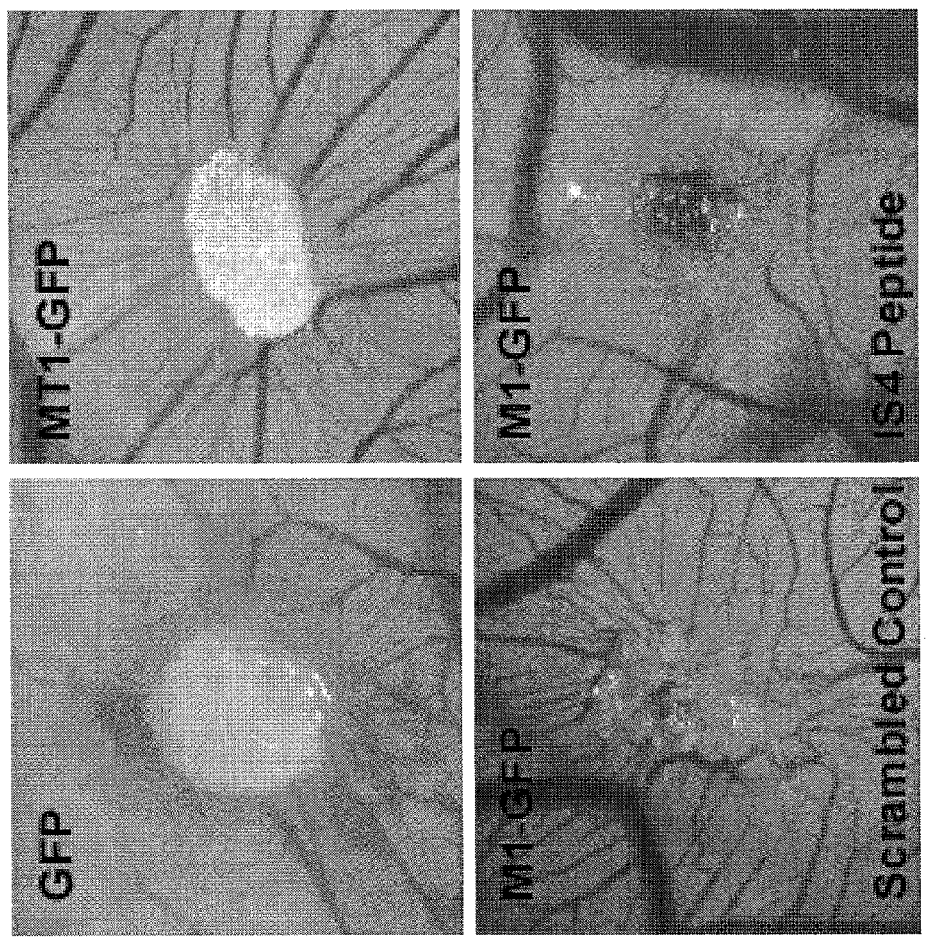
FIG. 49: Inhibition of MT1-MMP-mediated Angiogenesis by the IS4 Peptides.

Enhanced Blood Vessel Formation (Angiogenesis) by MCF-7 Cells Expressing MT1-MMP Using a Cam Assay Since angiogenesis and the development of metastases are intrinsically connected, we examined if inhibition of cancer metastasis by the MT1-MMP specific peptides is due to interference with MT1-MMP-induced angiogenesis. To this end, a chicken embryo chorioallantoic membrane (CAM) angiogenesis assay was employed. The tumor cells were treated with inhibitory peptides as well as scrambled controls and loaded onto the CAM. The results are shown in FIG. 49. After five days, we observed that treatment of MT1-MMP/MCF-7 cells with inhibitory peptides reduced MT1-MMP-mediated angiogenesis as made evident by a lack of developed vessels (thin and narrow vessels) and a decreased number of new blood vessels (FIG. 4).

REFERENCES

1. Boyer, B., Valles, A. M., and Edme, N. (2000). Induction and regulation of epithelial-mesenchymal transitions. *Biochem. Pharmacol.* 60, 1091-1099.
2. Kang, Y. and Massague, J. (2004). Epithelial-mesenchymal transitions: twist in development and metastasis. *Cell* 118, 277-279.
3. Thiery, J. P. (2002). Epithelial-mesenchymal transitions in tumour progression. *Nat. Rev. Cancer* 2, 442-454.
4. Yang, J., Mani, S. A., Donaher, J. L., Ramaswamy, S., Itzykson, R. A., Come, C., Savagner, P., Gitelman, I., Richardson, A., and Weinberg, R. A. (2004). Twist, a master regulator of morphogenesis, plays an essential role in tumor metastasis. *Cell* 117, 927-939.
5. Itoh, Y., Takamura, A., Ito, N., Maru, Y., Sato, H., Suenaga, N., Aoki, T., and Seiki, M. (2001). Homophilic complex formation of MT1-MMP facilitates proMMP-2 activation on the cell surface and promotes tumor cell invasion. *EMBO J.* 20, 4782-4793.
6. Mori, H., Tomari, T., Koshikawa, N., Kajita, M., Itoh, Y., Sato, H., Tojo, H., Yana, I., and Seiki, M. (2002). CD44 directs membrane-type 1 matrix metalloproteinase to lamellipodia by associating with its hemopexin-like domain. *EMBO J.* 21, 3949-3959.
7. Suenaga, N., Mori, H., Itoh, Y., and Seiki, M. (2005). CD44 binding through the hemopexin-like domain is critical for its shedding by membrane-type 1 matrix metalloproteinase. *Oncogene* 24, 859-868.
8. Cao, J., Kozarekar, P., Pavlaki, M., Chiarelli, C., Bahou, W. F., and Zucker, S. (2004). Distinct roles for the catalytic and hemopexin domains of membrane type 1-matrix metalloproteinase in substrate degradation and cell migration. *J. Biol. Chem.* 279, 14129-14139.
9. Lever, R. and Page, C. P. (2002). Novel drug development opportunities for heparin. *Nat. Rev. Drug Discov.* 1, 140-148.
10. Hanahan, D. and Weinberg, R. A. (2000). The hallmarks of cancer. *Cell* 100, 57-70.
11. Grunert, S., Jechlinger, M., and Beug, H. (2003). Diverse cellular and molecular mechanisms contribute to epithelial plasticity and metastasis. *Nat. Rev. Mol. Cell Biol.* 4, 657-665.
12. Sternlicht, M. D. and Werb, Z. (2001). How matrix metalloproteinases regulate cell behavior. *Annu. Rev. Cell Dev. Biol.* 17, 463-516.

13. Udayakumar, T. S., Chen, M. L., Bair, E. L., Von Bredow, D. C., Cress, A. E., Nagle, R. B., and Bowden, G. T. (2003). Membrane type-1-matrix metalloproteinase expressed by prostate carcinoma cells cleaves human laminin-5 beta3 chain and induces cell migration. *Cancer Res.* 63, 2292-2299.
14. Zucker, S., Cao, J., and Chen, W. T. (2000). Critical appraisal of the use of matrix metalloproteinase inhibitors in cancer treatment. *Oncogene* 19, 6642-6650.
15. Oft, M., Peli, J., Rudaz, C., Schwarz, H., Beug, H., and Reichmann, E. (1996). TGF-beta1 and Ha-Ras collaborate in modulating the phenotypic plasticity and invasiveness of epithelial tumor cells. *Genes Dev.* 10, 2462-2477.
16. Morali, O. G., Delmas, V., Moore, R., Jeanney, C., Thiery, J. P., and Lame, L. (2001). IGF-II induces rapid beta-catenin relocation to the nucleus during epithelium to mesenchyme transition. *Oncogene* 20, 4942-4950.
17. Savagner, P. (2001). Leaving the neighborhood: molecular mechanisms involved during epithelial-mesenchymal transition. *Bioessays* 23, 912-923.
18. Henderson, B. R. and Fagotto, F. (2002). The ins and outs of APC and beta-catenin nuclear transport. *EMBO Rep.* 3, 834-839.
19. Polakis, P. (2000). Wnt signaling and cancer. *Genes Dev.* 14, 1837-1851.
20. Thiery, J. P. (2003). Epithelial-mesenchymal transitions in development and pathologies. *Curr. Opin. Cell Biol.* 15, 740-746.
21. Petersen, O. W., Nielsen, H. L., Gudjonsson, T., Villadsen, R., Rank, F., Niebuhr, E., Bissell, M. J., and Ronnov-Jessen, L. (2003). Epithelial to mesenchymal transition in human breast cancer can provide a nonmalignant stroma. *Am. J. Pathol.* 162, 391-402.
22. Gotzmann, J., Mikula, M., Eger, A., Schulte-Hermann, R., Foisner, R., Beug, H., and Mikulits, W. (2004). Molecular aspects of epithelial cell plasticity: implications for local tumor invasion and metastasis. *Mutat. Res.* 566, 9-20.
23. Oft, M., Heider, K. H., and Beug, H. (1998). TGFbeta signaling is necessary for carcinoma cell invasiveness and metastasis. *Curr. Biol.* 8, 1243-1252.
24. Janda, E., Lehmann, K., Killisch, I., Jechlinger, M., Herzig, M., Downward, J., Beug, H., and Grunert, S. (2002). Ras and TGF(beta) cooperatively regulate epithelial cell plasticity and metastasis: dissection of Ras signaling pathways. *J. Cell Biol.* 156, 299-313.
25. Cheng, S, and Lovett, D. H. (2003). Gelatinase A (MMP-2) is necessary and sufficient for renal tubular cell epithelial-mesenchymal transformation. *Am. J. Pathol.* 162, 1937-1949.
26. Duong, T. D. and Erickson, C. A. (2004). MMP-2 plays an essential role in producing epithelial-mesenchymal transformations in the avian embryo. *Dev. Dyn.* 229, 42-53.
27. Lochter, A., Galosy, S., Muschler, J., Freedman, N., Werb, Z., and Bissell, M. J. (1997). Matrix metalloproteinase stromelysin-1 triggers a cascade of molecular alterations that leads to stable epithelial-to-mesenchymal conversion and a premalignant phenotype in mammary epithelial cells. *J. Cell Biol.* 139, 1861-1872.
28. Ikenouchi, J., Matsuda, M., Furuse, M., and Tsukita, S. (2003). Regulation of tight junctions during the epithelium-mesenchyme transition: direct repression of the gene expression of claudins/occludin by Snail *J. Cell Sci.* 116, 1959-1967.
29. Seiki, M., Koshikawa, N., and Yana, I. (2003). Role of pericellular proteolysis by membrane-type 1 matrix metalloproteinase in cancer invasion and angiogenesis. *Cancer Metastasis Rev.* 22, 129-143.
30. Zucker, S., Pei, D., Cao, J., and Lopez-Otin, C. (2003). Membrane type-matrix metalloproteinases (MT-MMP). *Curr. Top. Dev. Biol.* 54, 1-74.
31. Hiraoka, N., Allen, E., Apel, I. J., Gyetko, M. R., and Weiss, S. J. (1998). Matrix metalloproteinases regulate neovascularization by acting as pericellular fibrinolysins. *Cell* 95, 365-377.
32. Koshikawa, N., Giannelli, G., Cirulli, V., Miyazaki, K., and Quaranta, V. (2000). Role of cell surface metalloprotease MT1-MMP in epithelial cell migration over laminin-5. *J Cell Biol* 148, 615-24.
33. Hidalgo, M. and Eckhardt, S. G. (2001). Development of matrix metalloproteinase inhibitors in cancer therapy. *J. Natl. Cancer Inst.* 93, 178-193.
34. Zucker, S., Cao, J., and Molloy, C. J. Role of matrix metalloproteinases and plasminogen activators in cancer and metastasis. *Therapeutic strategies*. Anticancer Drug Development. Eds. B. C. Baguley and D. J. Kerr. Academic Press. San Diego, Calif., 91-122. 2002.
35. Coussens, L. M., Fingleton, B., and Matrisian, L. M. (2002). Matrix metalloproteinase inhibitors and cancer: trials and tribulations. *Science* 295, 2387-2392.
36. Egeblad, M. and Werb, Z. (2002). New functions for the matrix metalloproteinases in cancer progression. *Nat. Rev. Cancer* 2, 161-174.
37. Overall, C. M. and Lopez-Otin, C. (2002). Strategies for MMP inhibition in cancer: innovations for the post-trial era. *Nat. Rev. Cancer* 2, 657-672.
38. Pavlaki, M. and Zucker, S. (2003). Matrix metalloproteinase inhibitors (MMPIs): the beginning of phase I or the termination of phase III clinical trials. *Cancer Metastasis Rev.* 22, 177-203.
39. Crino, L., Franceschi, E., and Scopece, L. (2002). HER-2 inhibitors: clinical results. *Suppl Tumori* 1, S3-S4.
40. Aina, O. H., Sroka, T. C., Chen, M. L., and Lam, K. S. (2002). Therapeutic cancer targeting peptides. *Biopolymers* 66, 184-199.
41. Bjorklund, M., Heikkila, P., and Koivunen, E. (2004). Peptide inhibition of catalytic and noncatalytic activities of matrix metalloproteinase-9 blocks tumor cell migration and invasion. *J. Biol. Chem.* 279, 29589-29597.
42. Niv, M. Y., Rubin, H., Cohen, J., Tsirulnikov, L., Licht, T., Peretzman-Shemer, A., Cna'an, E., Tartakovsky, A., Stein, I., Albeck, S., Weinstein, I., Goldenberg-Funuanov, M., Tobi, D., Cohen, E., Laster, M., Ben Sasson, S. A., and Reuveni, H. (2004). Sequence-based design of kinase inhibitors applicable for therapeutics and target identification. *J. Biol. Chem.* 279, 1242-1255.
43. Rauh, D., Klebe, G., and Stubbs, M. T. (2004). Understanding protein-ligand interactions: the price of protein flexibility. *J. Mol. Biol.* 335, 1325-1341.
44. Turk, B. E., Wong, T. Y., Schwarzenbacher, R., Jarrell, E. T., Leppla, S. H., Collier, R. J., Liddington, R. C., and Cantley, L. C. (2004). The structural basis for substrate and inhibitor selectivity of the anthrax lethal factor. *Nat. Struct. Mol. Biol.* 11, 60-66.
45. Bartolome, R. A., Galvez, B. G., Longo, N., Baleux, F., Van Muijen, G. N., Sanchez-Mateos, P., Arroyo, A. G., and Teixido, J. (2004). Stromal cell-derived factor-1alpha promotes melanoma cell invasion across basement membranes involving stimulation of membrane-type 1 matrix metalloproteinase and Rho GTPase activities. *Cancer Res.* 64, 2534-2543.
46. Galvez, B. G., Matias-Roman, S., Yanez-Mo, M., Sanchez-Madrid, F., and Arroyo, A. G. (2002). ECM regulates MT1-MMP localization with beta1 or alphavbeta3

46. integrins at distinct cell compartments modulating its internalization and activity on human endothelial cells. *J. Cell Biol.* 159, 509-521.
47. Mu, D., Cambier, S., Fjellbirkeland, L., Baron, J. L., Munger, J. S., Kawakatsu, H., Sheppard, D., Broaddus, V. C., and Nishimura, S. L. (2002). The integrin alpha(v)beta8 mediates epithelial homeostasis through MT1-MMP-dependent activation of TGF-beta1. *J. Cell Biol.* 157, 493-507.
48. Cao, J., Chiarelli, C., Kozarekar, P., and Adler, H. L. Membrane Type 1-Matrix Metalloproteinase Promotes Human Prostate Cancer Invasion and Metastasis. Thrombosis & Haemostasis (in press). 2005.
49. Deryugina, E. I., Bourdon, M. A., Jungwirth, K., Smith, J. W., and Strongin, A. Y. (2000). Functional activation of integrin alpha V beta 3 in tumor cells expressing membrane-type 1 matrix metalloproteinase. *Int. J. Cancer* 86, 15-23.
50. Nagakawa, 0., Murakami, K., Yamaura, T., Fujiuchi, Y., Murata, J., Fuse, H., and Saiki, I. (2000). Expression of membrane-type 1 matrix metalloproteinase (MT1-MMP) on prostate cancer cell lines. *Cancer Lett* 155, 173-9.
51. Klingelhofer, J., Troyanovsky, R. B., Laur, O. Y., and Troyanovsky, S. (2003). Exchange of catenins in cadherin-catenin complex. *Oncogene* 22, 1181-1188.
52. Zucker, S., Drews, M., Conner, C., Foda, H. D., DeClerck, Y. A., Langley, K. E., Bahou, W. F., Docherty, A. J., and Cao, J. (1998). Tissue inhibitor of metalloproteinase-2 (TIMP-2) binds to the catalytic domain of the cell surface receptor, membrane type 1-matrix metalloproteinase 1 (MT1-MMP). *J Biol Chem* 273, 1216-22.
53. Cheong, K. H., Zacchetti, D., Schneeberger, E. E., and Simons, K. (1999). VIP17/MAL, a lipid raft-associated protein, is involved in apical transport in MDCK cells. *Proc. Natl. Acad. Sci. U.S.A* 96, 6241-6248.
54. Albrecht-Buehler, G. (1977). The phagokinetic tracks of 3T3 cells. *Cell* 11, 395-404.
55. Hotary, K., Allen, E., Punturieri, A., Yana, I., and Weiss, S. J. (2000). Regulation of cell invasion and morphogenesis in a three-dimensional type I collagen matrix by membrane-type matrix metalloproteinases 1, 2, and 3. *J Cell Biol* 149, 1309-23.
56. Uekita, T., Itoh, Y., Yana, I., Ohno, H., and Seiki, M. (2001). Cytoplasmic tail-dependent internalization of membrane-type 1 matrix metalloproteinase is important for its invasion-promoting activity. *J. Cell Biol.* 155, 1345-1356.
57. Wang, P., Nie, J., and Pei, D. (2004). The hemopexin domain of membrane-type matrix metalloproteinase-1 (MT1-MMP) Is not required for its activation of proMMP2 on cell surface but is essential for MT1-MMP-mediated invasion in three-dimensional type I collagen. *J. Biol. Chem.* 279, 51148-51155.
58. Wozniak, M. A., Modzelewska, K., Kwong, L., and Keely, P. J. (2004). Focal adhesion regulation of cell behavior. *Biochim. Biophys. Acta* 1692, 103-119.
59. Sieg, D. J., Hauck, C. R., and Schlaepfer, D. D. (1999). Required role of focal adhesion kinase (FAK) for integrin-stimulated cell migration. *J. Cell Sci.* 112 (Pt 16), 2677-2691.
60. Geiger, B. and Ginsberg, D. (1991). The cytoplasmic domain of adherens-type junctions. *Cell Motil. Cytoskeleton* 20, 1-6.
61. Otto, J. J. (1990). Vinculin. *Cell Motil. Cytoskeleton* 16, 1-6.
62. Hazan, R. B., Kang, L., Roe, S., Borgen, P. I., and Rimm, D. L. (1997). Vinculin is associated with the E-cadherin adhesion complex. *J. Biol. Chem.* 272, 32448-32453.
63. Coll, J. L., Ben Ze'ev, A., Ezzell, R. M., Rodriguez Fernandez, J. L., Baribault, H., Oshima, R. G., and Adamson, E. D. (1995). Targeted disruption of vinculin genes in F9 and embryonic stem cells changes cell morphology, adhesion, and locomotion. *Proc. Natl. Acad. Sci. U.S.A* 92, 9161-9165.
64. Raz, A. and Geiger, B. (1982). Altered organization of cell-substrate contacts and membrane-associated cytoskeleton in tumor cell variants exhibiting different metastatic capabilities. *Cancer Res.* 42, 5183-5190.
65. Matrisian, L. M., Sledge, G. W., Jr., and Mohla, S. (2003). Extracellular proteolysis and cancer: meeting summary and future directions. *Cancer Res.* 63, 6105-6109.
66. Brinckerhoff, C. E. and Matrisian, L. M. (2002). Matrix metalloproteinases: a tail of a frog that became a prince. *Nat. Rev. Mol. Cell Biol.* 3, 207-214.
67. Wolf, K., Mazo, I., Leung, H., Engelke, K., von Andrian, U. H., Deryugina, E. I., Strongin, A. Y., Brocker, E. B., and Friedl, P. (2003). Compensation mechanism in tumor cell migration: mesenchymal-amoeboid transition after blocking of pericellular proteolysis. *J. Cell Biol.* 160, 267-277.
68. Sabeh, F., Ota, I., Holmbeck, K., Birkedal-Hansen, H., Soloway, P., Balbin, M., Lopez-Otin, C., Shapiro, S., Inada, M., Krane, S., Allen, E., Chung, D., and Weiss, S. J. (2004). Tumor cell traffic through the extracellular matrix is controlled by the membrane-anchored collagenase MT1-MMP. *J. Cell Biol.* 167, 769-781.
69. Beavis, M. J., Williams, J. D., Hoppe, J., and Topley, N. (1997). Human peritoneal fibroblast proliferation in 3-dimensional culture: modulation by cytokines, growth factors and peritoneal dialysis effluent. *Kidney Int.* 51, 205-215.
70. Hotary, K. B., Allen, E. D., Brooks, P. C., Datta, N. S., Long, M. W., and Weiss, S. J. (2003). Membrane type I matrix metalloproteinase usurps tumor growth control imposed by the three-dimensional extracellular matrix. *Cell* 114, 33-45.
71. Zucker, S., Hymowitz, M., Rollo, E. E., Mann, R., Conner, C. E., Cao, J., Foda, H. D., Tompkins, D. C., and Toole, B. P. (2001). Tumorigenic potential of extracellular matrix metalloproteinase inducer. *Am. J. Pathol.* 158, 1921-1928.
72. Sounni, N. E., Janssen, M., Foidart, J. M., and Noel, A. (2003). Membrane type-1 matrix metalloproteinase and TIMP-2 in tumor angiogenesis. *Matrix Biol.* 22, 55-61.
73. Deryugina, E. I., Soroceanu, L., and Strongin, A. Y. (2002). Up-regulation of vascular endothelial growth factor by membrane-type 1 matrix metalloproteinase stimulates human glioma xenograft growth and angiogenesis. *Cancer Res.* 62, 580-588.
74. Kajita, M., Itoh, Y., Chiba, T., Mori, H., Okada, A., Kinoh, H., and Seiki, M. (2001). Membrane-type 1 matrix metalloproteinase cleaves CD44 and promotes cell migration. *J. Cell Biol.* 153, 893-904.
75. Bode, W., Fernandez-Catalan, C., Tschesche, H., Grams, F., Nagase, H., and Maskos, K. (1999). Structural properties of matrix metalloproteinases. *Cell Mol. Life Sci.* 55, 639-652.
76. Cha, H., Kopetzki, E., Huber, R., Lanzendorfer, M., and Brandstetter, H. (2002). Structural basis of the adaptive molecular recognition by MMP9. *J. Mol. Biol.* 320, 1065-1079.
77. Zucker, S, and Chen, W T. Membrane Type Matrix Metalloproteinase. Cell Surface Proteases 54, 2-53. 2003. Academic Press.

78. Afzal, S., Lalani, E. N., Poulsom, R., Stubbs, A., Rowlinson, G., Sato, H., Seiki, M., and Stamp, G. W. (1998). MT1-MMP and MMP-2 mRNA expression in human ovarian tumors: possible implications for the role of desmoplastic fibroblasts. *Hum. Pathol.* 29, 155-165.

79. Nakada, M., Nakamura, H., Ikeda, E., Fujimoto, N., Yamashita, J., Sato, H., Seiki, M., and Okada, Y. (1999). Expression and tissue localization of membrane-type 1, 2, and 3 matrix metalloproteinases in human astrocytic tumors. *Am J Pathol* 154, 417-28.

80. Ueda, J Kajita, M., Suenaga, N., Fujii, K., and Seiki, M. (2003). Sequence-specific silencing of MT1-MMP expression suppresses tumor cell migration and invasion: importance of MT1-MMP as a therapeutic target for invasive tumors. *Oncogene* 22, 8716-8722.

81. Chun, T. H., Sabeh, F., Ota, I., Murphy, H., McDonagh, K. T., Holmbeck, K., Birkedal-Hansen, H., Allen, E. D., and Weiss, S. J. (2004). MT1-MMP-dependent neovessel formation within the confines of the three-dimensional extracellular matrix. *J. Cell Biol.* 167, 757-767.

82. Munshi, H. G., Wu, Y. I., Mukhopadhyay, S., Ottaviano, A. J., Sassano, A., Koblinski, J. E., Platanias, L. C., and Stack, M. S. (2004). Differential regulation of membrane type 1-matrix metalloproteinase activity by ERK 1/2- and p38 MAPK-modulated tissue inhibitor of metalloproteinases 2 expression controls transforming growth factor-beta1-induced pericellular collagenolysis. *J. Biol. Chem.* 279, 39042-39050.

83. Hess, A. R., Seftor, E. A., Seftor, R. E., and Hendrix, M. J. (2003). Phosphoinositide 3-kinase regulates membrane Type 1-matrix metalloproteinase (MMP) and MMP-2 activity during melanoma cell vasculogenic mimicry. *Cancer Res.* 63, 4757-4762.

84. Toole, B. P. (2004). Hyaluronan: from extracellular glue to pericellular cue. *Nat. Rev. Cancer* 4, 528-539.

85. Tsatas, D., Kanagasundaram, V., Kaye, A., and Novak, U. (2002). EGF receptor modifies cellular responses to hyaluronan in glioblastoma cell lines. *J. Clin. Neurosci.* 9, 282-288.

86. Sharma, M., Chuang, W. W., and Sun, Z. (2002). Phosphatidylinositol 3-kinase/Akt stimulates androgen pathway through GSK3beta inhibition and nuclear beta-catenin accumulation. *J. Biol. Chem.* 277, 30935-30941.

87. Persad, S., Troussard, A. A., McPhee, T. R., Mulholland, D. J., and Dedhar, S. (2001). Tumor suppressor PTEN inhibits nuclear accumulation of beta-catenin and T cell/lymphoid enhancer factor 1-mediated transcriptional activation. *J. Cell Biol.* 153, 1161-1174.

88. Bachelder, R. E., Yoon, S. O., Franci, C., de Herreros, A. G., and Mercurio, A. M. (2005). Glycogen synthase kinase-3 is an endogenous inhibitor of Snail transcription: implications for the epithelial-mesenchymal transition. *J. Cell Biol.* 168, 29-33.

89. Takino, T., Miyamori, H., Watanabe, Y., Yoshioka, K., Seiki, M., and Sato, H. (2004). Membrane type 1 matrix metalloproteinase regulates collagen-dependent mitogen-activated protein/extracellular signal-related kinase activation and cell migration. *Cancer Res.* 64, 1044-1049.

90. Gingras, D., Bousquet-Gagnon, N., Langlois, S., Lachambre, M. P., Annabi, B., and Beliveau, R. (2001). Activation of the extracellular signal-regulated protein kinase (ERK) cascade by membrane-type-1 matrix metalloproteinase (MT1-MMP). *FEBS Lett.* 507, 231-236.

91. Atkinson, S. J., English, J. L., Holway, N., and Murphy, G. (2004). Cellular cholesterol regulates MT1 MMP dependent activation of MMP 2 via MEK-1 in HT1080 fibrosarcoma cells. *FEBS Lett.* 566, 65-70.

92. Rozanov, D. V., Deryugina, E. I., Monosov, E. Z., Marchenko, N. D., and Strongin, A. Y. (2004). Aberrant, persistent inclusion into lipid rafts limits the tumorigenic function of membrane type-1 matrix metalloproteinase in malignant cells. *Exp. Cell Res.* 293, 81-95.

93. Takahashi, M., Tsunoda, T., Seiki, M., Nakamura, Y., and Furukawa, Y. (2002). Identification of membrane-type matrix metalloproteinase-1 as a target of the beta-catenin/Tcf4 complex in human colorectal cancers. *Oncogene* 21, 5861-5867.

94. Hlubek, F., Spaderna, S., Jung, A., Kirchner, T., and Brabletz, T. (2004). Beta-catenin activates a coordinated expression of the proinvasive factors laminin-5 gamma2 chain and MT1-MMP in colorectal carcinomas. *Int. J. Cancer* 108, 321-326.

95. Park, B. J., Park, J. I., Byun, D. S., Park, J. H., and Chi, S. G. (2000). Mitogenic conversion of transforming growth factor-beta1 effect by oncogenic Ha-Ras-induced activation of the mitogen-activated protein kinase signaling pathway in human prostate cancer. *Cancer Res.* 60, 3031-3038.

96. Enmon, R. M., Jr., O'Connor, K. C., Song, H., Lacks, D. J., and Schwartz, D. K. (2002). Aggregation kinetics of well and poorly differentiated human prostate cancer cells. *Biotechnol. Bioeng.* 80, 580-588.

97. Mitchell, S., Abel, P., Ware, M., Stamp, G., and Lalani, E. (2000). Phenotypic and genotypic characterization of commonly used human prostatic cell lines. *BJU. Int.* 85, 932-944.

98. Bates, R. C. and Mercurio, A. M. (2003). Tumor necrosis factor-alpha stimulates the epithelial-to-mesenchymal transition of human colonic organoids. *Mol. Biol. Cell* 14, 1790-1800.

99. Iwano, M., Plieth, D., Danoff, T. M., Xue, C., Okada, H., and Neilson, E. G. (2002). Evidence that fibroblasts derive from epithelium during tissue fibrosis. *J. Clin. Invest* 110, 341-350.

100. Kawano, K., Kantak, S. S., Murai, M., Yao, C. C., and Kramer, R. H. (2001). Integrin alpha3beta1 engagement disrupts intercellular adhesion. *Exp. Cell Res.* 262, 180-196.

101. Brabletz, T., Jung, A., Reu, S., Porzner, M., Hlubek, F., Kunz-Schughart, L. A., Knuechel, R., and Kirchner, T. (2001). Variable beta-catenin expression in colorectal cancers indicates tumor progression driven by the tumor environment. *Proc. Natl. Acad. Sci. U.S.A* 98, 10356-10361.

102. Strizzi, L., Bianco, C., Normanno, N., Seno, M., Wechselberger, C., Wallace-Jones, B., Khan, N. I., Hirota, M., Sun, Y., Sanicola, M., and Salomon, D. S. (2004). Epithelial mesenchymal transition is a characteristic of hyperplasias and tumors in mammary gland from MMTV-Cripto-1 transgenic mice. *J. Cell Physiol* 201, 266-276.

103. Chesire, D. R., Ewing, C. M., Gage, W. R., and Isaacs, W. B. (2002). In vitro evidence for complex modes of nuclear beta-catenin signaling during prostate growth and tumorigenesis. *Oncogene* 21, 2679-2694.

104. Ito, K., Okamoto, I., Araki, N., Kawano, Y., Nakao, M., Fujiyama, S., Tomita, K., Mimori, T., and Saya, H. (1999). Calcium influx triggers the sequential proteolysis of extracellular and cytoplasmic domains of E-cadherin, leading to loss of beta-catenin from cell-cell contacts. *Oncogene* 18, 7080-7090.

105. Marambaud, P., Shioi, J., Serban, G., Georgakopoulos, A., Sarver, S., Nagy, V., Baki, L., Wen, P., Efthimiopoulos, S., Shao, Z., Wisniewski, T., and Robakis, N. K. (2002). A presenilin-1/gamma-secretase cleavage releases the E-cadherin intracellular domain and regulates disassembly of adherens junctions. *EMBO J.* 21, 1948-1956.

106. Moon, R. T., Bowerman, B., Boutros, M., and Perrimon, N. (2002). The promise and perils of Wnt signaling through beta-catenin. *Science* 296, 1644-1646.

107. Morali, O. G., Delmas, V., Moore, R., Jeanney, C., Thiery, J. P., and Lame, L. (2001). IGF-II induces rapid beta-catenin relocation to the nucleus during epithelium to mesenchyme transition. *Oncogene* 20, 4942-4950.

108. Zhou, B. P., Deng, J., Xia, W., Xu, J., L1, Y. M., Gunduz, M., and Hung, M. C. (2004). Dual regulation of Snail by GSK-3beta-mediated phosphorylation in control of epithelial-mesenchymal transition. *Nat. Cell Biol.* 6, 931-940.

109. Morin, P. J. (1999). beta-catenin signaling and cancer. *Bioessays* 21, 1021-1030.

110. Tan, C., Costello, P., Sanghera, J., Dominguez, D., Baulida, J., de Herreros, A. G., and Dedhar, S. (2001). Inhibition of integrin linked kinase (ILK) suppresses beta-catenin-Lef/Tcf-dependent transcription and expression of the E-cadherin repressor, snail, in APC-/- human colon carcinoma cells. *Oncogene* 20, 133-140.

111. Schafer, R., Abraham, D., Paulus, P., Blumer, R., Grimm, M., Wojta, J., and Aharinejad, S. (2003). Impaired VE-cadherin/beta-catenin expression mediates endothelial cell degeneration in dilated cardiomyopathy. *Circulation* 108, 1585-1591.

112. Huber, M. A., Azoitei, N., Baumann, B., Grunert, S., Sommer, A., Pehamberger, H., Kraut, N., Beug, H., and Wirth, T. (2004). NF-kappaB is essential for epithelial-mesenchymal transition and metastasis in a model of breast cancer progression. *J. Clin. Invest* 114, 569-581.

113. Dong, Z., Crawford, H. C., Lavrovsky, V., Taub, D., Watts, R., Matrisian, L. M., and Colburn, N. H. (1997). A dominant negative mutant of jun blocking 12-O-tetradecanoylphorbol-13-acetate-induced invasion in mouse keratinocytes. *Mol. Carcinog.* 19, 204-212.

114. Loennechen, T., Mathisen, B., Hansen, J., Lindstad, R. I., El Gewely, S. A., Andersen, K., Maelandsmo, G. M., and Winberg, J. O. (2003). Colchicine induces membrane-associated activation of matrix metalloproteinase-2 in osteosarcoma cells in an S100A4-independent manner. *Biochem. Pharmacol.* 66, 2341-2353.

115. Philip, S., Bulbule, A., and Kundu, G. C. (2001). Osteopontin stimulates tumor growth and activation of promatrix metalloproteinase-2 through nuclear factor-kappa B-mediated induction of membrane type 1 matrix metalloproteinase in murine melanoma cells. *J. Biol. Chem.* 276, 44926-44935.

116. Takahra, T., Smart, D. E., Oakley, F., and Mann, D. A. (2004). Induction of myofibroblast MMP-9 transcription in three-dimensional collagen I gel cultures: regulation by NF-kappaB, AP-1 and Sp1. *Int. J. Biochem. Cell Biol.* 36, 353-363.

117. Birkedal-Hansen, H., Moore, W. G., Bodden, M. K., Windsor, L. J., Birkedal-Hansen, B., DeCarlo, A., and Engler, J. A. (1993). Matrix metalloproteinases: a review. *Crit. Rev Oral Biol Med* 4, 197-250.

118. Sato, H., Takino, T., Okada, Y., Cao, J., Shinagawa, A., Yamamoto, E., and Seiki, M. (1994). A matrix metalloproteinase expressed on the surface of invasive tumour cells (see comments). *Nature* 370, 61-5.

119. Cao, J., Sato, H., Takino, T., and Seiki, M. (1995). The C-terminal region of membrane type matrix metalloproteinase is a functional transmembrane domain required for pro-gelatinase A activation. *J Biol Chem* 270, 801-5.

120. Pavlaki, M., Cao, J., Hymowitz, M., Chen, W. T., Bahou, W., and Zucker, S. (2002). A conserved sequence within the propeptide domain of membrane type 1 matrix metalloproteinase is critical for function as an intramolecular chaperone. *J. Biol. Chem.* 277, 2740-2749.

121. Ohuchi, E., Imai, K., Fujii, Y., Sato, H., Seiki, M., and Okada, Y. (1997). Membrane type 1 matrix metalloproteinase digests interstitial collagens and other extracellular matrix macromolecules. *J Biol Chem* 272, 2446-51.

122. Tam, E. M., Wu, Y. I., Butler, G. S., Stack, M. S., and Overall, C. M. (2002). Collagen binding properties of the membrane type-1 matrix metalloproteinase (MT1-MMP) hemopexin C domain. The ectodomain of the 44-kDa autocatalytic product of MT1-MMP inhibits cell invasion by disrupting native type I collagen cleavage. *J. Biol. Chem.* 277, 39005-39014.

123. Jiang, A., Lehti, K., Wang, X., Weiss, S. J., Keski-Oja, J., and Pei, D. (2001). Regulation of membrane-type matrix metalloproteinase 1 activity by dynamin-mediated endocytosis. *Proc. Natl. Acad. Sci. U.S.A* 98, 13693-13698.

124. Li, J., Brick, P., O'Hare, M. C., Skarzynski, T., Lloyd, L. F., Curry, V. A., Clark, I. M., Bigg, H. F., Hazleman, B. L., Cawston, T. E., and (1995). Structure of full-length porcine synovial collagenase reveals a C-terminal domain containing a calcium-linked, four-bladed beta-propeller. *Structure.* 3, 541-549.

125. Balbo, A., Minor, K. H., Velikovsky, C. A., Mariuzza, R. A., Peterson, C. B., and Schuck, P. (2005). Studying multiprotein complexes by multisignal sedimentation velocity analytical ultracentrifugation. *Proc. Natl. Acad. Sci. U.S.A* 102, 81-86.

126. Pall, T., Gad, A., Kasak, L., Drews, M., Stromblad, S., and Kogerman, P. (2004). Recombinant CD44-HABD is a novel and potent direct angiogenesis inhibitor enforcing endothelial cell-specific growth inhibition independently of hyaluronic acid binding. *Oncogene* 23, 7874-7881.

127. van, d., V, Taher, T. E., Wielenga, V. J., Spaargaren, M., Prevo, R., Smit, L., David, G., Hartmann, G., Gherardi, E., and Pals, S. T. (1999). Heparan sulfate-modified CD44 promotes hepatocyte growth factor/scatter factor-induced signal transduction through the receptor tyrosine kinase c-Met. *J. Biol. Chem.* 274, 6499-6506.

128. Bennett, K. L., Jackson, D. G., Simon, J. C., Tanczos, E., Peach, R., Modrell, B., Stamenkovic, I., Plowman, G., and Aruffo, A. (1995). CD44 isoforms containing exon V3 are responsible for the presentation of heparin-binding growth factor. *J. Cell Biol.* 128, 687-698.

129. Jalkanen, S, and Jalkanen, M. (1992). Lymphocyte CD44 binds the COOH-terminal heparin-binding domain of fibronectin. *J. Cell Biol.* 116, 817-825.

130. Miura, Y., Takahashi, T., Jung, S. M., and Moroi, M. (2002). Analysis of the interaction of platelet collagen receptor glycoprotein VI (GPVI) with collagen. A dimeric form of GPVI, but not the monomeric form, shows affinity to fibrous collagen. *J. Biol. Chem.* 277, 46197-46204.

131. Brown, P. D. (1998). Matrix metalloproteinase inhibitors. *Angiogenesis.* 1, 142-154.

132. Fingleton, B. M., Heppner Goss, K. J., Crawford, H. C., and Matrisian, L. M. (1999). Matrilysin in early stage intestinal tumorigenesis. *APMIS* 107, 102-110.

133. Bergers, G., Javaherian, K., Lo, K. M., Folkman, J., and Hanahan, D. (1999). Effects of angiogenesis inhibitors on multistage carcinogenesis in mice. *Science* 284, 808-812.

134. Brooks, P. C., Silletti, S., von Schalscha, T. L., Friedlander, M., and Cheresh, D. A. (1998). Disruption of angiogenesis by PEX, a noncatalytic metalloproteinase fragment with integrin binding activity. *Cell* 92, 391-400.

135. Vivinus-Nebot, M., Rousselle, P., Breittmayer, J. P., Cenciarini, C., Berrih-Aknin, S, Spong, S., Nokelainen, P., Cottrez, F., Marinkovich, M. P., and Bernard, A. (2004). Mature human thymocytes migrate on laminin-5 with activation of metalloproteinase-14 and cleavage of CD44. *J. Immunol.* 172, 1397-1406.
136. Toogood, P. L. (2002). Inhibition of protein-protein association by small molecules: approaches and progress. *J. Med. Chem.* 45, 1543-1558.
137. Loughlin, W. A., Tyndall, J. D., Glenn, M. P., and Fairlie, D. P. (2004). Beta-strand mimetics. *Chem. Rev.* 104, 6085-6117.
138. Ellerby, H. M., Arap, W., Ellerby, L. M., Kain, R., Andrusiak, R., Rio, G. D., Krajewski, S., Lombardo, C. R., Rao, R., Ruoslahti, E., Bredesen, D. E., and Pasqualini, R. (1999). Anti-cancer activity of targeted pro-apoptotic peptides. *Nat. Med.* 5, 1032-1038.
139. Arap, W., Haedicke, W., Bernasconi, M., Kain, R., Rajotte, D., Krajewski, S., Ellerby, H. M., Bredesen, D. E., Pasqualini, R., and Ruoslahti, E. (2002). Targeting the prostate for destruction through a vascular address. *Proc. Natl. Acad. Sci. U.S.A* 99, 1527-1531.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiment, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A method for reducing one or more symptoms of a disease associated with cell expression of a matrix metalloproteinase (MMP), comprising
   a) providing
      i) a mammalian subject in need of reducing one or more symptoms of said disease, and
      ii) a composition comprising a purified polypeptide that contains an amino acid sequence selected from the group consisting of GYPMP (SEQ ID NO:04), VMDGYPMP (SEQ ID NO:01), and GYPKSALR (SEQ ID NO:03), wherein said polypeptide does not comprise a PEX domain of a MMP, is covalently linked to a cytotoxic agent or to a prodrug of said cytotoxic agent and reduces at least one of homodimerization and heterodimerization of an MMP that contains said amino acid sequence, and
   b) administering to said subject a therapeutic amount of said composition to produce a treated subject, wherein said administering is under conditions for reducing one or more symptoms of said disease.

2. The method of claim 1, further comprising c) detecting a reduction in one or more symptoms of said disease in said treated subject.

3. The method of claim 1, wherein one or more symptoms of said disease comprises increased cell migration in the presence of an MMP compared to in the absence of an MMP.

4. The method of claim 3, wherein said therapeutic amount of said composition specifically reduces cell migration that is mediated by MT1-MMP.

5. The method of claim 4, wherein said composition comprises an amount of said polypeptide that reduces homodimerization of MT1-MMP.

6. The method of claim 4, wherein said composition comprises an amount of said polypeptide that reduces heterodimerization of MT1-MMP and CD44.

7. The method of claim 1, wherein said disease comprises cancer metastasis.

8. A method, comprising
   a) providing
      i) a mammalian subject in need of reducing one or more symptoms of a disease associated with cell expression of a matrix metalloproteinase, and ii) a purified polypeptide selected from the group consisting of GYPMP (SEQ ID NO:04), VMDGYPMP (SEQ ID NO:01), and GYPKSALR (SEQ ID NO:03), and b) administering to said subject a therapeutic amount of said purified polypeptide to under conditions such that one or more symptoms of said disease are reduced.

9. The method of claim 8, wherein said purified polypeptide is administered as a pharmaceutical composition.

10. A method for reducing cell migration, comprising
a) providing
   i) a cell expressing a matrix metalloproteinase (MMP), wherein said cell is capable of migration, and
   ii) a purified polypeptide selected from the group consisting of GYPMP (SEQ ID NO:04), VMDGYPMP (SEQ ID NO:01), and GYPKSALR (SEQ ID NO:03), and
b) administering said purified polypeptide to said cell under conditions for reducing migration of said cell.

11. The method of claim 8, wherein said purified polypeptide is administered as a pharmaceutical composition.

* * * * *